US012723082B2

(12) United States Patent
Chen et al.

(10) Patent No.: US 12,723,082 B2
(45) Date of Patent: Sep. 1, 2026

(54) MONOCLONAL ANTIBODIES WHICH BIND PD-1, ENCODING NUCLEOTIDES THEREOF AND METHOD OF USE THEREOF TO TREAT CANCER, INFECTIOUS DISEASE AND INFLAMMATORY DISEASE

(71) Applicant: BIOSION INC., Nanjing (CN)

(72) Inventors: Mingjiu Chen, Nanjing (CN); Shukai Xia, Nanjing (CN); Mark Zhiqing Ma, Nanjing (CN); Zeyu Peng, Nanjing (CN)

(73) Assignee: BIOSION INC., Nanjing (CN)

( * ) Notice: Subject to any disclaimer, the term of this patent is extended or adjusted under 35 U.S.C. 154(b) by 708 days.

(21) Appl. No.: 18/042,650

(22) PCT Filed: Aug. 30, 2021

(86) PCT No.: PCT/CN2021/115313
§ 371 (c)(1),
(2) Date: Feb. 23, 2023

(87) PCT Pub. No.: WO2022/042720
PCT Pub. Date: Mar. 3, 2022

(65) Prior Publication Data
US 2023/0331848 A1 Oct. 19, 2023

Related U.S. Application Data

(60) Provisional application No. 63/072,421, filed on Aug. 31, 2020.

(51) Int. Cl.
*C07K 16/28* (2006.01)
*A61K 39/00* (2006.01)
*A61P 35/00* (2006.01)

(52) U.S. Cl.
CPC .......... *C07K 16/2818* (2013.01); *A61P 35/00* (2018.01); *A61K 2039/505* (2013.01); *C07K 2317/24* (2013.01); *C07K 2317/565* (2013.01); *C07K 2317/76* (2013.01); *C07K 2317/92* (2013.01)

(58) Field of Classification Search
CPC ............ C07K 16/2818; C07K 2317/24; C07K 2317/565; C07K 2317/76; C07K 2317/92; A61P 35/00; A61P 31/00; A61P 29/00; A61K 2039/505
See application file for complete search history.

(56) References Cited

U.S. PATENT DOCUMENTS

2014/0356363 A1 12/2014 Zhou
2015/0203579 A1 7/2015 Papadopoulos
2018/0118829 A1 5/2018 Mabry, III
2020/0255525 A1 8/2020 Bennett et al.
2020/0400098 A1 12/2020 Gormley

FOREIGN PATENT DOCUMENTS

| | | | |
|---|---|---|---|
| CN | 104250302 | A | 12/2014 |
| CN | 106046162 | A | 10/2016 |
| CN | 106519034 | A | 3/2017 |
| CN | 109485727 | A | 3/2019 |
| CN | 109789205 | A | 5/2019 |
| CN | 112074297 | A | 12/2020 |
| JP | 2016523265 | A | 8/2016 |
| WO | 2008156712 | A1 | 12/2008 |
| WO | 2014179664 | A2 | 11/2014 |
| WO | 2017024515 | A1 | 2/2017 |
| WO | 2017055547 | A1 | 4/2017 |
| WO | 2017133540 | A1 | 8/2017 |
| WO | 2018053709 | A1 | 3/2018 |
| WO | 2018087143 | A2 | 5/2018 |
| WO | 2019204132 | A1 | 10/2019 |
| WO | 2020156509 | A1 | 8/2020 |

OTHER PUBLICATIONS

Zhao J, et al. (Aug. 2021) Neurosci. Bull. 37(8):1188-1202. (doi: 10.1007/s12264-021-00683-y).*
A.S. Adler, et al. Rare, high-affinity mouse anti-PD-1 antibodies that function in checkpoint blockade, discovered using microfluidics and molecular genomics, mAbs (Sep. 22, 2017) vol. 9, No. 8, p. 1270-1281.
Int'l Search Report and Written Opinion dated Nov. 26, 2021 issued in Int'l Application No. PCT/CN2021/115313.
EPO, supplementary European Search Report and Written Opinion issued to counterpart European application 21860552, filed Jun. 7, 2024.
JPO, Office Action issued to counterpart Japanese application 2023-507883, Feb. 29, 2024.
CNIPA, Office Action issued to counterpart Chinese application 202180052577.5, Jul. 7, 2025.

* cited by examiner

*Primary Examiner* — Robert S Landsman
(74) *Attorney, Agent, or Firm* — Duane Morris LLP; Thomas J. Kowalski

(57) ABSTRACT

An isolated monoclonal antibody that specifically binds human PD-1, or the antigen-binding portion thereof. A nucleic acid molecule encoding the antibody or the antigen-binding portion thereof, an expression vector, a host cell and a method for expressing the antibody or the antigen-binding portion thereof are also provided. Further provided is a bispecific molecule and a pharmaceutical composition comprising the antibody or the antigen-binding portion thereof, as well as a treatment method using the anti-PD-1 antibody or the antigen-binding portion thereof.

18 Claims, 12 Drawing Sheets

Specification includes a Sequence Listing.

| | mouse E1A9C8A7 | mouse E2G4E10B7 | Keytruda |
|---|---|---|---|
| EC50 | 0.05543 | 0.06469 | 0.1181 |

| | mouse E1G5D1H1 | Keytruda |
|---|---|---|
| EC50 | 0.03791 | 0.1128 |

| | mouse E1A9C8A7 | mouse E2G4E10B7 |
|---|---|---|
| EC50 | 0.1851 | 0.3395 |

| | mouse E1A9C8A7 | mouse E2G4E10B7 | Keytruda |
|---|---|---|---|
| EC50 | 0.1206 | 0.1664 | 0.09566 |

| | mouse E1G5D1H1 | Keytruda |
|---|---|---|
| EC50 | 0.1421 | 0.09305 |

| | mouse E1A9C8A7 | mouse E2G4E10B7 | Keytruda |
|---|---|---|---|
| EC50 | 0.3698 | 0.4832 | 0.234 |

| | mouse E1G5D1H1 | Keytruda |
|---|---|---|
| EC50 | 0.2295 | 0.2367 |

| | mouse E1A9C8A7 | mouse E2G4E10B7 |
|---|---|---|
| EC50 | 1.266 | 0.8703 |

| | mouse E1A9C8A7 | mouse E2G4E10B7 | Keytruda |
|---|---|---|---|
| IC50 | 0.4496 | 0.4282 | 0.3446 |

| | mouse E1G5D1H1 | Keytruda |
|---|---|---|
| IC50 | 0.4336 | 0.37 |

| | mouse E1A9C8A7 | mouse E2G4E10B7 | Keytruda |
|---|---|---|---|
| IC50 | 0.7824 | 0.4842 | 0.3204 |

| | mouse E1G5D1H1 | Keytruda |
|---|---|---|
| IC50 | 0.4959 | 0.3267 |

| | mouse E1A9C8A7 | mouse E2G4E10B7 |
|---|---|---|
| IC50 | 6.856 | 2.49 |

| | mouse E1A9C8A7 | mouse E2G4E10B7 | Keytruda |
|---|---|---|---|
| IC50 | 0.09824 | 0.1618 | 0.07585 |

| | mouse E1G5D1H1 | Keytruda |
|---|---|---|
| IC50 | 0.06285 | 0.07354 |

| | mouse E1A9C8A7 | mouse E2G4E10B7 |
|---|---|---|
| EC50 | 3.893 | 6.936 |

| mouse E1G5D1H1 | Opdivo | Keytruda |
|---|---|---|
| 2.823 | 7.059 | 3.932 |

| | mouse E1A9C8A7 | chimeric E1A9C8A7 | Opdivo | Keytruda |
|---|---|---|---|---|
| EC50 | 4.632 | 4.26 | 9.102 | 2.211 |

| | mouse E1A9C8A7 | chimeric E1A9C8A7 |
|---|---|---|
| EC50 | 0.14 | 0.2136 |

| huE1A9C8A7-V5 | huE1A9C8A7-V8 | Opdivo | Keytruda |
|---|---|---|---|
| 0.2146 | 0.2121 | 0.3352 | 0.7395 |

| | mouse E1A9C8A7 | chimeric E1A9C8A7 |
|---|---|---|
| EC50 | 0.07329 | 0.8506 |

| huE1A9C8A7-V5 | huE1A9C8A7-V8 | Opdivo | Keytruda |
|---|---|---|---|
| 0.8995 | 0.8218 | 0.2275 | 0.1955 |

| | EC50 |
|---|---|
| mouse E1A9C8A7 | 0.4402 |
| chimeric E1A9C8A7 | 0.6677 |
| huE1A9C8A7-V5 | 0.6585 |
| huE1A9C8A7-V8 | 0.6292 |
| Keytruda | 0.1828 |
| Opdivo | 0.4697 |

| | mouse E1A9C8A7 | chimeric E1A9C8A7 |
|---|---|---|
| IC50 | 0.3731 | 0.3772 |

| huE1A9C8A7-V5 | huE1A9C8A7-V8 | Opdivo | Keytruda |
|---|---|---|---|
| 0.3453 | 0.3334 | 0.2841 | 0.2235 |

| | mouse E1A9C8A7 | chimeric E1A9C8A7 |
|---|---|---|
| IC50 | 0.4805 | 0.6112 |

| huE1A9C8A7-V5 | huE1A9C8A7-V8 | Opdivo | Keytruda |
|---|---|---|---|
| 0.5358 | 0.5125 | 7.097 | 3.239 |

| | IC50 |
|---|---|
| mouse E1A9C8A7 | 0.415 |
| chimeric E1A9C8A7 | 0.5694 |
| huE1A9C8A7-V5 | 0.5385 |
| huE1A9C8A7-V8 | 0.5505 |
| Keytruda | 0.4916 |
| Opdivo | 0.5232 |

| | mouse E1A9C8A7 | chimeric E1A9C8A7 |
|---|---|---|
| EC50 | 6.623 | 7.453 |

| huE1A9C8A7-V5 | huE1A9C8A7-V8 | Opdivo | Keytruda |
|---|---|---|---|
| 9.295 | 5.126 | 8.034 | 2.608 |

| | EC50 |
|---|---|
| huAb-E1A9C8A7-V8 | 0.4611 |
| huAb-E1A9C8A7-V8-3 | 0.4514 |

| | EC50 |
|---|---|
| Keytruda | 0.9174 |
| Opdivo | 1.829 |
| huAb-E1A9C8A7-V8 | 1.379 |
| huAb-E1A9C8A7-V8-3 | 1.25 |

SEQUENCE LISTING

```
<160> NUMBER OF SEQ ID NOS: 42

<210> SEQ ID NO 1
<211> LENGTH: 5
<212> TYPE: PRT
<213> ORGANISM: Artificial Sequence
<220> FEATURE:
<223> OTHER INFORMATION: VH CDR1 of mouse, chimeric and humanized
      E1A9C8A7 antibodies, and mouse E2G4E10B7

<400> SEQUENCE: 1

Asp Tyr Val Met His
1               5


<210> SEQ ID NO 2
<211> LENGTH: 5
<212> TYPE: PRT
<213> ORGANISM: Artificial Sequence
<220> FEATURE:
<223> OTHER INFORMATION: VH CDR1 of mouse E1G5D1H1

<400> SEQUENCE: 2

Asp Phe Tyr Met Tyr
1               5


<210> SEQ ID NO 3
<211> LENGTH: 17
<212> TYPE: PRT
<213> ORGANISM: Artificial Sequence
<220> FEATURE:
<223> OTHER INFORMATION: VH CDR2 of mouse, chimeric and humanized
      E1A9C8A7 antibodies

<400> SEQUENCE: 3

Val Ile Ser Thr Tyr His Ile Pro Ala Val Tyr Asn Gln Lys Phe Lys
1               5                   10                  15

Gly


<210> SEQ ID NO 4
<211> LENGTH: 17
<212> TYPE: PRT
<213> ORGANISM: Artificial Sequence
<220> FEATURE:
<223> OTHER INFORMATION: VH CDR2 of mouse E2G4E10B7

<400> SEQUENCE: 4

Val Ile Ser Thr His Phe Gly Asp Gly Val Tyr Asn Gln Lys Phe Lys
1               5                   10                  15
```

Gly

<210> SEQ ID NO 5
<211> LENGTH: 17
<212> TYPE: PRT
<213> ORGANISM: Artificial Sequence
<220> FEATURE:
<223> OTHER INFORMATION: VH CDR2 of mouse E1G5D1H1

<400> SEQUENCE: 5

Thr Ile Ser Asn Ser Gly Thr Gln Thr Tyr Tyr Leu Asp Ser Val Lys
1 5 10 15

Gly

<210> SEQ ID NO 6
<211> LENGTH: 11
<212> TYPE: PRT
<213> ORGANISM: Artificial Sequence
<220> FEATURE:
<223> OTHER INFORMATION: VH CDR3 of mouse, chimeric and humanized E1A9C8A7 antibodies, and mouse E2G4E10B7
<220> FEATURE:
<221> NAME/KEY: misc_feature
<222> LOCATION: (5)..(5)
<223> OTHER INFORMATION: Xaa can be Asp or Glu
<220> FEATURE:
<221> NAME/KEY: misc_feature
<222> LOCATION: (7)..(7)
<223> OTHER INFORMATION: Xaa can be Tyr or Trp

<400> SEQUENCE: 6

Glu Val Tyr Gly Xaa Ser Xaa Tyr Phe Asp Val
1 5 10

<210> SEQ ID NO 7
<211> LENGTH: 12
<212> TYPE: PRT
<213> ORGANISM: Artificial Sequence
<220> FEATURE:
<223> OTHER INFORMATION: VH CDR3 of mouse E1G5D1H1

<400> SEQUENCE: 7

Asp Tyr Tyr Arg Tyr Asp Ser Trp Tyr Phe Asp Val
1 5 10

<210> SEQ ID NO 8
<211> LENGTH: 16
<212> TYPE: PRT
<213> ORGANISM: Artificial Sequence
<220> FEATURE:
<223> OTHER INFORMATION: VL CDR1 of mouse, chimeric and humanized E1A9C8A7 antibodies, and mouse E2G4E10B7
<220> FEATURE:
<221> NAME/KEY: misc_feature
<222> LOCATION: (6)..(6)
<223> OTHER INFORMATION: Xaa can be Ile or Leu
<220> FEATURE:
<221> NAME/KEY: misc_feature
<222> LOCATION: (10)..(10)
<223> OTHER INFORMATION: Xaa can be Asn, Ala, or Asp

<400> SEQUENCE: 8

Arg Ser Ser Gln Ser Xaa Val His Ser Xaa Gly Asn Thr Tyr Leu Glu
1 5 10 15

<210> SEQ ID NO 9
<211> LENGTH: 15
<212> TYPE: PRT

<213> ORGANISM: Artificial Sequence
<220> FEATURE:
<223> OTHER INFORMATION: VL CDR1 of mouse E1G5D1H1

<400> SEQUENCE: 9

Arg Ala Ser Glu Ser Val Asp Phe Tyr Gly Thr Ser Leu Met Gln
1 5 10 15

<210> SEQ ID NO 10
<211> LENGTH: 7
<212> TYPE: PRT
<213> ORGANISM: Artificial Sequence
<220> FEATURE:
<223> OTHER INFORMATION: VL CDR2 of mouse, chimeric and humanized E1A9C8A7 antibodies, and mouse E2G4E10B7

<400> SEQUENCE: 10

Lys Val Ser Asn Arg Phe Ser
1 5

<210> SEQ ID NO 11
<211> LENGTH: 7
<212> TYPE: PRT
<213> ORGANISM: Artificial Sequence
<220> FEATURE:
<223> OTHER INFORMATION: VL CDR2 of mouse E1G5D1H1

<400> SEQUENCE: 11

Ala Ala Ser Asn Val Glu Ser
1 5

<210> SEQ ID NO 12
<211> LENGTH: 9
<212> TYPE: PRT
<213> ORGANISM: Artificial Sequence
<220> FEATURE:
<223> OTHER INFORMATION: VL CDR3 of mouse, chimeric and humanized E1A9C8A7 antibodies, and mouse E2G4E10B7

<400> SEQUENCE: 12

Phe Gln Gly Ser His Val Pro Tyr Thr
1 5

<210> SEQ ID NO 13
<211> LENGTH: 9
<212> TYPE: PRT
<213> ORGANISM: Artificial Sequence
<220> FEATURE:
<223> OTHER INFORMATION: VL CDR3 of mouse E1G5D1H1

<400> SEQUENCE: 13

Gln Gln Ser Arg Lys Val Pro Trp Thr
1 5

<210> SEQ ID NO 14
<211> LENGTH: 120
<212> TYPE: PRT
<213> ORGANISM: Artificial Sequence
<220> FEATURE:
<223> OTHER INFORMATION: VH of mouse and chimeric E1A9C8A7 antibodies

<400> SEQUENCE: 14

Gln Val Gln Leu Gln Gln Ser Gly Ala Glu Val Val Arg Pro Gly Val
1 5 10 15

Ser Val Arg Ile Ser Cys Lys Gly Ser Gly Tyr Thr Phe Ser Asp Tyr
20 25 30

```
Val Met His Trp Met Lys Gln Ser His Gly Glu Ser Leu Glu Trp Ile
        35                  40                  45

Gly Val Ile Ser Thr Tyr His Ile Pro Ala Val Tyr Asn Gln Lys Phe
    50                  55                  60

Lys Gly Lys Ala Thr Met Thr Val Asp Lys Ser Ser Ser Thr Val Tyr
65                  70                  75                  80

Leu Glu Leu Ala Arg Leu Thr Ser Glu Asp Ser Ala Ile Tyr Tyr Cys
                85                  90                  95

Ala Arg Glu Val Tyr Gly Asp Ser Tyr Tyr Phe Asp Val Trp Gly Ala
            100                 105                 110

Gly Thr Thr Val Thr Val Ser Ser
        115                 120


<210> SEQ ID NO 15
<211> LENGTH: 120
<212> TYPE: PRT
<213> ORGANISM: Artificial Sequence
<220> FEATURE:
<223> OTHER INFORMATION: VH of huE1A9C8A7-V1 to huE1A9C8A7-V5
<220> FEATURE:
<221> NAME/KEY: misc_feature
<222> LOCATION: (30)..(30)
<223> OTHER INFORMATION: Xaa can be Ser or Thr
<220> FEATURE:
<221> NAME/KEY: misc_feature
<222> LOCATION: (37)..(37)
<223> OTHER INFORMATION: Xaa can be Met or Val
<220> FEATURE:
<221> NAME/KEY: misc_feature
<222> LOCATION: (74)..(74)
<223> OTHER INFORMATION: Xaa can be Lys or Thr

<400> SEQUENCE: 15

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Xaa Asp Tyr
            20                  25                  30

Val Met His Trp Xaa Arg Gln Ala Pro Gly Gln Ser Leu Glu Trp Ile
        35                  40                  45

Gly Val Ile Ser Thr Tyr His Ile Pro Ala Val Tyr Asn Gln Lys Phe
    50                  55                  60

Lys Gly Lys Ala Thr Met Thr Val Asp Xaa Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Glu Val Tyr Gly Asp Ser Tyr Tyr Phe Asp Val Trp Gly Gln
            100                 105                 110

Gly Thr Thr Val Thr Val Ser Ser
        115                 120


<210> SEQ ID NO 16
<211> LENGTH: 120
<212> TYPE: PRT
<213> ORGANISM: Artificial Sequence
<220> FEATURE:
<223> OTHER INFORMATION: VH of huE1A9C8A7-V6 to huE1A9C8A7-V8
<220> FEATURE:
<221> NAME/KEY: misc_feature
<222> LOCATION: (20)..(20)
<223> OTHER INFORMATION: Xaa can be Val or Ile
<220> FEATURE:
<221> NAME/KEY: misc_feature
<222> LOCATION: (44)..(44)
<223> OTHER INFORMATION: Xaa can be Ser or Gly
```

```
<220> FEATURE:
<221> NAME/KEY: misc_feature
<222> LOCATION: (48)..(48)
<223> OTHER INFORMATION: Xaa can be Ile or Met

<400> SEQUENCE: 16

Gln Val Gln Leu Val Gln Ser Gly Ala Glu Val Val Lys Pro Gly Ala
1               5                   10                  15

Ser Val Lys Xaa Ser Cys Lys Ala Ser Gly Tyr Thr Phe Thr Asp Tyr
            20                  25                  30

Val Met His Trp Val Arg Gln Ala Pro Gly Gln Xaa Leu Glu Trp Xaa
        35                  40                  45

Gly Val Ile Ser Thr Tyr His Ile Pro Ala Val Tyr Asn Gln Lys Phe
    50                  55                  60

Lys Gly Lys Ala Thr Met Thr Val Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Glu Val Tyr Gly Asp Ser Tyr Tyr Phe Asp Val Trp Gly Gln
            100                 105                 110

Gly Thr Thr Val Thr Val Ser Ser
        115                 120


<210> SEQ ID NO 17
<211> LENGTH: 120
<212> TYPE: PRT
<213> ORGANISM: Artificial Sequence
<220> FEATURE:
<223> OTHER INFORMATION: VH of huE1A9C8A7-V9 to huE1A9C8A7-V11
<220> FEATURE:
<221> NAME/KEY: misc_feature
<222> LOCATION: (67)..(67)
<223> OTHER INFORMATION: Xaa can be Arg or Lys
<220> FEATURE:
<221> NAME/KEY: misc_feature
<222> LOCATION: (68)..(68)
<223> OTHER INFORMATION: Xaa can be Ala or Val
<220> FEATURE:
<221> NAME/KEY: misc_feature
<222> LOCATION: (72)..(72)
<223> OTHER INFORMATION: Xaa can be Val or Arg

<400> SEQUENCE: 17

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Val Met His Trp Val Arg Gln Ala Pro Gly Gln Ser Leu Glu Trp Ile
        35                  40                  45

Gly Val Ile Ser Thr Tyr His Ile Pro Ala Val Tyr Asn Gln Lys Phe
    50                  55                  60

Lys Gly Xaa Xaa Thr Met Thr Xaa Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Glu Val Tyr Gly Asp Ser Tyr Tyr Phe Asp Val Trp Gly Gln
            100                 105                 110

Gly Thr Thr Val Thr Val Ser Ser
        115                 120


<210> SEQ ID NO 18
```

<211> LENGTH: 120
<212> TYPE: PRT
<213> ORGANISM: Artificial Sequence
<220> FEATURE:
<223> OTHER INFORMATION: VH of mouse E2G4E10B7

<400> SEQUENCE: 18

```
Gln Val Gln Leu Gln Gln Ser Gly Ala Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Val Met His Trp Val Arg Gln Ser His Ala Lys Ser Leu Glu Trp Ile
        35                  40                  45

Gly Val Ile Ser Thr His Phe Gly Asp Gly Val Tyr Asn Gln Lys Phe
    50                  55                  60

Lys Gly Lys Ala Thr Met Thr Val Asp Lys Ser Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Glu Val Tyr Gly Asp Ser Trp Tyr Phe Asp Val Trp Gly Ala
            100                 105                 110

Gly Thr Thr Val Thr Val Ser Ser
        115                 120
```

<210> SEQ ID NO 19
<211> LENGTH: 121
<212> TYPE: PRT
<213> ORGANISM: Artificial Sequence
<220> FEATURE:
<223> OTHER INFORMATION: VH of mouse E1G5D1H1

<400> SEQUENCE: 19

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Phe
            20                  25                  30

Tyr Met Tyr Trp Val Arg Gln Thr Pro Glu Lys Arg Leu Glu Trp Val
        35                  40                  45

Ala Thr Ile Ser Asn Ser Gly Thr Gln Thr Tyr Tyr Leu Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Ala Arg Asp Tyr Tyr Arg Tyr Asp Ser Trp Tyr Phe Asp Val Trp Gly
            100                 105                 110

Ala Gly Thr Thr Val Thr Val Ser Ser
        115                 120
```

<210> SEQ ID NO 20
<211> LENGTH: 112
<212> TYPE: PRT
<213> ORGANISM: Artificial Sequence
<220> FEATURE:
<223> OTHER INFORMATION: VL for mouse and chimeric E1A9C8A7

<400> SEQUENCE: 20

```
Asp Val Leu Met Thr Gln Ile Pro Leu Ser Leu Pro Val Ser Leu Gly
1               5                   10                  15
```

```
Asp Gln Val Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110


<210> SEQ ID NO 21
<211> LENGTH: 112
<212> TYPE: PRT
<213> ORGANISM: Artificial Sequence
<220> FEATURE:
<223> OTHER INFORMATION: VL of huE1A9C8A7-V1 - huE1A9C8A7-V11, and
      huE1A9C8A7-V8-3
<220> FEATURE:
<221> NAME/KEY: misc_feature
<222> LOCATION: (33)..(33)
<223> OTHER INFORMATION: Xaa can be Asn or Ala

<400> SEQUENCE: 21

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Xaa Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110


<210> SEQ ID NO 22
<211> LENGTH: 112
<212> TYPE: PRT
<213> ORGANISM: Artificial Sequence
<220> FEATURE:
<223> OTHER INFORMATION: VL of mouse E2G4E10B7

<400> SEQUENCE: 22

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80
```

-continued

```
Ser Arg Leu Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110


<210> SEQ ID NO 23
<211> LENGTH: 111
<212> TYPE: PRT
<213> ORGANISM: Artificial Sequence
<220> FEATURE:
<223> OTHER INFORMATION: VL of mouse E1G5D1H1

<400> SEQUENCE: 23

Asp Ile Val Leu Thr Gln Ser Pro Ala Ser Leu Ala Val Ser Gln Gly
1               5                   10                  15

Gln Arg Ala Thr Ile Ser Cys Arg Ala Ser Glu Ser Val Asp Phe Tyr
            20                  25                  30

Gly Thr Ser Leu Met Gln Trp Phe Gln Leu Lys Pro Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asn Phe Ser Leu Asn Ile His
65                  70                  75                  80

Pro Val Glu Glu Asp Asp Ile Ala Met Tyr Phe Cys Gln Gln Ser Arg
                85                  90                  95

Lys Val Pro Trp Thr Phe Gly Gly Gly Thr Asn Leu Glu Ile Lys
            100                 105                 110


<210> SEQ ID NO 24
<211> LENGTH: 327
<212> TYPE: PRT
<213> ORGANISM: Artificial Sequence
<220> FEATURE:
<223> OTHER INFORMATION: Heavy chain constant region for chimeric and
      humanized antibodies

<400> SEQUENCE: 24

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
```

```
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 25
<211> LENGTH: 107
<212> TYPE: PRT
<213> ORGANISM: Artificial Sequence
<220> FEATURE:
<223> OTHER INFORMATION: Light chain constant region for chimeric and
      humanized antibodies

<400> SEQUENCE: 25

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 26
<211> LENGTH: 382
<212> TYPE: PRT
<213> ORGANISM: Artificial Sequence
<220> FEATURE:
<223> OTHER INFORMATION: Human PD1-Fc protein

<400> SEQUENCE: 26

Leu Asp Ser Pro Asp Arg Pro Trp Asn Pro Pro Thr Phe Ser Pro Ala
1               5                   10                  15

Leu Leu Val Val Thr Glu Gly Asp Asn Ala Thr Phe Thr Cys Ser Phe
            20                  25                  30
```

```
Ser Asn Thr Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Cys Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln Glu
    130                 135                 140

Asn Leu Tyr Phe Gln Gly Glu Pro Lys Ser Cys Asp Lys Thr His Thr
145                 150                 155                 160

Cys Pro Pro Cys Pro Ala Pro Glu Leu Leu Gly Gly Pro Ser Val Phe
                165                 170                 175

Leu Phe Pro Pro Lys Pro Lys Asp Thr Leu Met Ile Ser Arg Thr Pro
            180                 185                 190

Glu Val Thr Cys Val Val Val Asp Val Ser His Glu Asp Pro Glu Val
        195                 200                 205

Lys Phe Asn Trp Tyr Val Asp Gly Val Glu Val His Asn Ala Lys Thr
    210                 215                 220

Lys Pro Arg Glu Glu Gln Tyr Asn Ser Thr Tyr Arg Val Val Ser Val
225                 230                 235                 240

Leu Thr Val Leu His Gln Asp Trp Leu Asn Gly Lys Glu Tyr Lys Cys
                245                 250                 255

Lys Val Ser Asn Lys Ala Leu Pro Ala Pro Ile Glu Lys Thr Ile Ser
            260                 265                 270

Lys Ala Lys Gly Gln Pro Arg Glu Pro Gln Val Tyr Thr Leu Pro Pro
        275                 280                 285

Ser Arg Glu Glu Met Thr Lys Asn Gln Val Ser Leu Thr Cys Leu Val
    290                 295                 300

Lys Gly Phe Tyr Pro Ser Asp Ile Ala Val Glu Trp Glu Ser Asn Gly
305                 310                 315                 320

Gln Pro Glu Asn Asn Tyr Lys Thr Thr Pro Pro Val Leu Asp Ser Asp
                325                 330                 335

Gly Ser Phe Phe Leu Tyr Ser Lys Leu Thr Val Asp Lys Ser Arg Trp
            340                 345                 350

Gln Gln Gly Asn Val Phe Ser Cys Ser Val Met His Glu Ala Leu His
        355                 360                 365

Asn His Tyr Thr Gln Lys Ser Leu Ser Leu Ser Pro Gly Lys
    370                 375                 380
```

<210> SEQ ID NO 27
<211> LENGTH: 294
<212> TYPE: PRT
<213> ORGANISM: Artificial Sequence
<220> FEATURE:
<223> OTHER INFORMATION: Mouse PD-1-his

<400> SEQUENCE: 27

```
Met Trp Val Arg Gln Val Pro Trp Ser Phe Thr Trp Ala Val Leu Gln
1               5                   10                  15
```

```
Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Leu Ala Trp Ala Leu Ala Val
            180                 185                 190

Phe Cys Ser Thr Ser Met Ser Glu Ala Arg Gly Ala Gly Ser Lys Asp
        195                 200                 205

Asp Thr Leu Lys Glu Glu Pro Ser Ala Ala Pro Val Pro Ser Val Ala
    210                 215                 220

Tyr Glu Glu Leu Asp Phe Gln Gly Arg Glu Lys Thr Pro Glu Leu Pro
225                 230                 235                 240

Thr Ala Cys Val His Thr Glu Tyr Ala Thr Ile Val Phe Thr Glu Gly
                245                 250                 255

Leu Gly Ala Ser Ala Met Gly Arg Arg Gly Ser Ala Asp Gly Leu Gln
            260                 265                 270

Gly Pro Arg Pro Pro Arg His Glu Asp Gly His Cys Ser Trp Pro Leu
        275                 280                 285

His His His His His His
    290
```

<210> SEQ ID NO 28
<211> LENGTH: 453
<212> TYPE: PRT
<213> ORGANISM: Artificial Sequence
<220> FEATURE:
<223> OTHER INFORMATION: Human PDL1-Fc protein

<400> SEQUENCE: 28

```
Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80
```

```
Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Thr Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 29
<211> LENGTH: 151
<212> TYPE: PRT
<213> ORGANISM: Artificial Sequence
<220> FEATURE:

```
<223> OTHER INFORMATION: Human PD1-his

<400> SEQUENCE: 29

Leu Asp Ser Pro Asp Arg Pro Trp Asn Pro Pro Thr Phe Ser Pro Ala
1               5                   10                  15

Leu Leu Val Val Thr Glu Gly Asp Asn Ala Thr Phe Thr Cys Ser Phe
            20                  25                  30

Ser Asn Thr Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Cys Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln His
    130                 135                 140

His His His His His His His
145                 150


<210> SEQ ID NO 30
<211> LENGTH: 360
<212> TYPE: DNA
<213> ORGANISM: Artificial Sequence
<220> FEATURE:
<223> OTHER INFORMATION: VH of mouse E1A9C8A7

<400> SEQUENCE: 30

caggtccagc tgcagcagtc tggggctgag gtggtgaggc ctggggtctc agtgaggatt      60

tcctgcaagg gttctggcta cacattctct gattatgtta tgcactggat gaagcagagt     120

catggagaga gcctagagtg gattggggtt atcagtactt accatattcc tgctgtctac     180

aaccagaagt tcaagggcaa ggccacaatg actgtagaca aatcctccag tacagtctat     240

ctggaacttg ccagactgac atctgaggat tctgccatct attactgtgc aagagaggtc     300

tatggtgact cttactactt cgatgtctgg ggcgcgggga ccacggtcac cgtctcctca     360


<210> SEQ ID NO 31
<211> LENGTH: 361
<212> TYPE: DNA
<213> ORGANISM: Artificial Sequence
<220> FEATURE:
<223> OTHER INFORMATION: VH of chimeric E1A9C8A7

<400> SEQUENCE: 31

caagtgcagc tgcagcagag cggcgccgaa gtggtgagac ccggcgtgag cgtgaggatc      60

agctgcaagg gcagcggcta taccttcagc gactacgtga tgcactggat gaagcagagc     120

cacggcgagt ctctggagtg gatcggagtg atcagcacct accacatccc cgccgtgtac     180

aaccagaagt tcaagggcaa ggccaccatg accgtggaca agagcagcag caccgtgtat     240

ctggagctgg ctagactgac ctccgaggat agcgccatct actactgcgc cagagaggtg     300

tacggcgata gctactactt cgacgtgtgg ggcgccggaa ccacagtgac cgtgagcagc     360

g                                                                     361
```

<210> SEQ ID NO 32
<211> LENGTH: 360
<212> TYPE: DNA
<213> ORGANISM: Artificial Sequence
<220> FEATURE:
<223> OTHER INFORMATION: VH of huE1A9C8A7-V8

<400> SEQUENCE: 32
caagtgcagc tggtgcagag cggagccgaa gtggtgaaac ccggcgccag cgtgaagatc 60
agctgcaagg ccagcggcta caccttcacc gactacgtga tgcactgggt gagacaagcc 120
cccggccagt ctctggagtg gatgggcgtg atcagcacct accacatccc cgccgtgtac 180
aaccagaagt tcaagggcaa ggccaccatg accgtggaca ccagcaccag caccgtgtat 240
ctggagctgt cctctctgag gagcgaggac accgccgtgt actactgcgc cagagaggtg 300
tacggcgaca gctactactt cgacgtgtgg ggccaaggca ccacagtgac cgtgagcagc 360

<210> SEQ ID NO 33
<211> LENGTH: 336
<212> TYPE: DNA
<213> ORGANISM: Artificial Sequence
<220> FEATURE:
<223> OTHER INFORMATION: VL of mouse E1A9C8A7

<400> SEQUENCE: 33
gatgttttga tgacccaaat tccactctcc ctgcctgtta gtcttggaga tcaagtctcc 60
atctcttgca gatctagtca gagcattgta catagtaatg gaaacaccta tttagaatgg 120
tacctgcaga aaccaggcca gtctccaaag ctcctgatct acaaagtttc caaccgattt 180
tctggggtcc cagacaggtt cagtggcagt ggatcaggga cagatttcac actcaagatc 240
agcagagtgg aggctgagga tctgggagtt tattactgct ttcaaggttc acatgttccg 300
tacacgttcg gaggggggac caagctggaa ataaaa 336

<210> SEQ ID NO 34
<211> LENGTH: 336
<212> TYPE: DNA
<213> ORGANISM: Artificial Sequence
<220> FEATURE:
<223> OTHER INFORMATION: VL of chimeric E1A9C8A7

<400> SEQUENCE: 34
gacgtgctga tgacccagat ccctctgtct ctgcccgtgt ctctgggaga tcaagtgagc 60
atcagctgca gatccagcca gagcatcgtg cacagcaacg gcaacaccta tctggagtgg 120
tatctgcaga agcccggcca gagccccaag ctgctgatct acaaggtctc caatagattc 180
tccggcgtgc ccgatagatt cagcggaagc ggcagcggca ccgacttcac actgaagatc 240
tccagagtgg aggccgagga tctgggcgtg tactactgct ttcaaggcag ccacgtgccc 300
tacacctttg gcggcggcac caaactggag atcaag 336

<210> SEQ ID NO 35
<211> LENGTH: 336
<212> TYPE: DNA
<213> ORGANISM: Artificial Sequence
<220> FEATURE:
<223> OTHER INFORMATION: VL of huE1A9C8A7-V1 - huE1A9C8A7-V11

<400> SEQUENCE: 35
gacatcgtga tgacccagac acctctgtct ctgcccgtga cacccggcga gcccgccagc 60

```
atcagctgca gaagcagcca gagcatcgtg cacagcaacg gcaacaccta tctggagtgg    120

tatctgcaga agcccggcca gagccctcag ctgctgatct acaaggtgtc caatagattc    180

agcggcgtgc ccgacagatt cagcggcagc ggaagcggca cagacttcac actgaagatc    240

tccagagtgg aggccgagga cgtgggcgtg tactactgct tccaaggcag ccacgtgcct    300

tacaccttcg gcggcggcac caaggtggag atcaag                              336


<210> SEQ ID NO 36
<211> LENGTH: 360
<212> TYPE: DNA
<213> ORGANISM: Artificial Sequence
<220> FEATURE:
<223> OTHER INFORMATION: VH of mouse E2G4E10B7

<400> SEQUENCE: 36

caggtccagc tgcagcagtc tggggctgag ctggtgaggc ctggggtctc agtgaagatt     60

tcctgcaagg gttctggcta cacattcact gattatgtta tgcactgggt gaggcagagc    120

catgcaaaga gtctagagtg gattggagtt atcagtactc actttggtga tggtgtttac    180

aaccagaagt tcaagggcaa ggccacaatg actgtagaca aatcctccag cacagcctat    240

atggaacttg ccagactgac atctgaggat tctgccatct attactgtgc aagagaggtc    300

tatggtgact cttggtactt cgatgtctgg ggcgcaggga ccacggtcac cgtctcctca    360


<210> SEQ ID NO 37
<211> LENGTH: 336
<212> TYPE: DNA
<213> ORGANISM: Artificial Sequence
<220> FEATURE:
<223> OTHER INFORMATION: VL of mouse E2G4E10B7

<400> SEQUENCE: 37

gatgttttga tgacccaaac tccactctcc ctgcctgtca gtcttggaga tcaagcctcc     60

atctcttgca gatctagtca gagccttgta catagtgatg gaaacaccta tttagaatgg    120

tacctgcaga aaccaggcca gtctccaaag ctcctgatct acaaagtttc caaccgattt    180

tctggggtcc cagacaggtt cagtggcagt ggatcaggga cagatttcac actcaagatc    240

agcagactgg aggctgagga tctgggagtt tattactgct ttcaaggttc acatgttccg    300

tacacgttcg gaggggggac caagctggaa ataaaa                              336


<210> SEQ ID NO 38
<211> LENGTH: 363
<212> TYPE: DNA
<213> ORGANISM: Artificial Sequence
<220> FEATURE:
<223> OTHER INFORMATION: VH of mouse E1G5D1H1

<400> SEQUENCE: 38

gaagtgcagt tggtggagtc tgggggaggc ttagtgaagc ctggagggtc tctgaagctc     60

tcctgtgcag cctctggatt cactttcagt gacttttaca tgtattgggt tcgccagact    120

ccggaaaaga ggctggagtg ggtcgcaacc attagtaata gtggtactca aacctactat    180

ctagacagtg tgaaggggcg attcaccatc tccagagaca atgccaagaa taacctgtac    240

ctgcaaatga gcagtctgaa gtctgaggac acagccatgt actattgtgc tagagactac    300

tataggtacg acagctggta cttcgatgtc tggggcgcag ggaccacggt caccgtctcc    360

tca                                                                  363
```

<210> SEQ ID NO 39
<211> LENGTH: 333
<212> TYPE: DNA
<213> ORGANISM: Artificial Sequence
<220> FEATURE:
<223> OTHER INFORMATION: VL of mouse E1G5D1H1

<400> SEQUENCE: 39
gacattgtat taacccaatc tccagcttct ttggctgtgt ctcaagggca gagagccacc 60
atctcctgca gagccagtga aagtgttgat ttttatggca caagtttaat gcagtggttc 120
caactgaaac caggacagcc acccaaactc ctcatctatg ctgcatccaa cgtcgaatct 180
ggagtccctg ccaggtttag tggcagtggg tctgggacaa acttcagcct caacatccat 240
cctgtggagg aggatgatat tgccatgtat ttctgtcagc aaagtaggaa ggttccgtgg 300
acattcggtg gaggcaccaa ccttgaaatc aaa 333

<210> SEQ ID NO 40
<211> LENGTH: 984
<212> TYPE: DNA
<213> ORGANISM: Artificial Sequence
<220> FEATURE:
<223> OTHER INFORMATION: Heavy chain constant region for chimeric and humanized antibodies

<400> SEQUENCE: 40
gccagcacaa agggcccttc cgtgtttccc ctggccccct gcagcaggag cacctctgag 60
tccaccgccg ccctgggctg tctggtgaag gactactttc ccgagcccgt gaccgtgagc 120
tggaattccg gcgccctgac atccggcgtg cacaccttcc ccgccgtgct gcagtcctcc 180
ggcctgtaca gcctgagctc cgtggtgaca gtgccttcct cctccctggg caccaagacc 240
tacacatgta atgtggatca caagcccagc aacacaaagg tggataagag agtggagtcc 300
aagtacggcc ctccttgccc tccctgtcct gccccagagt tcctgggcgg cccctctgtg 360
ttcctgttcc cccctaagcc caaggacaca ctgatgatct ccaggacccc tgaggtgacc 420
tgcgtggtgg tggacgtgag ccaggaggac cctgaggtgc agttcaattg gtacgtggat 480
ggcgtggagg tgcacaatgc caagacaaag cccagagagg agcagtttaa ttccacatac 540
agggtggtgt ccgtgctgac cgtgctgcac caggattggc tgaacggcaa ggagtacaag 600
tgtaaggtga gcaacaaggg cctgccttcc tccatcgaga agacaatcag caaggccaag 660
ggccagccta gggagcccca ggtgtacaca ctgcctccca gccaggagga gatgaccaag 720
aaccaggtga gcctgacctg cctggtgaag ggcttctacc ctagcgacat cgccgtggag 780
tgggagtcca acggccagcc cgagaataac tacaagacaa caccccccgt gctggattcc 840
gatggcagct tctttctgta ctccaggctg accgtggata agagcaggtg gcaggagggc 900
aatgtgttca gctgctccgt gatgcacgag gccctgcaca atcactacac ccagaagagc 960
ctgtccctga gcctgggcaa gtga 984

<210> SEQ ID NO 41
<211> LENGTH: 324
<212> TYPE: DNA
<213> ORGANISM: Artificial Sequence
<220> FEATURE:
<223> OTHER INFORMATION: Light chain constant region for chimeric and humanized antibodies

<400> SEQUENCE: 41
cgtacggtgg ctgcaccatc tgtcttcatc ttcccgccat ctgatgagca gttgaaatct 60

-continued

```
ggaactgcct ctgttgtgtg cctgctgaat aacttctatc ccagagaggc caaagtacag    120

tggaaggtgg ataacgccct ccaatcgggt aactcccagg agagtgtcac agagcaggac    180

agcaaggaca gcacctacag cctcagcagc accctgacgc tgagcaaagc agactacgag    240

aaacacaaag tctacgcctg cgaagtcacc catcagggcc tgagctcgcc cgtcacaaag    300

agcttcaaca ggggagagtg ttag                                           324


<210> SEQ ID NO 42
<211> LENGTH: 120
<212> TYPE: PRT
<213> ORGANISM: Artificial Sequence
<220> FEATURE:
<223> OTHER INFORMATION: VH of huE1A9C8A7-V8-3

<400> SEQUENCE: 42

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Val Met His Trp Val Arg Gln Ala Pro Gly Gln Ser Leu Glu Trp Met
        35                  40                  45

Gly Val Ile Ser Thr Tyr His Ile Pro Ala Val Tyr Asn Gln Lys Phe
    50                  55                  60

Lys Gly Lys Ala Thr Met Thr Val Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Glu Val Tyr Gly Glu Ser Tyr Tyr Phe Asp Val Trp Gly Gln
            100                 105                 110

Gly Thr Thr Val Thr Val Ser Ser
        115                 120
```

MONOCLONAL ANTIBODIES WHICH BIND PD-1, ENCODING NUCLEOTIDES THEREOF AND METHOD OF USE THEREOF TO TREAT CANCER, INFECTIOUS DISEASE AND INFLAMMATORY DISEASE

RELATED APPLICATIONS AND INCORPORATION BY REFERENCE

This application claims priority to U.S. Patent Application No. 63/072,421 filed on Aug. 31, 2020.

All documents cited or referenced herein (including without limitation all literature documents, patents, published patent applications cited herein) ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference. Any Genbank sequences mentioned in this disclosure are incorporated by reference with the Genbank sequence to be that of the earliest effective filing date of this disclosure.

SEQUENCE STATEMENT

The instant application contains a Sequence Listing which has been submitted electronically and is hereby incorporated by reference in its entirety. Said ASCII copy was created Aug. 30, 2021, is named 55532_00094SL.txt and is 40,427 bytes in size.

FIELD OF THE INVENTION

The present disclosure relates generally to an isolated monoclonal antibody, particularly a mouse, chimeric or humanized monoclonal antibody, or an antigen-binding portion thereof, that binds to PD-1, with high affinity and functionality. A nucleic acid molecule encoding the antibody or the antigen-binding portion thereof, an expression vector, a host cell and a method for expressing the antibody or the antigen-binding portion thereof are also provided. The present disclosure further provides a bispecific molecule, an immunoconjugate, a chimeric antigen receptor, and a pharmaceutical composition which may comprise the antibody or the antigen-binding portion thereof, as well as a treatment method using the anti-PD-1 antibody or the antigen-binding portion thereof of the disclosure.

BACKGROUND OF THE INVENTION

The immune system inflicts damages on harmful invaders while sparing healthy cells. Such balance of immunological defense and self-tolerance is critical to normal physiological function, and is accomplished through multiple checks and balances on immune responses. For example, effector immune cells cannot exert full functions until they pass the immune checkpoints. Cytotoxic T lymphocyte antigen 4 (CTLA4) and programmed cell death protein 1 (PD-1) are the first two discovered immune checkpoint inhibitory receptors, serving as brakes for the immune response and providing immunosuppressive signals. CTLA4 is induced early during T cell activation process, and competes with CD28 for CD80/CD86 binding. PD-1 is expressed later and engages programmed cell death 1 ligand 1 (PD-L1) and/or PD-L2 to counter TCR/CD28 induced positive signals (Sharpe A H, Pauken K E. (2018) *Nat Rev Immunol.* 18(3):153-167).

PD-1 is a transmembrane protein, containing a membrane proximal immunoreceptor tyrosine inhibitory motif (ITIM) and a membrane distal tyrosine-based switch motif (ITSM) (Thomas, M. L. (1995) *J Exp Med* 181:1953-6; Vivier, E and Daeron, M (1997) *Immunol Today* 18:286-91). Upon PD-L1 binding, PD-1 activation results in ITSM phosphorylation, leading to recruitment of Src homology region 2 domain containing phosphatase 1/2 and slam-associated protein, de-phosphorylation of TCR and CD28 proximal signaling molecules such as ZAP70, and inactivation of downstream signaling pathways such as PI3K/AKT and Ras-MEK-ERK pathways (Sharpe A H, Pauken K E. (2018) supra; Yokosuka T et al., (2012) *J Exp Med.* 209(6):1201-17). The PD-1-PD-L1 signaling, depending on contexts, induces effector T cell apoptosis, anergy and exhaustion, innate lymphoid cell proliferation and function, and/or Treg cell proliferation (Qin W et al., (2019) *Front Immunol.* 10:2298).

PD-L1 and PD-L2 expressions on hematopoietic cells and non-hematopoietic tissues can prevent tissue inflammation and contribute to homeostasis maintenance, while PD-L1 and/or PD-L2 expressions on cancer cells help cancer cells evade immune surveillance. Specifically, the binding of PD-L1 on the tumor cells to PD-1 on cytotoxic T cells results in anergy and apoptosis of $CD8^+$ T cells, and PD-L1 renders tumor cells resistant to the lysis by $CD8^+$ T cells (Azuma T et al., (2008) *Blood* 111(7):3635-3643). Several PD-1 or PD-L1 inhibitors have been approved by FDA for cancer treatment, including two anti-PD-1 antibodies, nivolumab and pembrolizumab, and three anti-PD-L1 antibodies, avelumab, atezolizumab, and durvalumab. OPDIVO® nivolumab (Bristol Myers Squibb) has been approved for treatment of non-small-cell lung cancer (NSCLC), renal cell carcinoma (RCC), bladder cancer (BC), colorectal cancer (CRC) with microsatellite instability or mismatch repair deficiency (MSIH/dMMR), hepatocellular carcinoma (HCC), classic Hodgkin lymphoma (cHL), melanoma, and head and neck squamous cell carcinoma (HNSCC). KEYTRUDA® pembrolizumab (Merck) has been approved for melanoma, HNSCC, cervical cancer, cHL, NSCLC, BC, stomach and gastroesophageal cancers, and all advanced solid tumors with MSI-H/dMMR. A meta-analysis on 19 randomized clinical trials involving 11379 patients suggested that the survival outcomes in anti-PD-1 therapies are significantly better than anti-PD-L1 therapies (Duan J et al., (2020) *JAMA Oncol.* 6(3):375-384).

High PD-1 expression was also found on $CD8^+$ T cells in human immunodeficiency virus (HIV), simian immunodeficiency virus (SIV), hepatitis B virus (HBV) and hepatitis C virus (HCV) infections. PD-1/PD-L1 blockade can restore $CD8^+$ T cells and $CD4^+$ T cells' function, abolish liver-resident NK cells' suppressive effect on T cells, promote cytokine production, and reduce viral load (Barber D L et al., (2006) *Nature.* 439:682-687; Qin W et al., (2019) supra). The anti-PD-1 and/or anti-PD-L1 therapies have shown beneficial effects on sepsis, and nivolumab and BMS-936559 are in clinical trials for treatment of severe sepsis (Riva A, Chokshi S. (2018) *Hepatol Int.* 12(3):223-36).

In clinical use, some patients do not respond to the currently approved anti-PD-1 antibodies. Therefore, there is a need for additional monoclonal antibodies with enhanced pharmaceutical characteristics.

Citation or identification of any document in this application is not an admission that such document is available as prior art to the present invention.

SUMMARY OF THE INVENTION

The present disclosure provides an isolated monoclonal antibody, for example, a mouse, chimeric or humanized monoclonal antibody, or an antigen-binding portion thereof, that binds to PD-1 (e.g., the human PD-1) and has i) comparable, if not higher, binding affinity/capability to human, monkey and mouse PD-1, ii) comparable, if not higher, blocking activity on PD-1-PD-L1 interaction, and/or iii) comparable, if not better, in vivo anti-tumor activity, as compared to prior art anti-PD-1 antibodies such as nivolumab and pembrolizumab.

The antibody or antigen-binding portion of the disclosure can be used for a variety of applications, including detection of human, monkey or mouse PD-1 proteins in vitro, and treatment of diseases associated with PD-1 signaling, such as cancers, infectious diseases, and inflammatory diseases.

Accordingly, in one aspect, the disclosure pertains to an isolated monoclonal antibody, or an antigen-binding portion thereof, that binds PD-1, having (i) a heavy chain variable region that may comprise a VH CDR1 region, a VH CDR2 region and a VH CDR3 region, wherein the VH CDR1 region, the VH CDR2 region and the VH CDR3 region may comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 1, 3 and 6 (X1=D, X2=Y), respectively; (2) SEQ ID NOs: 1, 3 and 6 (X1=E, X2=Y), respectively; (3) SEQ ID NOs: 1, 4 and 6 (X1=D, X2=W), respectively; or (4) SEQ ID NOs: 2, 5 and 7, respectively; and/or (ii) a light chain variable region that may comprise a VL CDR1 region, a VL CDR2 region and a VL CDR3 region, wherein the VL CDR1 region, the VL CDR2 region and the VL CDR3 region may comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 8 (X1=I, X2=N), 10 and 12, respectively; (2) SEQ ID NOs: 8 (X1=I, X2=A), 10 and 12, respectively; (3) SEQ ID NOs: 8 (X1=L, X2=D), 10 and 12, respectively; or (4) SEQ ID NOs: 9, 11 and 13, respectively.

The isolated monoclonal antibody, or the antigen-binding portion thereof, of the present disclosure may comprise a heavy chain variable region having a VH CDR1 region, a VH CDR2 region and a VH CDR3 region, and a light chain variable region having a VL CDR1 region, a VL CDR2 region and a VL CDR3 region, wherein the VH CDR1, VH CDR2, VH CDR3, VL CDR1, VL CDR2 and VL CDR3 may comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 1, 3, 6 (X1=D, X2=Y), 8 (X1=I, X2=N), 10 and 12, respectively; (2) SEQ ID NOs: 1, 3, 6 (X1=E, X2=Y), 8 (X1=I, X2=A), 10 and 12, respectively; (3) SEQ ID NOs: 1, 4, 6 (X1=D, X2=W), 8 (X1=L, X2=D), 10 and 12, respectively; or (4) SEQ ID NOs: 2, 5, 7, 9, 11 and 13, respectively.

The heavy chain variable region may comprise an amino acid sequence having at least 85%, 86%, 87%, 88%, 89%, 90%, 91%, 92%, 93%, 94%, 95%, 96%, 97%, 98%, 99% or 100% identity to SEQ ID NOs: 14, 15 (X1=S, X2=M, X3=K; X1=T, X2=M, X3=K; X1=S, X2=V, X3=K; X1=S, X2=M, X3=T; X1=T, X2=V, X3=T), 16 (X1=V, X2=S, X3=I; X1=I, X2=G, X3=I; X1=I, X2=S, X3=M), 17 (X1=R, X2=A, X3=V; X1=K, X2=V, X3=V; X1=K, X2=A, X3=R), 18, 19 or 42. The amino acid sequence of SEQ ID NO: 14 may be encoded by the nucleotide sequences of SEQ ID NOs: 30 or 31. The amino acid sequences of SEQ ID NOs: 16 (X1=I, X2=S, X3=M), 18 and 19 may be encoded by the nucleotide sequences of SEQ ID NOs: 32, 36 and 38, respectively.

The light chain variable region may comprise an amino acid sequence having at least 85%, 86%, 87%, 88%, 89%, 90%, 91%, 92%, 93%, 94%, 95%, 96%, 97%, 98%, 99% or 100% identity to SEQ ID NOs: 20, 21 (X1=N; X1=A), 22 or 23. The amino acid sequence of SEQ ID NO: 20 may be encoded by the nucleotide sequences of SEQ ID NOs: 33 or 34. The amino acid sequences of SEQ ID NOs: 21 (X1=N), 22 and 23 may be encoded by the nucleotide sequences of SEQ ID NOs: 35, 37 and 39, respectively.

The isolated monoclonal antibody, or the antigen-binding portion thereof, of the present disclosure may comprise a heavy chain variable region and a light chain variable region, the heavy chain variable region and the light chain variable region may comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 14 and 20, respectively; (2) SEQ ID NOs: 15 (X1=S, X2=M, X3=K) and 21 (X1=N), respectively; (3) SEQ ID NOs: 15 (X1=T, X2=M, X3=K) and 21 (X1=N), respectively; (4) SEQ ID NOs: 15 (X1=S, X2=V, X3=K) and 21 (X1=N), respectively; (5) SEQ ID NOs: 15 (X1=S, X2=M, X3=T) and 21 (X1=N), respectively; (6) SEQ ID NOs: 15 (X1=T, X2=V, X3=T) and 21 (X1=N), respectively; (7) SEQ ID NOs: 16 (X1=V, X2=S, X3=I) and 21 (X1=N), respectively; (8) SEQ ID NOs: 16 (X1=I, X2=G, X3=I) and 21 (X1=N), respectively; (9) SEQ ID NOs: 16 (X1=I, X2=S, X3=M) and 21 (X1=N), respectively; (10) SEQ ID NOs: 17 (X1=R, X2=A, X3=V) and 21 (X1=N), respectively; (11) SEQ ID NOs: 17 (X1=K, X2=V, X3=V) and 21 (X1=N), respectively; (12) SEQ ID NOs: 17 (X1=K, X2=A, X3=R) and 21 (X1=N), respectively; (13) SEQ ID NOs: 42 and 21 (X1=A), respectively; (14) SEQ ID NOs: 18 and 22, respectively; or (15) SEQ ID NOs: 19 and 23, respectively.

The isolated monoclonal antibody, or the antigen-binding portion thereof, of the present disclosure may comprise a heavy chain and a light chain linked by disulfide bonds, the heavy chain may comprise a heavy chain variable region and a heavy chain constant region, the light chain may comprise a light chain variable region and a light chain constant region, wherein the C terminus of the heavy chain variable region is linked to the N terminus of the heavy chain constant region, and the C terminus of the light chain variable region is linked to the N terminus of the light chain constant region, wherein the heavy chain variable region and the light chain variable region may comprise amino acid sequences described above.

The heavy chain constant region may be with reduced FcR binding affinity, such as genetically engineered human IgG1 or IgG2 constant region, or human IgG4 constant region having the amino acid sequence set forth in e.g., SEQ ID NO.: 24, or a functional fragment thereof. The heavy chain constant region may also be IgG1 constant region, with normal or even enhanced FcR binding affinity. The light chain constant region may be human kappa constant region having the amino acid sequences set forth in e.g., SEQ ID NO.: 25. The amino acid sequences of SEQ ID NOs: 24 and 25 may be encoded by the nucleotide sequences of SEQ ID NOs: 40 and 41, respectively.

The antibody of the present disclosure in certain embodiments may comprise or consist of two heavy chains and two light chains, wherein each heavy chain may comprise the heavy chain constant region, heavy chain variable region or CDR sequences mentioned above, and each light chain may comprise the light chain constant region, light chain variable region or CDR sequences mentioned above. The antibody or the antigen-binding portion thereof of the present disclosure in other embodiments may be a single chain variable fragment (scFv) antibody, or antibody fragments, such as Fab or F(ab')2 fragments.

The disclosure also provides a bispecific molecule that may comprise the antibody, or the antigen-binding portion thereof, of the disclosure, linked to a second functional moiety (e.g., a second antibody) having a different binding specificity than said antibody, or antigen-binding portion thereof. The disclosure also provides an immunoconjugate, such as an antibody-drug conjugate, that may comprise an antibody, or antigen-binding portion thereof, of the disclosure, linked to a therapeutic agent, such as a cytotoxin. In another aspect, the antibody or the antigen binding portion thereof of the present disclosure can be made into part of a chimeric antigen receptor (CAR). Also provided is an immune cell that may comprise the antigen chimeric receptor, such as a T cell and a NK cell. The antibody or antigen binding portion thereof of the disclosure can also be encoded by or used in conjunction with an oncolytic virus.

The disclosure further provides a nucleic acid molecule encoding the antibody or antigen-binding portion thereof of the disclosure, as well as an expression vector comprising such a nucleic acid molecule and a host cell comprising such an expression vector. A method for preparing the anti-PD-1 antibody or antigen binding portion thereof using the host cell of the disclosure is provided, comprising steps of (i) expressing the antibody or antigen binding portion thereof in the host cell, and (ii) isolating the antibody or antigen binding portion thereof from the host cell or its cell culture.

The disclosure provides a composition comprising the antibody or antigen binding portion thereof, the immuneconjugate, the bispecific molecule, the immune cell, the oncolytic virus, the nucleic acid molecule, the expression vector, or the host cell of the disclosure, and a pharmaceutically acceptable carrier. In certain embodiments, the pharmaceutical composition may further contain a therapeutic agent for treating a specific disease, such as an anti-tumor agent, an anti-infectious agent, or an anti-inflammatory agent.

In yet another aspect, the disclosure provides a method for treating a disease associated with PD-1 signaling, which may comprise administering to a subject a therapeutically effective amount of the composition of the present disclosure.

The disease may be tumor or cancer. The tumor or cancer includes, but not limited to, non-small-cell lung cancer (NSCLC), renal cell carcinoma (RCC), bladder cancer (BC), colorectal cancer (CRC) with microsatellite instability or mismatch repair deficiency (MSI-H/dMMR), hepatocellular carcinoma (HCC), classic Hodgkin lymphoma (cHL), melanoma, head and neck squamous cell carcinoma (HNSCC), cervical cancer, stomach cancer, gastroesophageal cancer, colon adenocarcinoma, and all advanced solid tumors with MSI-H/dMMR. The composition may comprise the antibody, or the antigen-binding portion thereof, with weak FcR binding heavy chain constant regions, the bispecific molecule, the nucleic acid molecule, or the expression vector of the disclosure. In some embodiments, at least one additional anti-cancer antibody can be further administered, such as an anti-VISTA antibody, an anti-PD-L1 antibody, an anti-LAG-3 antibody and/or an anti-CTLA-4 antibody. In yet another embodiment, an antibody, or an antigen-binding portion thereof, of the disclosure is administered with a cytokine (e.g., IL-2 and/or IL-21), or a costimulatory antibody (e.g., an anti-CD137 and/or anti-GITR antibody). In another embodiment, an antibody, or an antigen-binding portion thereof, of the disclosure is administered with a chemotherapeutic agent, which may be a cytotoxic agent, such as epirubicin, oxaliplatin, and/or 5-fluorouracil (5-FU). The antibody or antigen binding portion of the present disclosure may be, for example, mouse, chimeric or humanized. In certain embodiments, the subject is human.

The disease may be an infectious disease, including, but not limited to those caused by viruses, bacteria, or fungi. In certain embodiments, the infectious disease is sepsis, HIV infection, simian immunodeficiency virus infection, HBV infection, or HCV infection. The composition comprises the antibody, or the antigen-binding portion thereof, with weak FcR binding heavy chain constant regions, the bispecific molecule, the nucleic acid molecule, or the expression vector of the disclosure. In certain embodiments, the subject is further administered with an anti-infectious agent, such as an anti-viral agent, an anti-bacterial agent, or an anti-fungal agent. The antibody or antigen binding portion thereof of the present disclosure may be, for example, mouse, chimeric or humanized. In certain embodiments, the subject is human.

The disease may be an inflammatory disease. The inflammatory disease includes, but not limited to, rheumatoid arthritis, colitis, lupus-like nephritis, systemic lupus erythematosus, and psoriasis. The composition of the disclosure comprises the antibody, or the antigen-binding portion thereof, with high FcR binding heavy chain constant regions, the immunoconjugate, the bispecific molecule, the immune cell with CAR, the nucleic acid molecule, or the expression vector of the disclosure. In certain embodiments, the composition of the disclosure is administered via local delivery to the inflammatory tissues. The antibodies of the present disclosure can be, for example, mouse, chimeric or humanized antibodies. In certain embodiments, the subject is human.

In yet another aspect, the disclosure provides a method for modulating or enhancing an immune response in a subject in need thereof, comprising administering to the subject the composition of the disclosure such that the immune response in the subject is modulated/enhanced. The composition comprises the antibody, or the antigen-binding portion thereof, with weak FcR binding heavy chain constant regions, the bispecific molecule, the nucleic acid molecule, or the expression vector of the disclosure. The antibody or antigen binding portion thereof of the present disclosure may be, for example, mouse, chimeric or humanized. In certain embodiments, the subject is human.

Other features and advantages of the instant disclosure will be apparent from the following detailed description and examples, which should not be construed as limiting. The contents of all references, Genbank entries, patents and published patent applications cited throughout this application are expressly incorporated herein by reference.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1A:
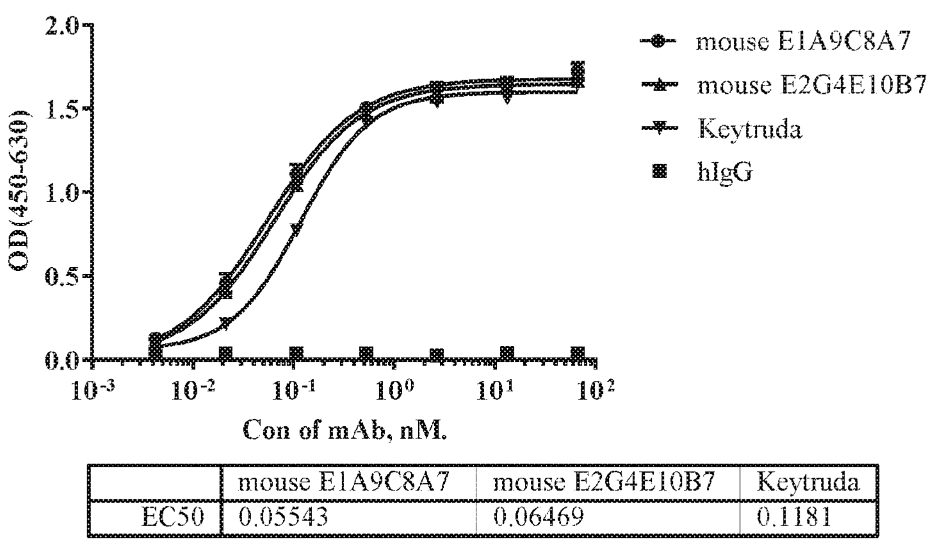
FIGS. 1A-1B show the binding capabilities of mouse antibodies E1A9C8A7 and E2G4E10B7 (A), and E1G5D1H1 (B) to human PD-1 in a capture ELISA.

To ensure that the present disclosure may be more readily understood, certain terms are first defined. Additional definitions are set forth throughout the detailed description.

The term "PD-1" or "PD1" refers to programmed cell death protein 1, also known as CD279. The term "PD-1" may comprise variants, isoforms, homologs, orthologs and paralogs. For example, an antibody specific for a human PD-1 protein may, in certain cases, cross-react with a PD-1 protein from a species other than human, such as monkey. In other embodiments, an antibody specific for a human PD-1 protein may be completely specific for the human PD-1 protein and exhibit no cross-reactivity to other species or of other types, or may cross-react with PD-1 from certain other species but not all other species.

The term "human PD-1" refers to a PD-1 protein having an amino acid sequence from a human, such as the amino acid sequence of human PD-1 having a NCBI Reference number of NP_005009.2 (Orth M F et al., (2020), *Cancer Immunol. Immunother.* 69 (7): 1353-1362). The terms "monkey PD-1" or "cynomolgus PD-1" refer to a PD-1 protein having an amino acid sequence from monkeys, such as the amino acid sequence having a NCBI Reference number of XP_001107830.1 (McGary C S et al., (2017), *Immunity* 47 (4): 776-788). The term "mouse PD-1" refers to a PD-1 protein having an amino acid sequence from a mouse, such as the amino acid sequence of mouse PD-1 having a NCBI Reference number of NP_032824.1 (Lai X et al., (2020) *PLoS ONE* 15(4): e0231499).

The term "antibody" as used herein refers to an immunoglobulin molecule that recognizes and specifically binds a target, such as PD-1, through at least one antigen-binding site wherein the antigen-binding site is usually within the variable region of the immunoglobulin molecule. As used herein, the term encompasses intact polyclonal antibodies, intact monoclonal antibodies, single-chain Fv (scFv) antibodies, heavy chain antibodies (HCAbs), light chain antibodies (LCAbs), multispecific antibodies, bispecific antibodies, monospecific antibodies, monovalent antibodies, fusion proteins comprising an antigen-binding site of an antibody, and any other modified immunoglobulin molecule comprising an antigen-binding site (e.g., dual variable domain immunoglobulin molecules) as long as the antibodies exhibit the desired biological activity. Antibodies also include, but are not limited to, mouse antibodies, chimeric antibodies, humanized antibodies, and human antibodies. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well-known subunit structures and three-dimensional configurations. Antibodies can be naked or conjugated to other molecules, including but not limited to, toxins and radioisotopes. Unless expressly indicated otherwise, the term "antibody" as used herein include "antigen-binding portion" of the intact antibodies. An IgG is a glycoprotein which may comprise two heavy (H) chains and two light (L) chains inter-connected by disulfide bonds. Each heavy chain may be comprised of a heavy chain variable region (abbreviated herein as VH) and a heavy chain constant region. The heavy chain constant region may be comprised of three domains, CH1, CH2 and CH3. Each light chain may be comprised of a light chain variable region (abbreviated herein as VL) and a light chain constant region. The light chain constant region may be comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., a PD-1 protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment which may comprise two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; (vi) an isolated complementarity determining region (CDR); and (viii) a nanobody, a heavy chain variable region containing a single variable domain and two constant domains. Furthermore, although the two domains of the Fv fragment, VL and VH, are coded by separate genes, they can be joined, using recombinant methods, by a synthetic linker that enables them to be made as a single protein chain in which the VL and VH regions pair to form monovalent molecules (known as single chain Fv (scFv); see e.g., Bird et al., (1988) Science 242:423-426; and Huston et al., (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds a PD-1 protein is substantially free of antibodies that specifically bind antigens other than PD-1 proteins). An isolated antibody that specifically binds a human PD-1 protein may, however, have cross-reactivity to other antigens, such as PD-1 proteins from other species. Moreover, an isolated antibody can be substantially free of other cellular material and/or chemicals.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method.

The term "mouse antibody", as used herein, is intended to include antibodies having variable regions in which both the framework and CDR regions are derived from mouse germline immunoglobulin sequences. Furthermore, if the antibody contains a constant region, the constant region also is derived from mouse germline immunoglobulin sequences. The mouse antibodies of the disclosure can include amino acid residues not encoded by mouse germline immunoglobulin sequences (e.g., mutations introduced by random or site-specific mutagenesis in vitro or by somatic mutation in vivo). However, the term "mouse antibody", as used herein, is not intended to include antibodies in which CDR sequences derived from the germline of another mammalian species have been grafted onto mouse framework sequences.

The term "chimeric antibody" refers to an antibody made by combining genetic material from a nonhuman source with genetic material from a human being. Or more generally, a chimeric antibody is an antibody having genetic material from a certain species with genetic material from another species.

The term "humanized antibody", as used herein, refers to an antibody from non-human species whose protein sequences have been modified to increase similarity to antibody variants produced naturally in humans.

The term "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

As used herein, an antibody that "specifically binds to human PD-i" is intended to refer to an antibody that binds to human PD-1 protein (and possibly a PD-1 protein from one or more non-human species) but does not substantially bind to non-PD-1 proteins. Preferably, the antibody binds to human PD-1 protein with "high affinity", namely with a $K_D$ of $5.0\times10^{-8}$ M or less, more preferably $1.0\times10^{-8}$ M or less, and more preferably $5.0\times10^{-9}$ M or less.

The term "does not substantially bind" to a protein or cells, as used herein, means does not bind or does not bind with a high affinity to the protein or cells, i.e. binds to the protein or cells with a $K_D$ of $1.0\times10^{-6}$ M or more, more preferably $1.0\times10^{-5}$ M or more, more preferably $1.0\times10^{-4}$ M or more, more preferably $1.0\times10^{-3}$ M or more, even more preferably $1.0\times10^{-2}$ M or more.

The term "high affinity" for an IgG antibody refers to an antibody having a $K_D$ of $1.0\times10^{-7}$ M or less, more preferably $1.0\times10^{-8}$ M or less, even more preferably $1.0\times10^{-9}$ M or less, and even more preferably $1.0\times10^{-10}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

The term "$K_{assoc}$" or "$K_a$", as used herein, is intended to refer to the association rate of a particular antibody-antigen interaction, whereas the term "$K_{dis}$" or "$K_d$", as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as the surface plasmon resonance system Biacore™.

The term "$EC_{50}$", also known as half maximal effective concentration, refers to the concentration of an antibody which induces a response halfway between the baseline and maximum after a specified exposure time.

The term "$IC_{50}$", also known as half maximal inhibitory concentration, refers to the concentration of an antibody which inhibits a specific biological or biochemical function by 50% relative to the absence of the antibody.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

The term "therapeutically effective amount" means an amount of the antibody or the antigen binding portion of the present disclosure sufficient to prevent or ameliorate the symptoms associated with a disease or condition (such as a chronic inflammation) and/or lessen the severity of the disease or condition. A therapeutically effective amount is understood to be in context to the condition being treated, where the actual effective amount is readily discerned by those of skill in the art.

Various aspects of the disclosure are described below in further detail.

The antibody, or the antigen-binding portion thereof, of the disclosure specifically binds to human, monkey and/or mouse PD-1 and has i) comparable, if not higher, binding affinity/capacity to human, monkey and mouse PD-1, ii) comparable, if not higher, blocking activity on PD-1-PD-L1 interaction, and/or iii) comparable, if not better, in vivo anti-tumor activity, as compared to prior art anti-PD-1 antibodies such as nivolumab and pembrolizumab. The antibody or antigen binding portion thereof of the disclosure may be mouse, chimeric or humanized.

The antibody or antigen binding portion thereof of the disclosure is structurally and chemically characterized below. The amino acid sequence ID numbers of the heavy/light chain variable regions and CDRs of the antibodies or antigen binding portions thereof of the disclosure are summarized in Table 1 below, some antibodies sharing the same VH or VL. The heavy chain constant region for the antibodies may be human IgG4 heavy chain constant region having an amino acid sequence set forth in, e.g., SEQ ID NO: 24, or other heavy chain constant region with weak FcR binding affinity, for tumor and infectious disease treatment, or immune response enhancement. The heavy chain constant region may also be e.g., human IgG1 constant region with high FcR binding affinity. The light chain constant region for the antibodies may be human kappa constant region having an amino acid sequence set forth in, e.g., SEQ ID NO: 25. The antibodies of the disclosure may also contain human lambda light chain constant region.

The heavy chain variable region CDRs and the light chain variable region CDRs in Table 1 have been defined by the Kabat numbering system. However, as is well known in the art, CDR regions can also be determined by other systems such as Chothia, and IMGT, AbM, or Contact numbering system/method, based on heavy chain/light chain variable region sequences.

The $V_H$ and $V_L$ sequences (or CDR sequences) of other Anti-PD-1 antibodies which bind to human PD-1 can be "mixed and matched" with the $V_H$ and $V_L$ sequences (or CDR sequences) of the anti-PD-1 antibody of the present disclosure. Preferably, when $V_H$ and $V_L$ chains (or the CDRs within such chains) are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one embodiment, an antibody of the disclosure, or an antigen binding portion thereof, may comprise:

(a) a heavy chain variable region which may comprise an amino acid sequence listed above in Table 1; and (b) a light chain variable region which may comprise an amino acid sequence listed above in Table 1, or the $V_L$ of another Anti-PD-1 antibody, wherein the antibody specifically binds human PD-1.

TABLE 1

| Amino acid sequence ID numbers of heavy/light chain variable regions and CDRs | | | | | | | | |
|---|---|---|---|---|---|---|---|---|
| Antibody ID | VH-CDR1 | VH-CDR2 | VH-CDR3 | VH | VL-CDR1 | VL-CDR2 | VL-CDR3 | VL |
| E1A9C8A7 | 1 | 3 | 6, X1 = D, X2 = Y | 14 | 8, X1 = I, X2 = N | 10 | 12 | 20 |
| huE1A9C8A7-V1 | 1 | 3 | 6, X1 = D, X2 = Y | 15, X1 = S, X2 = M, X3 = K | 8, X1 = I, X2 = N | 10 | 12 | 21. X1 = N |
| huE1A9C8A7-V2 | 1 | 3 | 6, X1 = D, X2 = Y | 15, X1 = T, X2 = M, X3 = K | 8, X1 = I, X2 = N | 10 | 12 | 21, X1 = N |
| huE1A9C8A7-V3 | 1 | 3 | 6, X1 = D, X2 = Y | 15, X1 = S, X2 = V, X3 = K | 8, X1 = I, X2 = N | 10 | 12 | 21, X1 = N |
| huE1A9C8A7-V4 | 1 | 3 | 6, X1 = D, X2 = Y | 15, X1 = S, X2 = M, X3 = T | 8, X1 = I, X2 = N | 10 | 12 | 21, X1 = N |
| huE1A9C8A7-V5 | 1 | 3 | 6, X1 = D, X2 = Y | 15, X1 = T, X2 = V, X3 = T | 8, X1 = I, X2 = N | 10 | 12 | 21, X1 = N |
| huE1A9C8A7-V6 | 1 | 3 | 6, X1 = D, X2 = Y | 16, X1 = V, X2 = S, X3 = I | 8, X1 = I, X2 = N | 10 | 12 | 21, X1 = N |
| huE1A9C8A7-V7 | 1 | 3 | 6, X1 = D, X2 = Y | 16, X1 = I, X2 = G, X3 = I | 8, X1 = I, X2 = N | 10 | 12 | 21, X1 = N |
| huE1A9C8A7-V8 | 1 | 3 | 6, X1 = D, X2 = Y | 16, X1 = I, X2 = S, X3 = M | 8, X1 = I, X2 = N | 10 | 12 | 21, X1 = N |
| huE1A9C8A7-V8-3 | 1 | 3 | 6, X1 = E, X2 = Y | 42 | 8, X1 = I, X2 = A | 10 | 12 | 21, X1 = A |
| huE1A9C8A7-V9 | 1 | 3 | 6, X1 = D, X2 = Y | 17, X1 = R, X2 = A, X3 = V | 8, X1 = I, X2 = N | 10 | 12 | 21, X1 = N |
| huE1A9C8A7-V10 | 1 | 3 | 6, X1 = D, X2 = Y | 17, X1 = K, X2 = V, X3 = V | 8, X1 = I, X2 = N | 10 | 12 | 21, X1 = N |
| huE1A9C8A7-V11 | 1 | 3 | 6, X1 = D, X2 = Y | 17, X1 = K, X2 = A, X3 = R | 8, X1 = I, X2 = N | 10 | 12 | 21, X1 = N |
| E2G4E10B7 | 1 | 4 | 6, X1 = D, X2 = W | 18 | 8, X1 = L, X2 = D | 10 | 12 | 22 |
| E1G5D1H1 | 2 | 5 | 7 | 19 | 9 | 11 | 13 | 23 |

In another embodiment, an antibody of the disclosure, or an antigen binding portion thereof, may comprise:

(a) the CDR1, CDR2, and CDR3 regions of the heavy chain variable region listed above in Table 1; and (b) the CDR1, CDR2, and CDR3 regions of the light chain variable region listed above in Table 1 or the CDRs of another anti-PD-1 antibody, wherein the antibody specifically binds human PD-1.

In yet another embodiment, the antibody, or antigen binding portion thereof, includes the heavy chain variable CDR2 region of anti-PD-1 antibody combined with CDRs of other antibodies which bind human PD-1, e.g., CDR1 and/or CDR3 from the heavy chain variable region, and/or CDR1, CDR2, and/or CDR3 from the light chain variable region of a different anti-PD-1 antibody.

In addition, it is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, e.g., Klimka et al., *British J. of Cancer* 83(2):252-260 (2000); Beiboer et al., *J. Mol. Biol.* 296:833-849 (2000); Rader et al., *Proc. Natl. Acad. Sci. U.S.A.* 95:8910-8915 (1998); Barbas et al., *J. Am. Chem. Soc.* 116:2161-2162 (1994); Barbas et al., *Proc. Natl. Acad. Sci. U.S.A.* 92:2529-2533 (1995); Ditzel et al., *J. Immunol.* 157:739-749 (1996); Berezov et al., *BIAjournal* 8: *Scientific Review* 8 (2001); Igarashi et al., *J. Biochem* (Tokyo) 117:452-7 (1995); Bourgeois et al., *J. Virol* 72:807-10 (1998); Levi et al., *Proc. Natl. Acad. Sci. U.S.A.* 90:4374-8 (1993); Polymenis and Stoller, *J. Immunol.* 152: 5218-5329 (1994) and Xu and Davis, Immunity 13:37-45 (2000). See also, U.S. Pat. Nos. 6,951,646; 6,914,128; 6,090,382; 6,818,216; 6,156,313; 6,827,925; 5,833,943; 5,762,905 and 5,760,185. Each of these references is hereby incorporated by reference in its entirety.

Accordingly, in another embodiment, antibodies of the disclosure may comprise the CDR2 of the heavy chain variable region of the anti-PD-1 antibody and at least the CDR3 of the heavy and/or light chain variable region of the anti-PD-1 antibody, or the CDR3 of the heavy and/or light chain variable region of another anti-PD-1 antibody, wherein the antibody is capable of specifically binding to human PD-1. These antibodies preferably (a) compete for binding with PD-1; (b) retain the functional characteristics; (c) bind to the same epitope; and/or (d) have a similar binding affinity as the anti-PD-1 antibody of the present disclosure. In yet another embodiment, the antibodies further may comprise the CDR2 of the light chain variable region of the anti-PD-1 antibody, or the CDR2 of the light chain variable region of another anti-PD-1 antibody, wherein the antibody is capable of specifically binding to human PD-1. In another embodiment, the antibodies of the disclosure may include the CDR1 of the heavy and/or light chain variable region of the anti-PD-1 antibody, or the CDR1 of the heavy and/or light chain variable region of another anti-PD-1 antibody, wherein the antibody is capable of specifically binding to human PD-1.

In another embodiment, an antibody of the disclosure may comprise a heavy and/or light chain variable region sequences of CDR1, CDR2 and CDR3 sequences which differ from those of the anti-PD-1 antibodies of the present disclosure by one or more conservative modifications. It is understood in the art that certain conservative sequence modification can be made which do not remove antigen binding. See, e.g., Brummell et al., (1993) *Biochem* 32:1180-8; de Wildt et al., (1997) *Prot. Eng.* 10:835-41; Komissarov et al., (1997) *J. Biol. Chem.* 272:26864-26870; Hall et al., (1992) *J. Immunol.* 149:1605-12; Kelley and O'Connell (1993) *Biochem.*32:6862-35; Adib-Conquy et al., (1998)*Int. Immunol.*10:341-6 and Beers et al., (2000) *Clin. Can. Res.* 6:2835-43.

Accordingly, in one embodiment, the antibody may comprise a heavy chain variable region which may comprise CDR1, CDR2, and CDR3 sequences and/or a light chain variable region which may comprise CDR1, CDR2, and CDR3 sequences, wherein:

(a) the heavy chain variable region CDR1 sequence may comprise a sequence listed in Table 1 above, and/or conservative modifications thereof; and/or (b) the heavy chain variable region CDR2 sequence may comprise a sequence listed in Table 1 above, and/or conservative modifications thereof; and/or (c) the heavy chain variable region CDR3 sequence may comprise a sequence listed in Table 1 above, and conservative modifications thereof; and/or (d) the light chain variable region CDR1, and/or CDR2, and/or CDR3 sequences may comprise the sequence(s) listed in Table 1 above; and/or conservative modifications thereof; and (e) the antibody specifically binds human PD-1.

The antibody of the present disclosure possesses one or more of the following functional properties described above, such as high affinity binding to human PD-1, and blocking activity on PD-1-PD-L1 binding.

In various embodiments, the antibody can be, for example, a mouse, human, humanized or chimeric antibody.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the disclosure can be replaced with other amino acid residues from the same side chain family and the altered antibody can be tested for retained function (i.e., the functions set forth above) using the functional assays described herein.

Antibodies of the disclosure can be prepared using an antibody having one or more of the $V_H/V_L$ sequences of the anti-PD-1 antibody of the present disclosure as starting material to engineer a modified antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al., (1998) *Nature* 332:323-327; Jones et al., (1986) *Nature* 321:522-525; Queen et al., (1989) *Proc. Natl. Acad*. See also U.S. Pat. Nos. 5,225,539; 5,530,101; 5,585,089; 5,693,762 and 6,180,370).

Accordingly, another embodiment of the disclosure pertains to an isolated monoclonal antibody, or antigen binding portion thereof, which may comprise a heavy chain variable region that may comprise CDR1, CDR2, and CDR3 sequences which may comprise the sequences of the present disclosure, as described above, and/or a light chain variable region which may comprise CDR1, CDR2, and CDR3 sequences which may comprise the sequences of the present disclosure, as described above. While these antibodies contain the $V_H$ and $V_L$ CDR sequences of the monoclonal antibody of the present disclosure, they can contain different framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat et al., (1991), cited supra; Tomlinson et al., (1992) *J. Mol. Biol.* 227:776-798; and Cox et al., (1994) *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank Accession Nos.: 1-69 (NG—0010109, NT—024637 & BC070333), 3-33 (NG—0010109 & NT—024637) and 3-7 (NG—0010109 & NT—024637). As another example, the following heavy chain germline sequences found in the HCo12 HuMAb mouse are available in the accompanying Genbank Accession Nos.: 1-69 (NG—0010109, NT—024637 & BC070333), 5-51 (NG—0010109 & NT—024637), 4-34 (NG—0010109 & NT—024637), 3-30.3 (CAJ556644) & 3-23 (AJ406678).

Antibody protein sequences are compared against a compiled protein sequence database using one of the sequence similarity searching methods called the Gapped BLAST (Altschul et al., (1997), supra), which is well known to those skilled in the art.

Preferred framework sequences for use in the antibodies of the disclosure are those that are structurally similar to the framework sequences used by antibodies of the disclosure. The $V_H$ CDR1, CDR2, and CDR3 sequences can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as known in the art. Preferably conservative modifications (as known in the art) are introduced. The mutations can be amino acid substitutions, additions or deletions, but are preferably substitutions. Moreover, typically no more than one, two, three, four or five residues within a CDR region are altered.

Accordingly, in another embodiment, the disclosure provides isolated anti-PD-1 monoclonal antibodies, or antigen binding portions thereof, which may comprise a heavy chain variable region that may comprise: (a) a $V_H$ CDR1 region which may comprise the sequence of the present disclosure, or an amino acid sequence having one, two, three, four or five amino acid substitutions, deletions or additions; (b) a $V_H$ CDR2 region which may comprise the sequence of the present disclosure, or an amino acid sequence having one, two, three, four or five amino acid substitutions, deletions or additions; (c) a $V_H$ CDR3 region which may comprise the sequence of the present disclosure, or an amino acid sequence having one, two, three, four or five amino acid substitutions, deletions or additions; (d) a $V_L$ CDR1 region which may comprise the sequence of the present disclosure, or an amino acid sequence having one, two, three, four or five amino acid substitutions, deletions or additions; (e) a $V_L$ CDR2 region which may comprise the sequence of the present disclosure, or an amino acid sequence having one, two, three, four or five amino acid substitutions, deletions or additions; and (f) a $V_L$ CDR3 region which may comprise the sequence of the present disclosure, or an amino acid sequence having one, two, three, four or five amino acid substitutions, deletions or additions.

Engineered antibodies of the disclosure include those in which modifications have been made to framework residues within $V_H$ and/or $V_L$, e.g. to improve the properties of the antibody. Typically, such framework modifications are made to decrease the immunogenicity of the antibody. For example, one approach is to "back-mutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Pat. No. 7,125,689.

In addition, or as an alternative to modifications made within the framework or CDR regions, antibodies of the disclosure can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the disclosure can be chemically modified (e.g., one or more chemical moieties can be attached to the antibody) or be modified to alter its glycosylation, again to alter one or more functional properties of the antibody.

In one embodiment, the hinge region of $C_{H1}$ is modified in such that the number of cysteine residues in the hinge region is altered, e.g., increased or decreased. This approach is described further in U.S. Pat. No. 5,677,425. The number of cysteine residues in the hinge region of $C_{H1}$ is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the $C_{H2}$-$C_{H3}$ domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In still another embodiment, the glycosylation of an antibody is modified. For example, a glycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase or reduce the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. For example, the cell lines Ms704, Ms705, and Ms709 lack the fucosyltransferase gene, FUT8 (α(1, 6)-fucosyltransferase), such that antibodies expressed in the Ms704, Ms705, and Ms709 cell lines lack fucose on their carbohydrates. The Ms704, Ms705, and Ms709 FUT8−/− cell lines were created by the targeted disruption of the FUT8 gene in CHO/DG44 cells using two replacement vectors (see U.S. Patent Publication No. 20040110704 and Yamane-Ohnuki et al., (2004) Biotechnol Bioeng 87:614-22). As another example, EP1,176,195B1 describes a cell line with a functionally disrupted FUT8 gene, which encodes a fucosyl transferase, such that antibodies expressed in such a cell line exhibit hypofucosylation by reducing or eliminating the α-1, 6 bond-related enzyme. EP1,176,195B1 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn (297)-linked carbohydrates, also resulting in hypofucosylation of antibodies expressed in that host cell (see also Shields et al., (2002) J. Biol. Chem. 277:26733-26740). Antibodies with a modified glycosylation profile can also be produced in chicken eggs, as described in PCT Publication WO 06/089231. Alternatively, antibodies with a modified glycosylation profile can be produced in plant cells, such as Lemna. The fucose residues of the antibody can be cleaved off using a fucosidase enzyme; e.g., the fucosidase α-L-fucosidase removes fucosyl residues from antibodies (Tarentino et al., (1975) *Biochem.* 14:5516-23).

Another modification of the antibodies herein that is contemplated by this disclosure is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the disclosure. See, e.g., EP0154316B1 and EP0401384B1.

Antibodies of the disclosure can be characterized by their various physical properties, to detect and/or differentiate different classes thereof.

For example, antibodies can contain one or more glycosylation sites in either the light or heavy chain variable region. Such glycosylation sites may result in increased immunogenicity of the antibody or an alteration of the pK of the antibody due to altered antigen binding (Marshall et al (1972) *Annu Rev Biochem* 41:673-702; Gala and Morrison (2004) *J Immunol* 172:5489-94; Wallick et al (1988) *J Exp Med* 168:1099-109; Spiro (2002) *Glycobiology* 12:43R-56R; Parekh et al (1985) *Nature* 316:452-7; Mimura et al., (2000) *Mol Immunol* 37:697-706). Glycosylation has been known to occur at motifs containing an N-X-S/T sequence. In some instances, it is preferred to have an anti-PD-1 antibody that does not contain variable region glycosylation. This can be achieved either by selecting antibodies that do not contain the glycosylation motif in the variable region or by mutating residues within the glycosylation region.

In a preferred embodiment, the antibodies do not contain asparagine isomerism sites. The deamidation of asparagine may occur on N-G or D-G sequences and result in the creation of an isoaspartic acid residue that introduces a link into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-PD-1 antibody that contains a pI value that falls in the normal range. This can be achieved either by selecting antibodies with a pI in the normal range or by mutating charged surface residues.

In another aspect, the disclosure provides nucleic acid molecules that encode heavy and/or light chain variable regions, or CDRs, of the antibodies of the disclosure. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques. A nucleic acid of the disclosure can be, e.g., DNA or RNA and may or may not contain intronic sequences. In a preferred embodiment, the nucleic acid is a cDNA molecule.

Nucleic acids of the disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of the disclosure include those encoding the $V_H$ and $V_L$ sequences of the PD-1 monoclonal antibody or the CDRs. Once DNA fragments encoding $V_H$ and $V_L$ Segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_{H1}$, $C_{H2}$ and $C_{H3}$). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain $C_{H1}$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence (Gly4-Ser)3, such that the $V_H$ and $V_L$ sequences can be expressed as a contiguous single-chain protein, with the $V_L$ and $V_H$ regions joined by the flexible linker (see e.g., Bird et al., (1988) *Science* 242:423-426; Huston et al., (1988) *Proc. Natl. Acad. Sci. USA* 85:5879-5883; McCafferty et al., (1990) *Nature* 348:552-554).

Monoclonal antibodies (mAbs) of the present disclosure can be produced using the well-known somatic cell hybridization (hybridoma) technique of Kohler and Milstein (1975) *Nature* 256: 495. Other embodiments for producing monoclonal antibodies include viral or oncogenic transformation of B lymphocytes and phage display techniques. Chimeric or humanized antibodies are also well known in the art. See e.g., U.S. Pat. Nos. 4,816,567; 5,225,539; 5,530,101; 5,585,089; 5,693,762 and 6,180,370, the contents of which are specifically incorporated herein by reference in their entirety.

Antibodies of the disclosure also can be produced in a host cell transfectoma using, for example, a combination of recombinant DNA techniques and gene transfection methods as is well known in the art (e.g., Morrison, S. (1985) Science 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody genes. Such regulatory sequences are described, e.g., in Goeddel (Gene Expression Technology. Methods in Enzymology 185, Academic Press, San Diego, Calif (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, e.g., the adenovirus major late promoter (AdMLP) and polyomavirus enhancer. Alternatively, non-viral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al., (1988) Mol. Cell. Biol. 8:466-472). The expression vector and expression control sequences are chosen to be compatible with the expression host cell used.

The antibody light chain gene and the antibody heavy chain gene can be inserted into the same or separate expression vectors. In preferred embodiments, the variable regions are used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the disclosure in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the disclosure include Chinese Hamster Ovary (CHO cells) (including dhfr-CHO cells, described in Urlaub and Chasm, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular for use with NSO myeloma cells, another preferred expression system is the GS gene expression system disclosed in WO 87/04462, WO 89/01036 and EP338841B1. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

In another aspect, the present disclosure features bispecific molecules which may comprise one or more antibodies of the disclosure linked to at least one other functional molecule, e.g., another peptide or protein (e.g., another antibody or ligand for a receptor) to generate a bispecific molecule that binds to at least two different binding sites or target molecules. Thus, as used herein, "bispecific molecule" includes molecules that have three or more specificities.

In an embodiment, a bispecific molecule has, in addition to the FcR binding specificity and an anti-PD-1 binding specificity, a third specificity. The third specificity can be for PD-1.

Bispecific molecules may be in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFv's) linked by a peptide chain, a so-called Bs(scFv) 2 construct. Intermediate-sized bispecific molecules include two different F(ab) fragments linked by a peptidyl linker. Bispecific molecules of these and other formats can be prepared by genetic engineering, somatic hybridization, or chemical methods. See, e.g., Kufer et al, cited supra; Cao and Suresh, *Bioconjugate Chemistry,* 9 (6), 635-644 (1998); and van Spriel et al., *Immunology Today,* 21 (8), 391-397 (2000), and the references cited therein.

In yet another aspect, the invention provides diagnostic methods, compositions and kits. In an embodiment, an antibody or an antigen-binding portion thereof of the invention is used to determine the presence and amount of PD-1 in a tissue. In an embodiment, the diagnostic indicates prognosis and/or directs treatment and/or follow-up treatment. For example, PD-1 signaling has been targeted for treatment of infectious diseases and tumors. In an embodiment, an antibody or an antigen binding portion thereof of the invention is employed in diagnostic kit or method to determine prognosis and appropriate treatment and follow-up of an infectious disease and/or PD-1 related tumors or cancers.

Antibodies of the disclosure can be conjugated to a therapeutic agent to form an immunoconjugate such as an antibody-drug conjugate (ADC). Suitable therapeutic agents include an anti-inflammatory agent and an anti-cancer agent. In the ADC, the antibody and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038,658; WO 07/051,081; WO 07/059,404; WO 08/083,312; and WO 08/103,693; U.S. Pat. Nos. 7,691,962; 7,517,903; and 7,714,016; the disclosures of which are incorporated herein by reference.

Also provided herein are a chimeric antigen receptor (CAR) containing an anti-PD-1 scFv, the anti-PD-1 scFv may comprise CDRs and heavy/light chain variable regions described herein.

The anti-PD-1 CAR may comprise (a) an extracellular antigen binding domain which may comprise an anti-PD-1 scFv; (b) a transmembrane domain; and (c) an intracellular signaling domain.

The CAR may contain a signal peptide at the N-terminus of the extracellular antigen binding domain that directs the nascent receptor into the endoplasmic reticulum, and a hinge peptide at the N-terminus of the extracellular antigen binding domain that makes the receptor more available for binding. The CAR preferably comprises, at the intracellular signaling domain, a primary intracellular signaling domain and one or more co-stimulatory signaling domains. The mainly used and most effective primary intracellular signaling domain is CD3-zeta cytoplasmic domain which contains ITAMs, the phosphorylation of which results in T cell activation. The co-stimulatory signaling domain may be derived from the co-stimulatory proteins such as CD28, CD137 and OX40.

The CARs may further add factors that enhance T cell expansion, persistence, and anti-tumor activity, such as cytokines, and co-stimulatory ligands.

Also provided are engineered immune effector cells, which may comprise the CAR provided herein. In certain embodiments, the immune effector cell is a T cell, an NK cell, a peripheral blood mononuclear cell (PBMC), a hematopoietic stem cell, a pluripotent stem cell, or an embryonic stem cell. In certain embodiments, the immune effector cell is a T cell.

An oncolytic virus preferentially infects and kills cancer cells. The antibody or antigen binding portion thereof of the disclosure may be used in conjunction with the oncolytic virus. Alternatively, an oncolytic virus encoding the antibody or antigen binding portion thereof of the disclosure can be introduced into human body.

In another aspect, the present disclosure provides a pharmaceutical composition comprising the antibody or antigen binding portion thereof, the immunoconjugate, the bispecific molecule, the immune cell carrying the chimeric antigen receptor, the oncolytic virus, the nucleic acid molecule, the expression vector, and/or the host cell of the present disclosure formulated together with a pharmaceutically acceptable carrier. The composition may optionally contain one or more additional pharmaceutically active ingredients, such as an anti-tumor agent, an anti-infective agent, or an agent for immunity enhancement. The pharmaceutical composition of the disclosure may be administered in a combination therapy with, for example, an anti-tumor agent, an anti-infective agent, or an agent for immunity enhancement.

The pharmaceutical composition may comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients are taught in Gennaro, ed., Remington: *The Science and Practice of Pharmacy,* 20th Ed. (Lippincott Williams & Wilkins 2003), the disclosure of which is incorporated herein by reference.

Preferably, the pharmaceutical composition is suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion. Alternatively, an antibody of the disclosure can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about ninety-nine percent of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active ingredient calculated to produce the desired therapeutic effect in association with the required pharmaceutical carrier. Alternatively, antibody can be administered as a sustained release formulation, in which case less frequent administration is required.

For administration of the composition, the dosage may range from about 0.0001 to 100 mg/kg, and more usually 0.01 to 5 mg/kg, of the host body weight. For example, dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-PD-1 antibody of the disclosure include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 μg/ml and in some methods about 25-300 μg/ml.

A "therapeutically effective dosage" of an anti-PD-1 antibody of the disclosure preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 20%, more preferably by at least about 40%, even more preferably by at least about 60%, and still more preferably by at least about 80% relative to untreated subjects. A therapeutically effective amount of a therapeutic antibody can decrease tumor size, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the monoclonal antibodies or antigen binding portions thereof of the disclosure can be formulated to ensure proper distribution in vivo. For example, to ensure that the therapeutic antibody of the disclosure cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) *J. Clin.Pharmacol.*29:685; Umezawa et al., (1988) *Biochem. Biophys. Res. Commun.* 153:1038; Bloeman et al., (1995) *FEBS Lett.*357:140; M. Owais et al., (1995) *Antimicrob. Agents Chemother.* 39:180; Briscoe et al., (1995) *Am. J. Physiol.* 1233:134; Schreier et al., (1994) *J. Biol. Chem.* 269:9090; Keinanen and Laukkanen (1994) *FEBS Lett.* 346:123; and Killion and Fidler (1994) *Immunomethods* 4:273.

The pharmaceutical composition of the present disclosure has numerous in vitro and in vivo utilities involving, for example, treatment of infectious diseases and tumors caused by PD-1 signaling.

The disclosure provides a method for treating a disease associated with PD-1 signaling, which may comprise administering to a subject a therapeutically effective amount of the composition of the present disclosure.

The disease may be tumor or cancer. The tumor or cancer includes, but not limited to, non-small-cell lung cancer (NSCLC), renal cell carcinoma (RCC), bladder cancer (BC), colorectal cancer (CRC) with microsatellite instability or mismatch repair deficiency (MSI-H/dMMR), hepatocellular carcinoma (HCC), classic Hodgkin lymphoma (cHL), melanoma, head and neck squamous cell carcinoma (HNSCC), cervical cancer, stomach cancer, gastroesophageal cancer, and all advanced solid tumors with MSI-H/dMMR. The composition comprises the antibody, or the antigen-binding portion thereof, with weak FcR binding heavy chain constant regions, the bispecific molecule, the nucleic acid molecule, or the expression vector of the disclosure. In certain embodiments, the subject is human.

The disease may be an infectious disease, including, but not limited to those caused by viruses, bacteria, or fungi. In certain embodiments, the infectious disease is sepsis, HIV infection, simian immunodeficiency virus infection, HBV infection, or HCV infection. The composition comprises the antibody, or the antigen-binding portion thereof, with weak FcR binding heavy chain constant regions, the bispecific molecule, the nucleic acid molecule, or the expression vector of the disclosure.

The disease may be an inflammatory disease. The inflammatory disease includes, but not limited to, rheumatoid arthritis, colitis, lupus-like nephritis, systemic lupus erythematosus, and psoriasis. The composition of the disclosure comprises the antibody, or the antigen-binding portion thereof, with high FcR binding heavy chain constant regions, the immunoconjugate, the bispecific molecule, the immune cell with CAR, the nucleic acid molecule, or the expression vector of the disclosure. In certain embodiments, the composition of the disclosure is administered via local delivery to the inflammatory tissues.

In yet another aspect, the disclosure provides a method of modulating or enhancing an immune response in a subject comprising administering to the subject the composition of the disclosure such that the immune response in the subject is modulated/enhanced. The composition comprises the antibody, or the antigen-binding portion thereof, with weak FcR binding heavy chain constant regions, the bispecific molecule, the nucleic acid molecule, or the expression vector of the disclosure.

In one aspect, the disclosure provides combination therapy in which the pharmaceutical composition of the present disclosure is co-administered with one or more additional agents that are effective in ameliorating PD-1 related infectious diseases. Such agents may be an anti-infectious agent, such as an anti-viral agent, an anti-bacterial agent, or an anti-fungal agent. In certain embodiments, the subject is human.

In another aspect, the disclosure provides methods of combination therapy in which the pharmaceutical composition of the present disclosure is co-administered with one or more additional antibodies that are effective in inhibiting tumor growth in a subject. In one embodiment, the disclosure provides a method for inhibiting tumor growth in a subject which may comprise administering to the subject the pharmaceutical composition of the disclosure and one or more additional antibodies, such as an anti-VEGF antibody, an anti-OX40 antibody, an anti-TIM-3 antibody, an anti-CD137 antibody, an anti-GITR antibody, an anti-LAG-3 antibody, and an anti-PD-L1 antibody. In certain embodiments, the subject is human. The PD-1 pathway blockade can also be further combined with standard cancer treatments. For example, PD-1 pathway blockade can be combined with CTLA-4 blockade and also chemotherapeutic regimes. For example, a chemotherapeutic agent can be administered with the anti-PD-1 antibodies, which may be a cytotoxic agent. For example, epirubicin, oxaliplatin, and 5-FU are administered to patients receiving anti-PD-1 therapy. Optionally, the combination of anti-PD-1 and one or more additional antibodies (e.g., anti-CTLA-4 and/or anti-PD-L1 antibodies) can be further combined with an immunogenic agent, such as cancerous cells, purified tumor antigens (including recombinant proteins, peptides, and carbohydrate molecules), and cells transfected with genes encoding immune stimulating cytokines (He et al., (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF. Other therapies that may be combined with anti-PD-1 antibody includes, but not limited to, interleukin-2 (IL-2) administration, radiation, surgery, or hormone deprivation.

The combination of therapeutic agents discussed herein can be administered concurrently as a single composition in a pharmaceutically acceptable carrier, or concurrently as separate compositions with each agent in a pharmaceutically acceptable carrier. In another embodiment, the combination of therapeutic agents can be administered sequentially.

Furthermore, if more than one dose of the combination therapy is administered sequentially, the order of the sequential administration can be reversed or kept in the same order at each time point of administration, sequential administrations can be combined with concurrent administrations, or any combination thereof.

Although the present invention and its advantages have been described in detail, it should be understood that various changes, substitutions and alterations can be made herein without departing from the spirit and scope of the invention as defined in the appended claims.

The present disclosure is further illustrated by the following examples, which should not be construed as further limiting. The contents of all figures and all references, Genbank sequences, patents and published patent applications cited throughout this application are expressly incorporated herein by reference.

EXAMPLES

Example 1. Generation of Mouse Anti-PD-1 Monoclonal Antibodies Using Hybridoma Technology Immunization Mice were immunized according to the method as described in E Harlow, D. Lane, Antibody: A Laboratory Manual, Cold Spring Harbor Laboratory Press, Cold Spring Harbor, N.Y., 1998. Recombinant human PD-1 protein with human IgG1 Fc tag at the C-terminus (Cat #: PD1-H5257, Acro biosystems Inc., containing extra-cellular domain of human PD-1) was used as the immunogen, and in house made human PD-1-Fc protein (amino acid sequence set forth in SEQ ID NO: 26) was used for determining anti-sera titers and for screening hybridomas secreting antigen-specific antibodies.

Immunizing dosages contained 22.5 μg recombinant human PD-1-Fc protein per mouse per injection for primary immunization, and 25 μg per mouse per injection for boost immunizations. To increase immune response, the complete Freud's adjuvant and incomplete Freud's adjuvant (Sigma-Aldrich®, St. Louis, Mo., USA) were used respectively for primary and boost immunizations. Briefly, the immunogen was prepared in PBS or saline with concentration ranging from 0.23 to 0.35 mg/ml, a calculated amount of the immunogen was then added to micro-centrifuge tubes with desired amount of adjuvant, and the resulting mixtures were mixed by gently vortexing for 2 minutes to generate water-in-oil emulsions. The adjuvant-antigen emulsion was then drawn into a proper syringe for animal injection. A total of 22.5 or 25 μg of immunogen was injected in a volume of 150-200 μl. Each animal was immunized, and then boosted for 3 to 4 times depending on the anti-sera titer. Animals with good titers, as measured by ELISA, were given a final boost by intraperitoneal injection before hybridoma fusion.

Hybridoma Fusion and Screening

Cells of murine myeloma cell line (SP2/0-Ag14, ATCC #CRL-1581) were cultured to reach the log phase stage right before hybridoma fusion. Spleen cells from immunized mice were prepared sterilely and fused with murine myeloma cells according to the method as described in Kohler G, and Milstein C, "Continuous cultures of fused cells secreting antibody of predefined specificity," *Nature,* 256: 495-497 (1975). Fused "hybrid cells" were subsequently dispensed into 96-well plates in DMEM/20% FCS/HAT media. Surviving hybridoma colonies were observed under the microscope seven to ten days post fusion. After two weeks, the supernatant from each well was subjected to Capture ELISA using in house made biotin-labeled human PD-1-Fc protein. Positive hybridomas secreting antibodies that bound to human PD-1-Fc protein were selected and transferred to 24-well plates. Hybridoma clones producing antibodies that showed high specific human PD-1 binding and PD-1-PD-L1 blocking activities were subcloned by limited dilution to ensure the clonality of the cell line, and then monoclonal antibodies were purified. Briefly, Protein A sepharose column (Cat #AA0273, bestchrom (Shanghai) Biosciences) was washed using PBS buffer in 5 to 10 column volumes. Cell supernatants from the hybridomas of the disclosure were passed through the columns, and then the columns were washed using PBS buffer until the absorbance for protein reached the baseline. The columns were eluted with elution buffer (0.1 M Glycine-HCl, pH 2.7), and immediately collected into tubes with neutralizing buffer (1 M Tris-HCl, pH 9.0). Fractions containing immunoglobulins were pooled and dialyzed in PBS overnight at 4° C. Subsequently, in vitro and in vivo functional activities of purified mouse monoclonal antibodies were characterized as follows.

Example 2. Binding Affinity Determination of Mouse Anti-PD-1 Monoclonal Antibodies Using Biacore™ Surface Plasmon Resonance Technology The purified anti-PD-1 mouse monoclonal antibodies (mAbs) generated in Example 1 were characterized for binding affinities and binding kinetics by Biacore™ T200 system (GE healthcare, Pittsburgh, PA, USA). The Opdivo® nivolumab (Bristol-Myers Squibb) and Keytruda® pembrolizumab (Merck Sharp & Dohme Ltd) were used as positive controls.

Briefly, Goat-Anti-Mouse IgG (Cat #: BR100838, GE healthcare, Mouse Antibody Capture Kit) was covalently linked to a CM5 chip (carboxy methyl dextran coated chip, Cat #:BR100530, GE healthcare) via primary amines using a standard amine coupling kit (GE healthcare, Pittsburgh, PA, USA) provided by Biacore™. Un-reacted moieties on the biosensor surface were blocked with ethanolamine. A Protein G chip (Cat #:29-1793-15, GE healthcare) was used for the positive controls' affinity determination. The anti-PD-1 antibodies of the disclosure and the two positive controls at the concentration of 2 μg/ml were respectively flowed onto the chip at a flow rate of 10 μl/min. Then, serially diluted recombinant human PD-1-his protein (Cat #:10377-H08H, Sino biological Inc.), cynomolgus PD-1-his protein (Cat #:PD1-C5223, Acro biosystems Inc.) and recombinant mouse PD-1-his protein (Cat #:50124-M08H, Sino Biological Inc), 2-fold dilution in HBS-EP+ buffer (provided by Biacore™) starting at 200 nM, were respectively flowed onto the chip at a flow rate of 30 μl/min. The antigen-antibody association kinetics was followed for 2 minutes and the dissociation kinetics was followed for 10 minutes. The association and dissociation curves were fit to a 1:1 Langmuir binding model using Biacore™ evaluation software. The $K_D$, $K_a$ and $K_d$ values were determined and summarized in Table 2-1 and Table 2-2 below.

All the mouse antibodies of the disclosure specifically bound to human PD-1 with higher binding affinities than nivolumab and pembrolizumab, and bound to monkey PD-1 with comparable or higher binding affinities compared to nivolumab and pembrolizumab. Further, E1A9C8A7 and E2G4E10B7 specifically bound to mouse PD-1, while nivolumab and pembrolizumab did not.

TABLE 2-1

Binding affinities of Mouse anti-PD-1 Monoclonal Antibodies to Human and Cyno PD-1

| Mouse mAb | Kinetics on Biacore ™ | | | | | |
|---|---|---|---|---|---|---|
| | Human PD-1-his | | | Cynomolgus PD-1-his | | |
| | $K_a$ ($M^{-1}s^{-1}$) | $K_d$ ($s^{-1}$) | $K_D$ (M) | $K_a$ ($M^{-1}s^{-1}$) | $K_d$ ($s^{-1}$) | $K_D$ (M) |
| E1G5D1H1 | 3.63E+05 | 8.56E−05 | 2.36E−10 | 3.45E+05 | 4.32E−05 | 1.25E−10 |
| E1A9C8A7 | 1.99E+05 | 2.20E−04 | 1.10E−09 | 1.06E+05 | 1.19E−04 | 1.13E−09 |
| E2G4E10B7 | 2.43E+05 | 2.20E−04 | 9.06E−10 | 1.38E+05 | 1.61E−04 | 1.16E−09 |
| nivolumab | 2.37E+05 | 0.001998 | 8.45E−09 | 1.89E+05 | 0.001067 | 5.64E−09 |
| pembrolizumab | 8.29E+05 | 0.005048 | 6.09E−09 | 5.40E+05 | 9.55E−04 | 1.77E−09 |

TABLE 2-2

Binding affinities of Mouse Anti-PD-1 Monoclonal Antibodies to Mouse PD-1

| Mouse mAb | Kinetics on Biacore ™ Mouse PD-1-his | | |
|---|---|---|---|
| | $K_a$ ($M^{-1}s^{-1}$) | $K_d$ ($s^{-1}$) | $K_D$ (M) |
| E1G5D1H1 | / | / | No binding |
| E1A9C8A7 | 2.07E+05 | 0.03097 | 1.50E−07 |
| E2G4E10B7 | 1.86E+05 | 0.00553 | 2.98E−08 |
| nivolumab | / | / | No binding |
| pembrolizumab | / | / | No binding |

Example 3. Binding Activities of Mouse Anti-PD-1 Antibodies

The binding activities of mouse anti-PD1 antibodies of the disclosure to PD-1s were further determined by Capture ELISA, Indirect ELISA and Flow Cytometry (FACS).

3.1 Capture ELISA

Figure 1B:
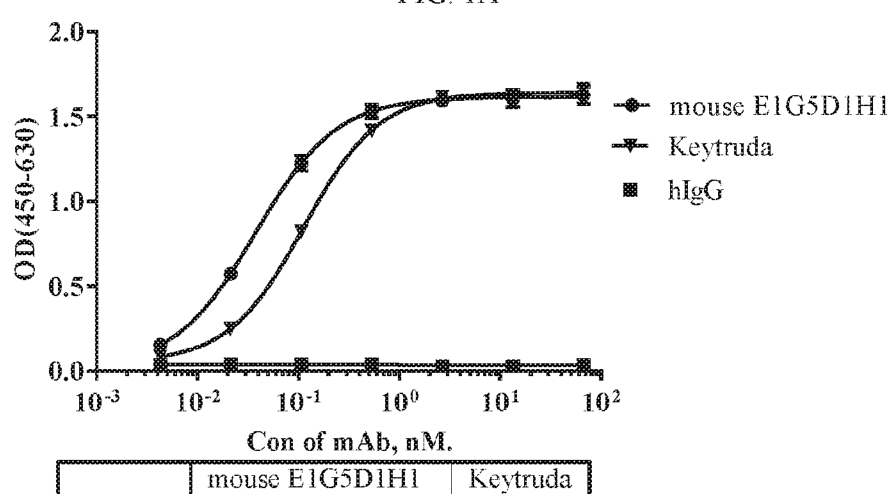

Briefly, 96-well micro plates were coated with 100 μl 2 μg/ml AffiniPure® Goat Anti-Mouse IgG $F(ab')_2$ fragment specific (Cat #:115-005-072, Jackson ImmunoResearch) or Goat-anti-human IgG (Cat #:109-005-097, Jackson ImmunoResearch, for the positive control and negative control) in PBS overnight at 4° C. Plates were washed once with wash buffer (PBST, PBS+0.05% polysorbate 20, i.e. Tween®-20) and then blocked with 200 μl/well blocking buffer (5% w/v non-fatty milk in PBST) for 2 hours at 37° C. Plates were washed again, respectively incubated with 100 μl/well serially diluted anti-PD1 antibodies of the disclosure, pembrolizumab, and a negative control hIgG (human immunoglobulin (pH4) for intravenous injection, Hualan Biological Engineering Inc.), 5-fold dilution in PBST with 2.5% non-fatty milk starting at 66.7 nM, for 40 minutes at 37° C., and then washed 4 times. Plates containing the captured anti-PD-1 antibodies were added and incubated with biotin-labeled human PD-1-Fc protein (in house made with SEQ ID NO: 26, 110 ng/mL in 2.5% non-fatty milk in PBST, 100 μl/well) for 40 minutes at 37° C., washed 4 times, and incubated with Peroxidase Streptavidin (1:10000 dilution in PBST, Cat #016-030-084, Jackson ImmunoResearch, 100 μl/well) for 40 minutes at 37° C. After a final wash, plates were incubated with 100 μl/well TMB (Cat #:TMB-S-002, Innoreagents) at room temperature. The reaction was stopped 3-10 minutes later with 50 μl/well 1M $H_2SO_4$, and the absorbance was read on a microplate reader using dual wavelength mode with 450 nm for TMB and 630 nm as the reference wavelength. The OD (450-630) values were plotted against antibody concentrations. Data was analyzed using GraphPad Prism® software and $EC_{50}$ values were reported. The results were shown in FIGS. 1A-1B.

3.2 Indirect ELISA

The anti-PD-1 antibodies of the disclosure were tested for their cross-reaction activities with cynomolgus PD-1 protein and mouse PD-1 protein.

Briefly, 96-well micro plates were coated with 100 μl 2 μg/ml mouse PD-1-his (Cat #:50124-M08H, Sino Biological Inc) or 2 μg/ml cynomolgus PD-1-his (Cat #:PD1-C5223, Acro biosystems Inc.) in carbonate/bicarbonate buffer (pH 9.6) for 2 hours at 37° C. Plates were washed once with wash buffer (PBST, PBS+0.05% polysorbate 20, i.e. Tween® 20) and then blocked with 200 μl blocking buffer (5% w/v non-fatty milk in PBST) for 2 hours at 37° C. Plates were washed again and incubated with 100 μl/well serially diluted anti-PD-1 antibodies of the disclosure or controls (starting at 66.7 nM, 5-fold serial dilution in 2.5% non-fatty milk in PBST) for 40 minutes at 37° C. ELISA plates were washed 4 times and incubated with Peroxidase AffiniPure® goat anti-mouse IgG, Fcγ Fragment Specific (1:5000 dilution in PBST buffer, Cat #:115-035-071, Jackson ImmunoResearch Laboratories, Inc., 100 μl/well) or Peroxidase AffiniPure@F(ab')$_2$ Fragment Goat Anti-Human IgG, Fcγ fragment specific (Cat #:109-036-098, Jackson ImmunoResearch, for the controls) for 40 minutes at 37° C. After a final wash, plates were incubated with 100 μl/well TMB (Cat #:TMB-S-002, Innoreagents) at room temperature. The reaction was stopped 3-10 minutes later with 50 μl/well 1M $H_2SO_4$, and the absorbance was read on a microplate reader using dual wavelength mode with 450 nm for TMB and 630 nm as the reference wavelength. Then the OD (450-630) values were plotted against antibody concentrations. Data was analyzed using GraphPad Prism® software and $EC_{50}$ values were reported. The results were shown in FIG. 2 and FIGS. 3A-3B.

3.3 Cell-Based Binding FACS

The binding activities of the mouse anti-PD-1 antibodies to mouse PD-1s expressed on cell surface were tested by flow cytometry (FACS), using Biosion in-house prepared 293F-mouse PD-1 cells expressing full length mouse PD-1 (SEQ ID NO.: 27) on cell membrane. The 293F-mouse PD-1 cells were prepared by transfecting 293F cells with a PCMV-T-P plasmid inserted with mouse PD-1 coding sequence between EcoRI and XbaI sites, following the instruction oflipofectamine 3000 transfection reagent (Thermo Fisher).

The mouse anti-PD-1 antibodies of the disclosure were also tested for their binding activities to human PD-1s expressed on cell surface by flow cytometry (FACS), using GS-J2/PD-1 cell line (Genscript) expressing cell-surface human PD-1s.

Figure 4A:
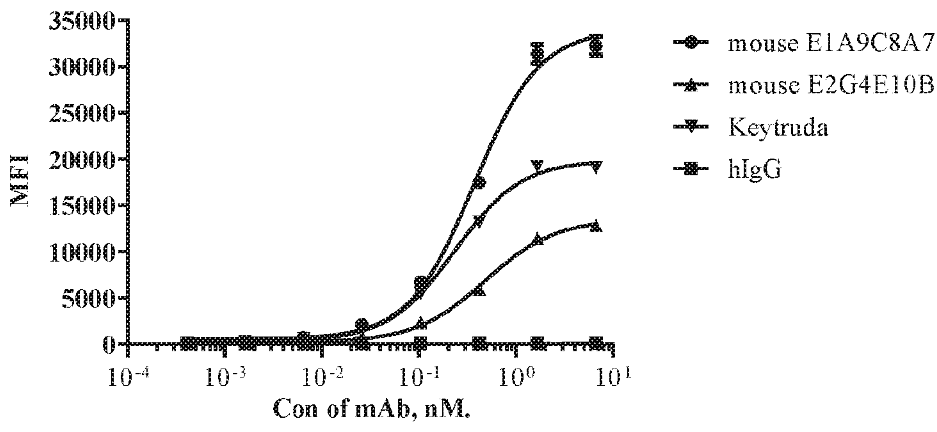
FIGS. 4A-4B show the binding capabilities of mouse antibodies E1A9C8A7 and E2G4E10B7 (A), and E1G5D1H1(B) to GS-J2/PD-1 cells expressing human PD-1 in a cell-based binding FACS assay.
Figure 4B:
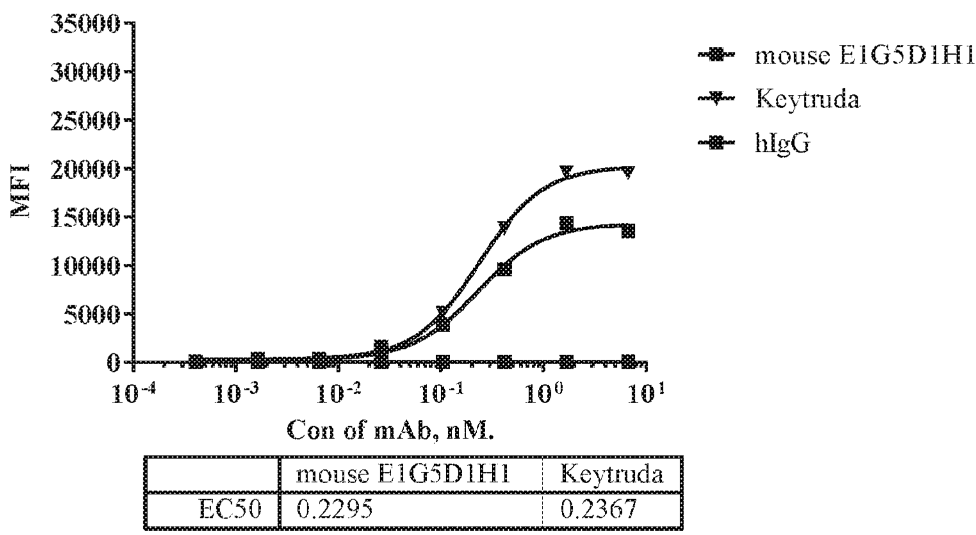

In specific, the 293F-mouse PD-1 cells and GS-J2/PD-1 cells were respectively harvested from cell culture flasks, washed twice and re-suspended in PBS containing 2% v/v Fetal Bovine Serum (FACS buffer). Then, $2\times10^5$ cells per well were incubated in 96 well-plates with 100 μl of the anti-PD1 antibodies or controls at various concentrations for 40 minutes on ice. Cells were washed twice with FACS buffer, and then added with 100 μl/well R-Phycoerythrin AffiniPure® F(ab')$_2$ Fragment Goat Anti-Mouse IgG (H+L) (1:1000 dilution in FACS buffer, Cat #:115-116-146, Jackson ImmunoResearch) for mouse monoclonal antibodies, or R-Phycoerythrin AffiniPure® Goat Anti-Human IgG, Fcγ fragment specific (Cat #:109-115-098, Jackson ImmunoResearch) for the controls. Following an incubation of 40 minutes at 4° C. in dark, cells were washed three times and re-suspended in FACS buffer. Fluorescence was measured using a Becton Dickinson (BD) FACSCanto™ II-HTS equipment and plotted against antibody concentrations. Data was analyzed using statistical analysis software GraphPad Prism® software and $EC_{50}$ values were reported. The results were shown in FIGS. 4A-4B and FIG. 5.

It can be seen from FIGS. 1A-1B and 4A-4B that the mouse anti-PD1 antibodies of the disclosure specifically bound to human PD-1 with comparable or higher Bmax (maximal binding) and comparable or lower $EC_{50}$ compared to pembrolizumab.

Figure 3A:
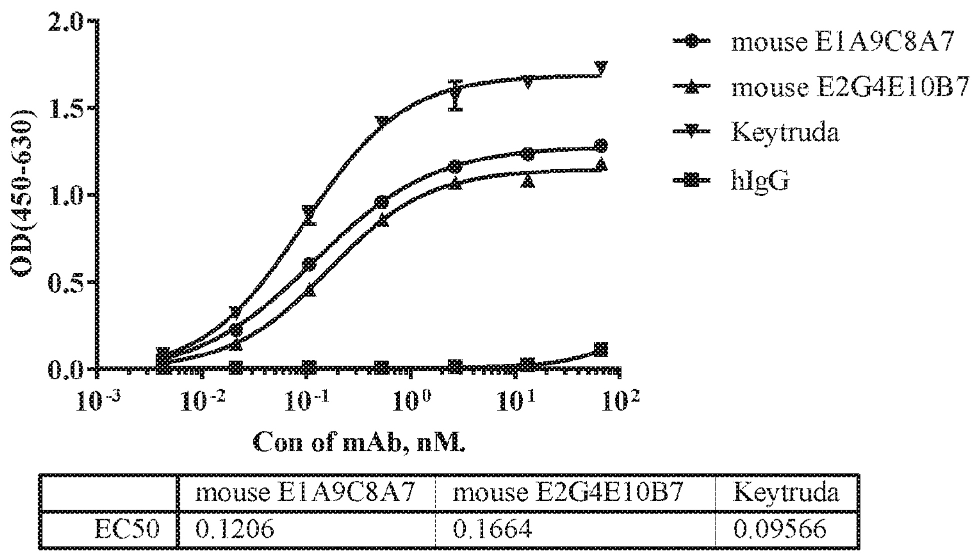
FIGS. 3A-3B show the binding capabilities of mouse antibodies E1A9C8A7 and E2G4E10B7 (A), and EIG5D1H1 (B) to cynomolgus PD-1 in an indirect ELISA.
Figure 3B:
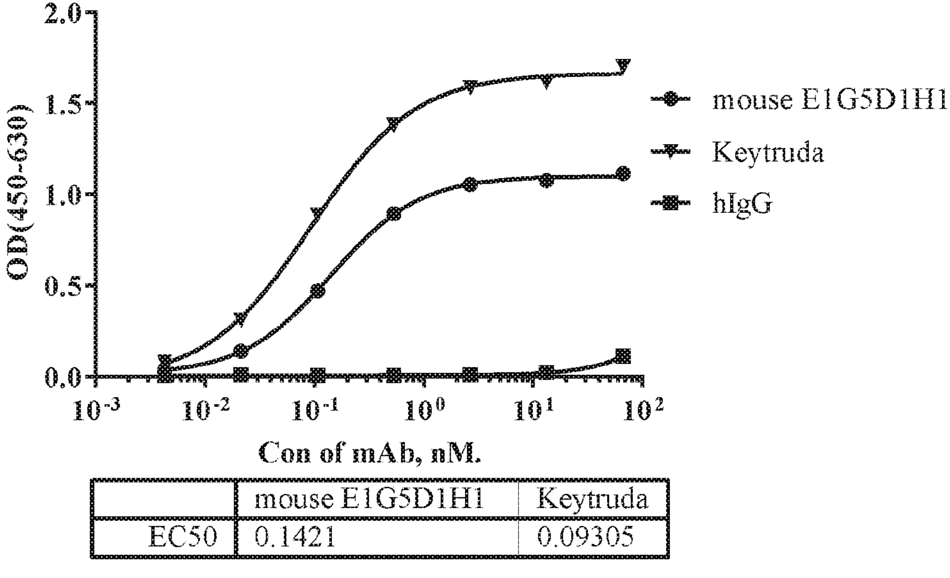

The antibodies of the disclosure bound to cynomolgus PD-1, as shown in FIGS. 3A-3B, with lower Bmax and higher $EC_{50}$ compared to pembrolizumab.

Figure 2:
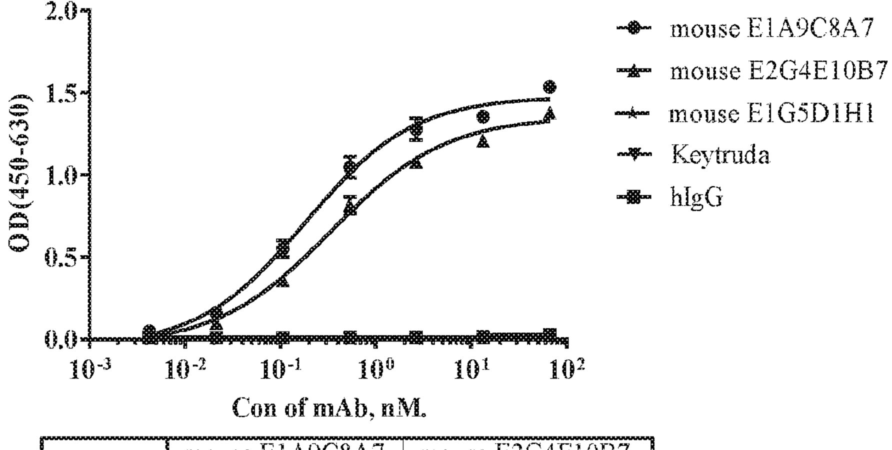
FIG. 2 shows the binding capabilities of mouse antibodies E1A9C8A7, E2G4E10B7 and E1G5D1H1 to mouse PD-1 in an indirect ELISA.
Figure 5:
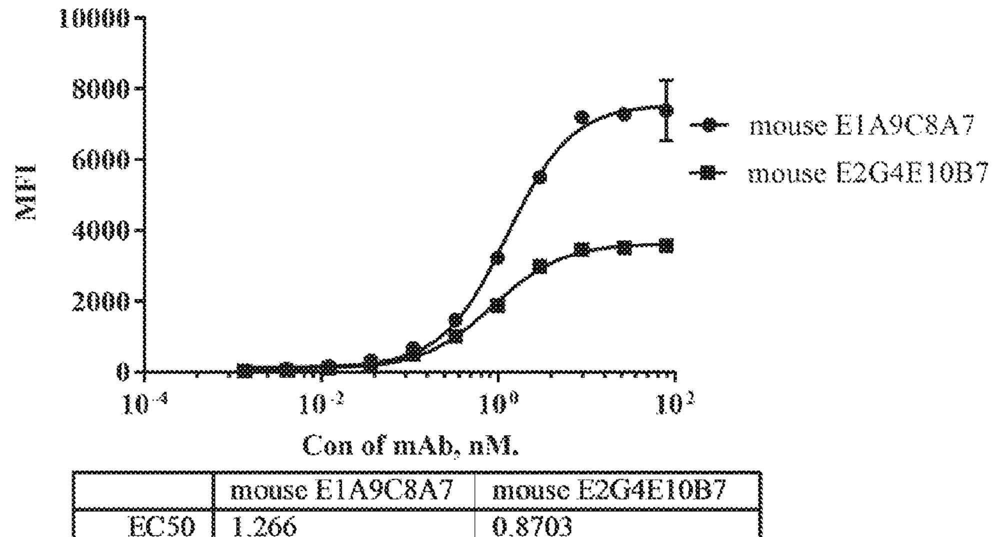
FIG. 5 shows the binding capabilities of mouse antibodies E1A9C8A7 and E2G4E10B7 to 293F-mouse PD-1 cells expressing mouse PD-1 in a cell-based binding FACS assay.

According to FIG. 2 and FIG. 5, the mouse antibodies E1A9C8A7 and E2G4E10B7 specifically bound to mouse PD-1, while pembrolizumab did not.

Example 4. Blocking Activities of Mouse Anti-PD1 Antibodies on PD-1-PD-L1 or PD-1-Benchmark Binding 4.1 Ligand Blocking ELISA The activities of the anti-PD1 antibodies of the disclosure to block PD-L1-PD1 binding were measured in a competitive ELISA.

Figure 6A:
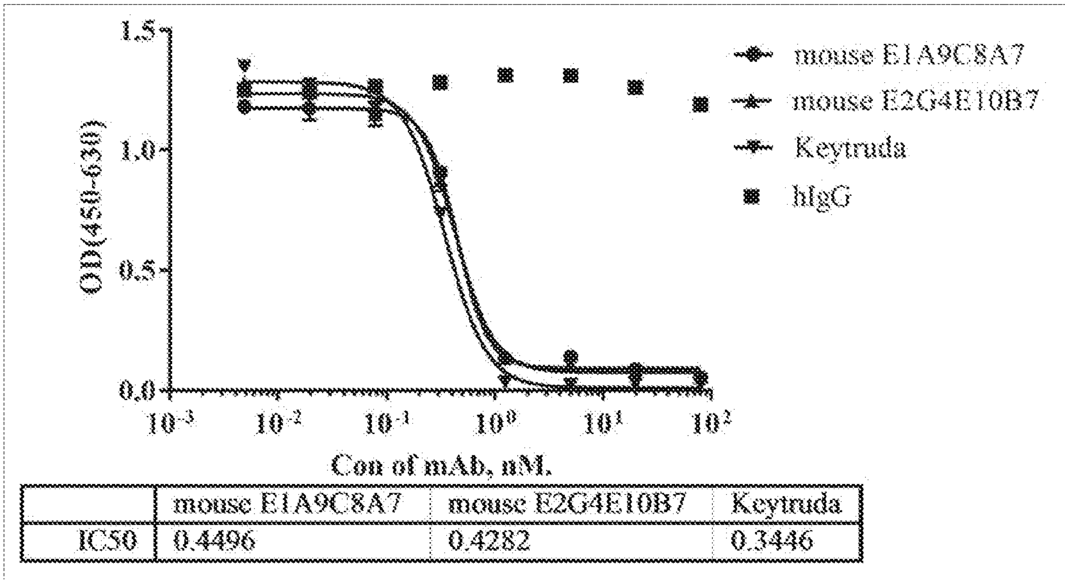
FIGS. 6A-6B show the abilities of mouse antibodies E1A9C8A7 and E2G4E10B7 (A), and E1G5D1H1 (B) to block human PD-1-human PD-L1 binding in a competitive ELISA.
Figure 6B:
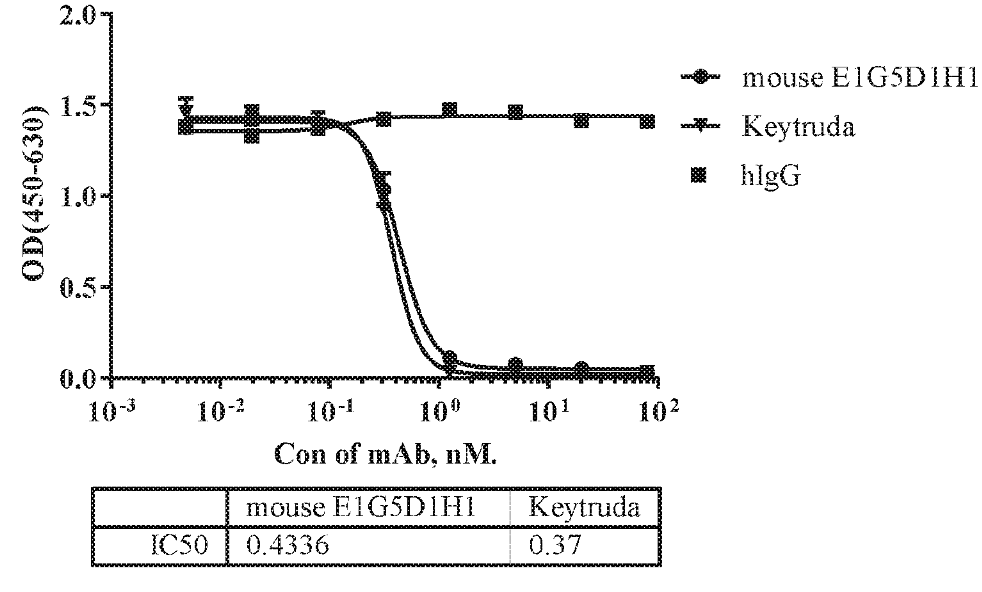

Briefly, 100 μl human PD-L1-Fc protein (prepared in-house with SEQ ID NO: 28) at 2 μg/mL in carbonate/bicarbonate buffer (pH 9.6) was coated on 96-well micro plates overnight at 4° C. Plates were washed with wash buffer (PBS+0.05% w/v polysorbate 20, i.e. Tween® 20, PBST), and blocked with 5% w/v non-fatty milk in PBST for 2 hours at 37° C. The anti-PD1 antibodies of the disclosure or controls were diluted with biotin labeled human PD-1-Fc protein (prepared in-house with SEQ ID NO: 26, 137.5 ng/mL in PBST with 2.5% non-fatty milk), starting at 80 nM with a 4-fold serial dilution, and incubated at room temperature for 40 minutes. After plate washing, the antibody/human PD-1-Fc mixtures were added to human PD-L1-Fc coated plates, 100 μl per well. After incubation at 37° C. for 40 minutes, plates were washed using wash buffer. Then the plates were added with 100 μl/well Peroxidase Streptavidin (1:10000 dilution in PBST buffer, Cat #:016-030-084, Jackson Immunoresearch) and incubated for 40 minutes at 37° C. to detect biotin labeled human PD-1-Fc. Plates were washed again using wash buffer. Finally, TMB was added and the reaction was stopped using 1M $H_2SO_4$. The absorbance was read on a microplate reader using dual wavelength mode with 450 nm for TMB and 630 nm as the reference wavelength, then the OD (450-630) values were plotted against antibody concentrations. Data was analyzed using Graphpad Prism® software and $IC_{50}$ values were reported. The results were shown in FIGS. 6A-6B.

4.2 Cell-based Ligand Blocking FACS

The activities of the antibodies of the disclosure to block human PD-1-Fc protein binding to cell surface PD-L1 were evaluated by Flow Cytometry (FACS), using the cell line GS-C2/PD-L1 (Genscript) expressing cell-surface human PD-L1.

Figure 7A:
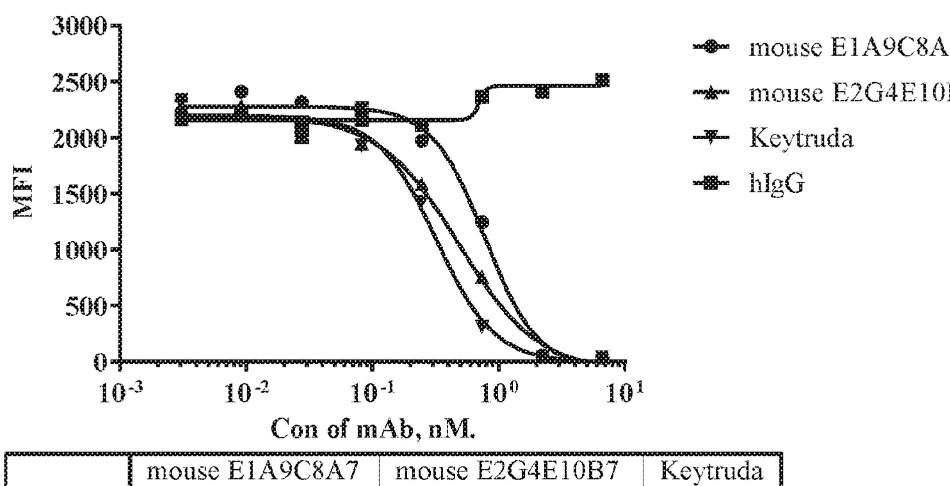
FIGS. 7A-7B show the abilities of mouse antibodies E1A9C8A7 and E2G4E10B7 (A), and E1G5D1H1 (B) to block human PD-1 binding to cell surface human PD-L1 in a cell-based blocking FACS assay.
Figure 7B:
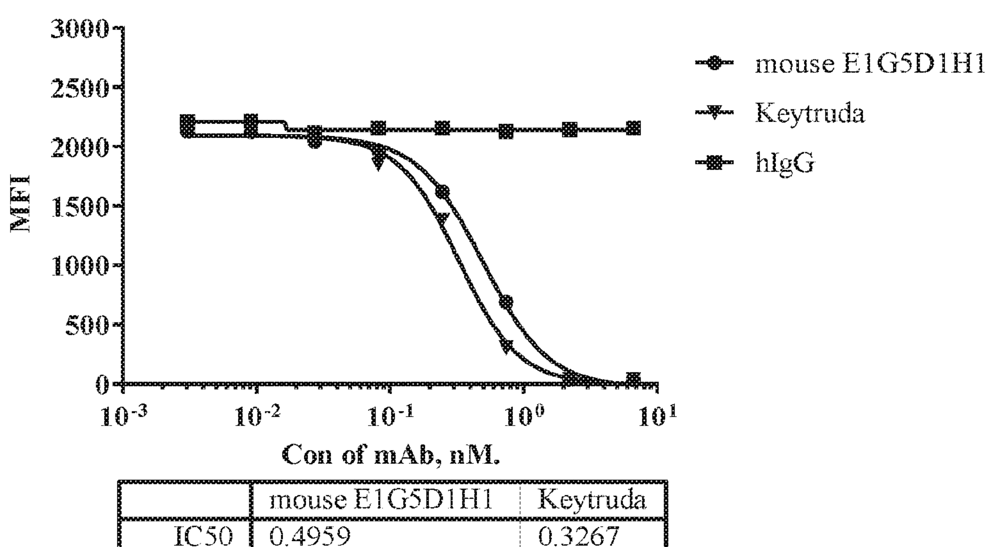

The anti-PD1 antibodies of the disclosure, and the controls were diluted with biotin labeled human PD-1-Fc solution (prepared in-house with SEQ ID NO: 26, 137.5 ng/mL in FACS buffer), 3-fold serial dilution starting at 6.67 nM, and incubated at room temperature for 40 minutes. GS-C2/PDL1 cells were harvested from cell culture flasks at the log phase, washed twice and re-suspended in PBS containing 2% v/v Fetal Bovine Serum (FACS buffer). GS-C2/PD-L1 cells, $0.6\times10^5$ cells per well, were incubated in 96 well-plates with 100 l/well the antibody/PD1-Fc mixture for 40 minutes at 4° C. Cells were washed twice with FACS buffer, added with 100 μl/well R-Phycoerythrin Streptavidin (1:500 dilution in FACS buffer, Cat #:016-110-084, Jackson Immunoresearch), and incubated for 40 minutes at 4° C. in dark. Cells were washed twice and re-suspended in FACS buffer. Fluorescence was measured using a BD FACSCanto™ II-HTS equipment. Data was analyzed using Graphpad Prism® software and $IC_{50}$ values were reported. The results were shown in FIGS. 7A-7B.

The activities of the anti-PD1 antibodies to block mouse PD-L1 binding to cell surface mouse PD-1 were evaluated by Flow Cytometry (FACS), using the 293F-mouse PD-1 cells described above.

Figure 8:
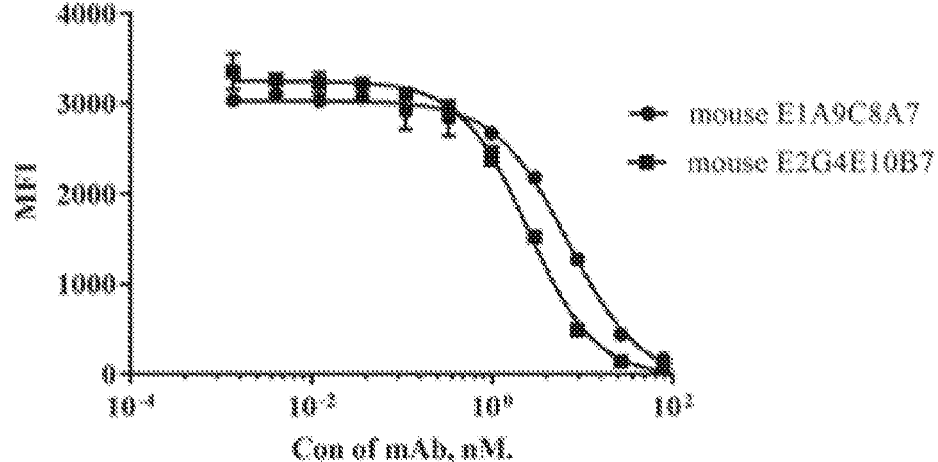
FIG. 8 shows the abilities of mouse antibodies E1A9C8A7 and E2G4E10B7 to block mouse PD-L1 binding to cell surface mouse PD-1 in a cell-based blocking FACS assay.

Briefly, 293F-mouse PD-1 cells were harvested from cell culture flasks, washed twice and re-suspended in PBS containing 2% v/v Fetal Bovine Serum (FACS buffer). Then, $1\times10^5$ cells per well in 96 well-plates were incubated in 100 µL of the anti-PD-1 antibodies or controls at various concentrations (starting at 80 nM with a 3-fold serial dilution) in FACS buffer for 40 minutes at 4° C. The plates were washed twice with FACS buffer, and added and incubated for 40 minutes at 4° C. with 100 µl/well recombinant mouse PD-L1-hFc protein (Cat #:50010-M03H, Sino biological Inc., 1 µg/mL in FACS buffer). The plates were washed twice with FACS buffer, and then added and incubated for 40 minutes at 4° C. in dark with 100 µl/well R-Phycoerythrin AffiniPure® Goat Anti-Human IgG, Fey fragment specific (1:1000 dilution in FACS buffer, Cat #:109-115-098, Jackson Immunoresearch). Cells were washed twice and resuspended in FACS buffer. Fluorescence was measured using a BD FACSCanto™ II-HTS equipment. Data was analyzed using Graphpad Prism® software and $IC_{50}$ values were reported. The results were shown in FIG. 8.

4.3 Benchmark Blocking ELISA

The abilities of the anti-PD1 antibodies of the disclosure to block benchmark (Keytruda® pembrolizumab) binding to human PD-1-Fc protein were measured in a competitive ELISA assay. Briefly, 100 µl 2 µg/mL pembrolizumab in PBS was coated on 96-well micro plates for 2 hours at 37° C. ELISA plates were washed once with wash buffer (PBST, PBS+0.05% polysorbate 20, i.e. Tween®-20) and then blocked with 200 µl/well blocking buffer (5% w/v non-fatty milk in PBST) for 2 hours at 37° C. While blocking, the anti-PD-1 antibodies of the disclosure or controls were diluted with biotin labeled human PD-1-Fc protein (prepared in-house with SEQ ID NO: 26, 11 ng/ml in 2.5% non-fatty milk in PBST), starting at 80 nM with a 4-fold serial dilution, and incubated at room temperature for 40 minutes. After plate washing, the antibody/PD-1 protein mixtures were added to benchmark coated plates, 100 µl per well. After incubation at 37° C. for 40 minutes, plates were washed using wash buffer, added and incubated with 100 µl/well Peroxidase Streptavidin for 40 minutes at 37° C. Plates were washed again using wash buffer. Finally, TMB was added and the reaction was stopped using 1M $H_2SO_4$. The absorbance was read on a microplate reader using dual wavelength mode with 450 nm for TMB and 630 nm as the reference wavelength, and the OD (450-630) values were plotted against antibody concentrations. Data was analyzed using Graphpad Prism® software and $IC_{50}$ values were reported. The results were shown in FIGS. 9A-9B.

It can be seen from FIGS. 6A-6B and 7A-7B that the anti-PD-1 antibodies of the disclosure were capable of blocking human PD-1 binding to human PD-L1, with comparable or a bit lower activities than pembrolizumab. According to FIG. 8, antibodies E1A9C8A7 and E2G4E10B7 blocked mouse PD-L1 binding to cell surface mouse PD-1, with high blocking activities, this was distinct from pembrolizumab which was not able to bind mouse PD-1.

Figure 9A:
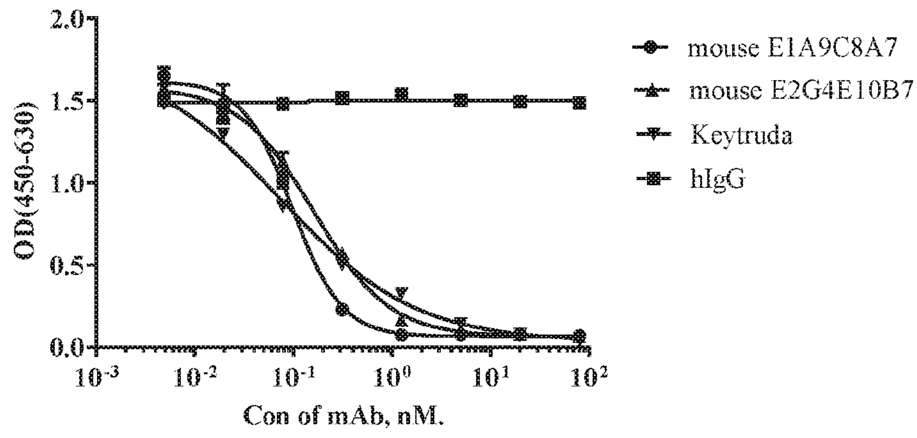
FIGS. 9A-9B show the abilities of mouse antibodies E1A9C8A7 and E2G4E10B7 (A), and E1G5D1H1 (B) to block pembrolizumab-PD-1 binding in a competitive ELISA test.
Figure 9B:
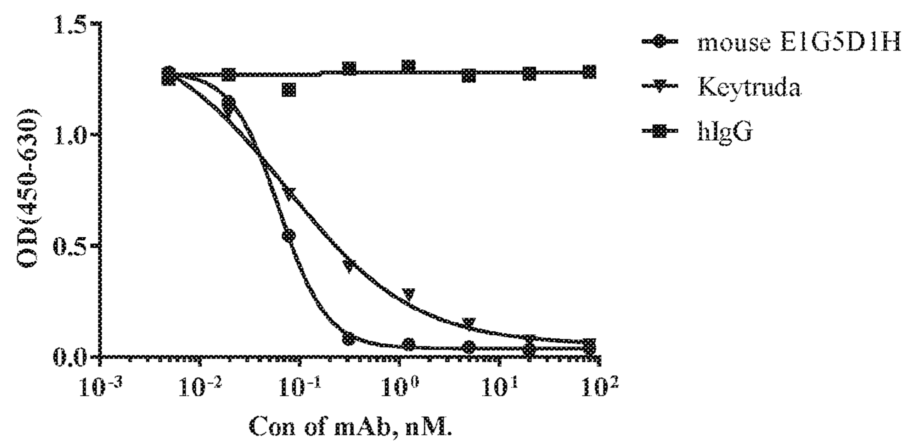

FIGS. 9A-9B showed that the anti-PD-1 antibodies of the disclosure were able to block PD-1 binding to pembrolizumab, suggesting that these antibodies might bind to the same or similar epitopes as pembrolizumab did.

Example 5. Cell Based Functional Assay of Mouse Anti-PD-1 Antibodies

The activities of the antibodies of the disclosure to block the interaction of cell membrane PD-1 with cell membrane PD-L1 were evaluated in a cell-based functional assay, using two genetically engineered cell lines, GS-J2/PD-1 (Genscript, effector cell line) described above stably expressing human PD-1 and a luciferase reporter driven by an NFAT response element (NFAT-RE), and GS-C2/PD-L1 (Genscript, antigen presenting cells) stably expressing human PD-L1 and an engineered cell surface antigenic peptide/major histocompatibility complex (MHC). When these two cell lines were co-cultured, the T-cell receptor (TCR)-NFAT-mediated luciferase expression in GS-J2/PD-1 cells would be inhibited or reduced by PD-1-PD-L1 interaction.

The cell-based functional assay was carried out as follows. Briefly, $1.0\times10^4$ GS-C2/PD-L1 cells at the log phase in 20 µL RPMI1640 medium (Cat #:12430-054, Gibco) supplemented with 10% FBS (Cat #:10099-141, Gibco) were seeded onto 384-well cell culture plates (Cat #:3765, Corning®). The next day, serially diluted anti-PD-1 antibodies of the disclosure or controls (including an in house made anti-CD22 antibody as negative control) in assay buffer (RPMI1640+1% FBS), 5-fold serial dilution starting from 300 nM, were prepared. After the culture medium were discarded, the 384-well plates were added with 20 µl of the diluted anti-PD1 antibodies and 20 µl of GS-J2/PD-1 effector cells ($7.5\times10^5$/ml). After co-cultured at 37° C. in an incubator for 6 hours, the plates were added with Luciferase detection Reagent (30 µL/well, Cat #:E6120, Promega). Ten minutes later, the plates were subject to analysis in Tecan infinite 200Pro plate-reader. Luminescence signals were analyzed using Graphpad Prism® software and $EC_{50}$ values were reported.

Figure 10:
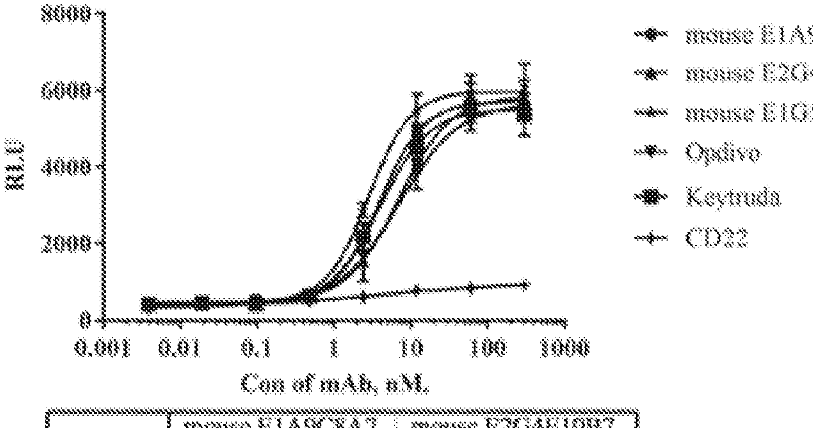
FIG. 10 shows the capabilities of mouse antibodies E1A9C8A7, E2G4E10B7 and E1G5D1H1 to reverse PD-1-PD-L1 interaction induced luciferase expression decrease in a cell-based functional assay.

The result was shown in FIG. 10.

It can be seen that all anti-PD1 antibodies of the disclosure were able to reverse the PD-1-PD-L1 interaction induced luciferase expression decrease in GS-J2/PD-1 cells more efficiently than nivolumab, but at comparable activities to pembrolizumab.

Example 6. Generation and Characterization of Chimeric Antibodies

The heavy/light chain variable regions of the anti-PD-1 mAbs of the disclosure were sequenced, and the sequence ID numbers were summarized in Table 1.

The heavy and light chain variable regions of the anti-PD1 mouse mAb E1A9C8A7 were cloned in frame to human IgG4 heavy-chain constant region (SEQ ID NO.: 24) and human kappa light-chain constant region (SEQ ID NO.: 25), respectively, wherein the C terminus of variable region was linked to the N terminus of the respective constant region.

The vectors each containing a nucleotide encoding a heavy chain variable region linked to human IgG4 heavy-chain constant region, and the vectors each containing a nucleotide encoding a light chain variable region linked to human kappa light-chain constant region were transiently transfected into 50 ml of 293F suspension cell cultures at a ratio of 1.1:1 light to heavy chain construct, with 1 mg/mL PEI.

Cell supernatants containing chimeric antibodies were harvested after six days in shaking flasks, and then chimeric antibodies were purified from cell supernatants. The purified chimeric antibodies were tested in the Biacore™ affinity test and cell-based functional assay following the protocols in the foregoing Examples.

Figure 11:
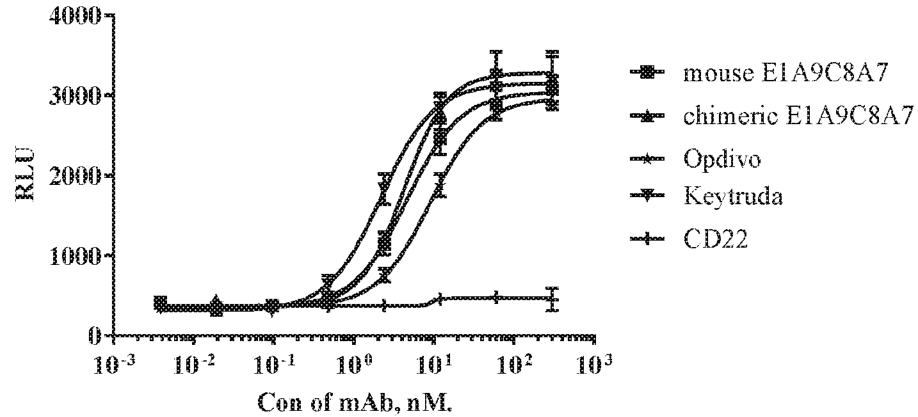
FIG. 11 shows the capability of chimeric E1A9C8A7 antibody to reverse PD-1-PD-L1 interaction induced luciferase expression decrease in a cell-based functional assay.
Figure 12:
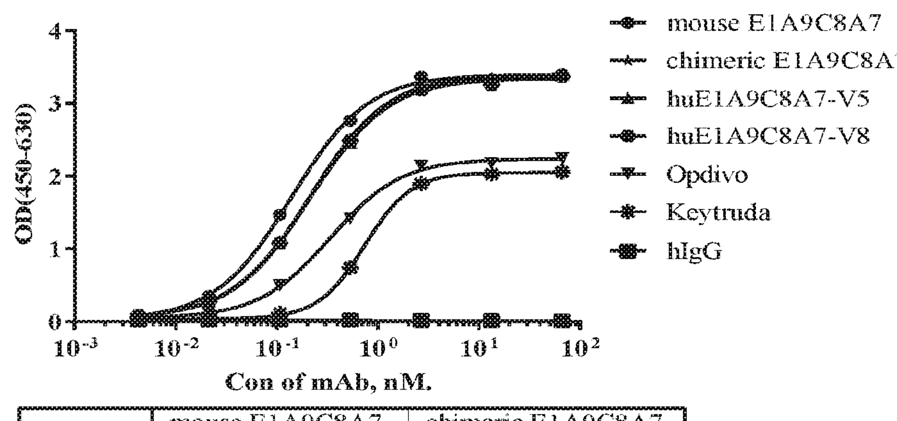
FIG. 12 shows the binding capabilities of humanized antibodies huE1A9C8A7-V5 and huE1A9C8A7-V8 to human PD-1 in a capture ELISA.
Figure 13:
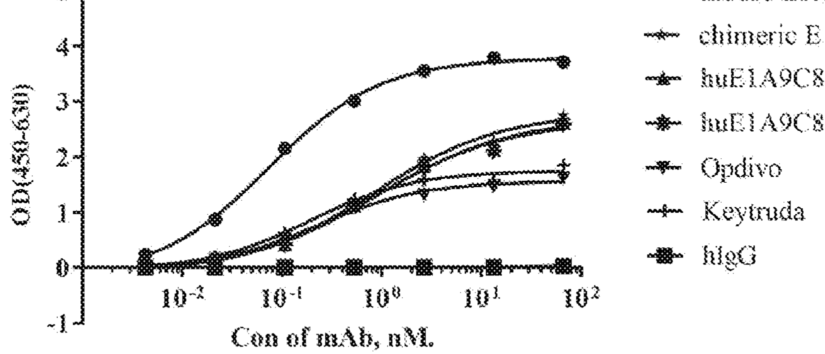
FIG. 13 shows the binding capabilities of humanized antibodies huE1A9C8A7-V5 and huE1A9C8A7-V8 to cynomolgus PD-1 in an indirect ELISA.
Figure 14:
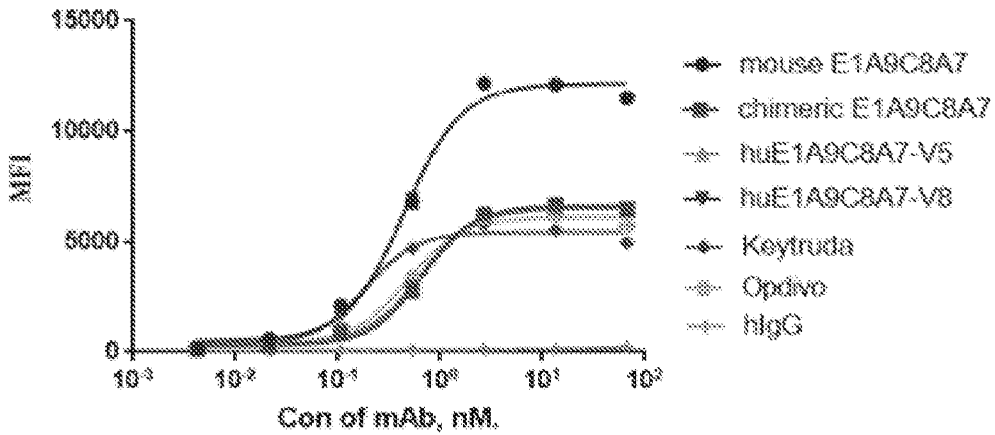
FIG. 14 shows the binding capabilities of humanized antibodies huE1A9C8A7-V5 and huE1A9C8A7-V8 to GS-J2/PD-1 cells expressing human PD1 in a cell-based binding FACS assay.
Figure 15:
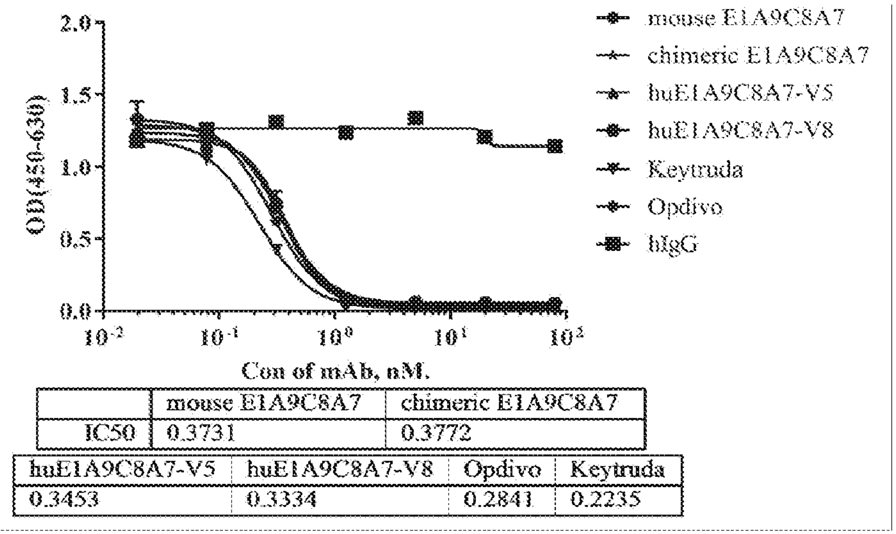
FIG. 15 shows the abilities of humanized antibodies huE1A9C8A7-V5 and huE1A9C8A7-V8 to block human PD-1-PD-L1 binding in a competitive ELISA test.
Figure 16:
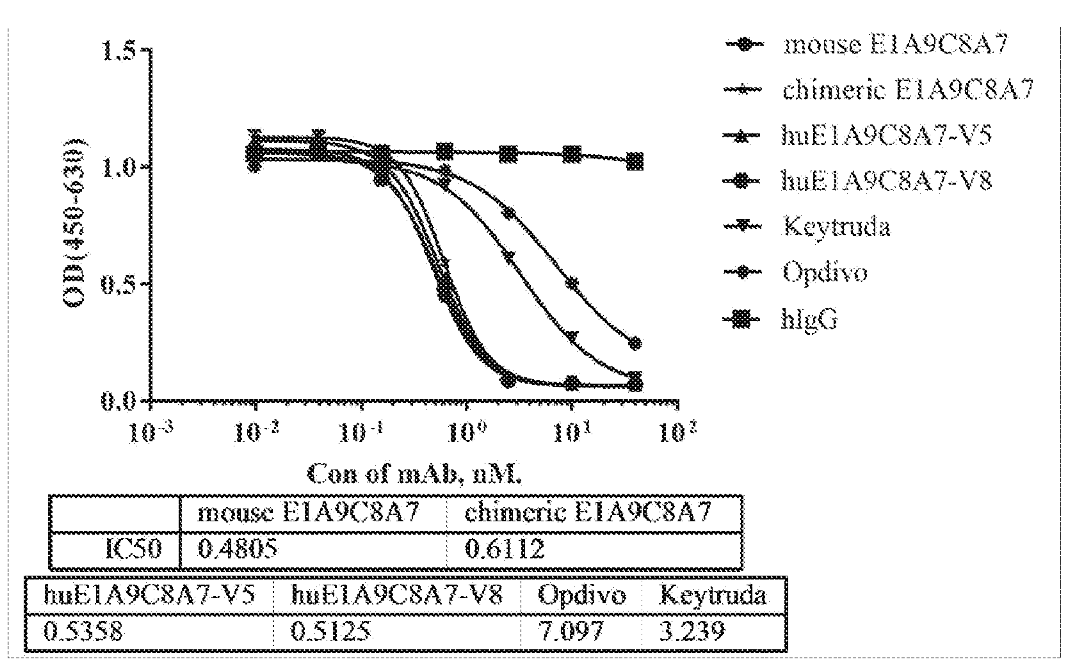
FIG. 16 shows the abilities of humanized antibodies huE1A9C8A7-V5 and huE1A9C8A7-V8 to block pembrolizumab-PD-1 binding in a competitive ELISA test.

The results were shown in Table 3 and FIG. 11.

The binding affinity data in Table 3 showed that the chimeric antibody E1A9C8A7 had high binding affinity to human PD-1.

According to FIG. 11, the chimeric antibody E1A9C8A7 was able to reverse the PD-1-PD-L1 interaction induced luciferase expression decrease in GS-J2/PD-1 cells more efficiently than nivolumab but at comparable activity to pembrolizumab.

TABLE 3

Binding affinity of Chimeric Anti-PD1 Antibody

| | Kinetics on Biacore ™ | | | | | |
|---|---|---|---|---|---|---|
| | Human PD1-his | | | Mouse PD1-his | | |
| mAb | $K_a$ ($M^{-1}s^{-1}$) | $K_d$ ($s^{-1}$) | $K_D$ (M) | $K_a$ ($M^{-1}s^{-1}$) | $K_d$ ($s^{-1}$) | $K_D$ (M) |
| Chimeric E1A9C8A7 | 5.80E+05 | 6.45E−04 | 1.11E−09 | 1.67E+05 | 0.02704 | 1.62E−07 |

Example 7. Humanization of Anti-PD1 Monoclonal Antibody E1A9C8A7

Mouse anti-PD-1 antibody E1A9C8A7 was humanized and further characterized. Humanization was conducted using the well-established CDR-grafting method as described in detail below.

To select acceptor frameworks for humanization of the mouse antibody E1A9C8A7, the light and heavy chain variable region sequences of mouse E1A9C8A7 antibody were blasted against the human immunoglobulin gene database. The human germlines with the highest homology were selected as the acceptor frameworks for humanization. The mouse antibody heavy/light chain variable region CDRs were inserted into the selected frameworks, and the residue(s) in the frameworks was/were further back-mutated to obtain more candidate heavy chain/light chain variable regions. A total of 11 exemplary humanized E1A9C8A7 antibodies, namely huE1A9C8A7-V1 to huE1A9C8A7-V 11 were obtained, whose heavy/light chain variable region sequence ID numbers were set forth in Table 1.

The vectors each containing a nucleotide encoding a humanized heavy chain variable region linked to human IgG4 heavy-chain constant region (SEQ ID NO: 24), and the vectors each containing a nucleotide encoding humanized light chain variable region linked to human kappa light-chain constant region (SEQ ID NO: 25) were transiently transfected into 50 ml of 293F suspension cell cultures in a ratio of 1.1:1 light to heavy chain construct, with 1 mg/mL PEI.

Example 8. Characterization of Humanized E1A9C8A7 Antibodies

Cell supernatants containing humanized E1A9C8A7 antibodies were harvested after six days in shaking flasks and tested for binding affinities to human PD-1 by Octet system (Fortebio, Octet RED 96).

Briefly, AHC biosensors (anti-human IgG Fc capture, from ForteBio) were presoaked with 10 mM glycine (pH 1.5) for 3 seconds, and then dipped in a well with running buffer (0.5% w/v BSA in PBST) for 3 seconds, the soaking and dipping steps were repeated for three times. Then, the sensors were respectively dipped in wells with cell supernatants containing humanized anti-PD-1 antibodies, the chimeric E1A9C8A7 antibody in HBS-$EP^+$ at 2 μg/ml, and nivolumab in HBS-$EP^+$ at 2 μg/ml for 200 seconds, and then immersed in a well with running buffer for 1 min. A new baseline was run for 100 seconds in another well with running buffer. Then the sensors were dipped in a well with serially diluted human PD-1-his protein (Cat #:PD1-H5221, Acro biosystems Inc., starting at 100 nM with a two-fold serial dilution) in running buffer for 120 seconds, and then immersed in a baseline well for 4 min. Finally, sensors were presoaked with 10 mM glycine (pH 1.5) for 30 seconds, and then were dipped in a well with running buffer for 30 seconds. The association and dissociation curves were fit to a 1:1 Langmuir binding model using ForteBio Data Analysis 8.1 evaluation software. The $K_a$, $K_d$ and $K_D$ values were determined and summarized in Table 4 below.

TABLE 4

Binding Affinities of Humanized E1A9C8A7 mAbs

| | Kinetics on Octet Human PD1-his | | |
|---|---|---|---|
| mAb | $K_a$ (M−1s−1) | $K_d$ (s−1) | $K_D$ (M) |
| Chimeric E1A9C8A7 | 2.39E+05 | 3.16E−04 | 1.32E−09 |
| huE1A9C8A7-V1 | 2.06E+05 | 3.17E−04 | 1.54E−09 |
| huE1A9C8A7-V2 | 1.97E+05 | 2.94E−04 | 1.49E−09 |
| huE1A9C8A7-V3 | / | / | No binding |
| huE1A9C8A7-V4 | 1.82E+05 | 2.70E−04 | 1.49E−09 |
| huE1A9C8A7-V5 | 2.11E+05 | 2.13E−04 | 1.01E−09 |
| huE1A9C8A7-V6 | 2.33E+05 | 4.28E−04 | 1.84E−09 |
| nivolumab | 2.02E+05 | 1.92E−03 | 9.51E−09 |
| Chimeric E1A9C8A7 | 2.74E+05 | 5.97E−04 | 2.18E−09 |
| huE1A9C8A7-V7 | 2.37E+05 | 3.56E−04 | 1.50E−09 |
| huE1A9C8A7-V8 | 2.58E+05 | 2.91E−04 | 1.13E−09 |
| huE1A9C8A7-V9 | 2.53E+05 | 4.13E−04 | 1.63E−09 |
| huE1A9C8A7-V10 | 2.42E+05 | 3.85E−04 | 1.59E−09 |
| huE1A9C8A7-V11 | 1.94E+05 | 2.96E−04 | 1.53E−09 |
| nivolumab | 2.04E+05 | 2.15E−03 | 1.05E−08 |

The data indicated that all cell supernatants containing humanized PD1 antibodies, except huE1A9C8A7-V3, had similar human PD-1 binding affinities to the chimeric antibody, but higher than that of nivolumab.

The humanized antibodies huE1A9C8A7-V5 and huE1A9C8A7-V8 were purified as described above and tested in Biacore™, Capture ELISA, Indirect ELISA, Competitive ELISA, cell-based binding FACS, cell-based ligand-blocking FACS and cell-based functional assay, following the protocols in the foregoing Examples with minor modifications described below.

For the capture ELISA, 96-well plates were coated with 100 μl 2 μg/ml AffiniPure® Goat Anti-Human IgG, Fcγ fragment specific (Cat #:109-005-098, Jackson Immunoresearch) instead of AffiniPure® goat-anti-mouse IgG $F(ab')_2$ fragment specific. Biotin labeled human PD-1-his protein (prepared in-house with SEQ ID NO: 29), 39.2 ng/ml in PBST with 2.5% non-fatty milk, were used instead of biotin labeled human PD-1-Fc, 100 μl/well.

For the Indirect ELISA, Peroxidase AffiniPure® $F(ab')_2$ Fragment Goat Anti-Human IgG, Fey fragment specific (Cat #:109-036-098, Jackson Immunoresearch) was used for the humanized antibodies, 100 μl/well.

For the Biacore™ test, goat anti-human IgG (Cat #:BR100839, GE healthcare, Human Antibody Capture Kit) was covalently linked to the CM5 chip.

For the benchmark blocking ELISA, the biotin labeled human PD-1-his protein (prepared in-house with SEQ ID NO: 29, 15.7 ng/ml in PBST with 2.5% non-fatty milk) were used instead of biotin labeled human PD-1-Fc solution, 100 μl/well.

For the cell-based binding FACS, R-Phycoerythrin AffiniPure® Goat Anti-human IgG Fcγ fragment specific (Cat #:109-115-098, Jackson ImmunoResearch) was used for the humanized antibodies, with 1:1000 dilution in FACS buffer, 100 μl/well.

The humanized antibodies huE1A9C8A7-V5 and huE1A9C8A7-V8 were also tested for their thermal stabilities. Briefly, a protein thermal shift assay was used to determine Tm (melting temperature) using a GloMelt™ Thermal Shift Protein Stability Kit (Cat #:33022-T, Biotium). Briefly, the GloMelt™ dye was allowed to thaw and reach room temperature. The vial containing the dye was vortexed and centrifuged. Then, 10× dye was prepared by adding 5 μL 200× dye to 95 μL PBS. 2 μL 10× dye and 10 μg humanized antibodies were added, and PBS was added to a total reaction volume of 20 μL. The tubes containing the dye and antibodies were briefly spun and placed in real-time PCR thermocycler (Roche, LightCycler® 480 II) set up with a melt curve program having the parameters in Table 5.

TABLE 5

Parameters for Melt Curve Program

| Profile step | Temperature | Ramp rate | Holding Time |
|---|---|---|---|
| Initial hold | 25° C. | NA | 30 s |
| Melt curve | 25-99° C. | 0.1° C./s | NA |

The results were shown in Tables 6-1 and 6-2, FIGS. 12-18 and 19A-19B.

TABLE 6-1

Binding affinities/capacities of Humanized mAbs huE1A9C8A7-V5 and huE1A9C8A7-V8

| | Binding assay | | | | | |
|---|---|---|---|---|---|---|
| | Human PD1 | | Cynomolgus PD1 | | Mouse | Cell |
| mAb ID# | Capture ELISA ($EC_{50}$, nM) | Biacore ™ ($K_D$, nM) | Indirect ELISA ($EC_{50}$, nM) | Biacore ™ ($K_D$, nM) | PD1 Biacore ™ ($K_D$, nM) | Binding FACS ($EC_{50}$, nM) |
| Mouse E1A9C8A7 | 0.14 | * | 0.07 | * | * | 0.44 |
| Chimeric E1A9C8A7 | 0.21 | * | 0.85 | * | * | 0.67 |
| huE1A9C8A7-V5 | 0.21 | 8.60E−10 | 0.90 | 1.22E−09 | 1.58E−07 | 0.66 |
| huE1A9C8A7-V8 | 0.21 | 8.22E−10 | 0.82 | 1.17E−09 | 1.39E−07 | 0.63 |
| pembrolizumab | 0.74 | 4.29E−09 | 0.20 | 1.42E−09 | No Binding | 0.18 |
| nivolumab | 0.34 | 3.35E−09 | 0.23 | 3.54E−09 | No Binding | 0.47 |

*Not tested.

TABLE 6-2

Functional activities of Humanized mAbs huE1A9C8A7-V5 and huE1A9C8A7-V8

| | Competitive ELISA ($IC_{50}$, nM) | | Cell-based | | | |
|---|---|---|---|---|---|---|
| | PD1-PDL1 blocking | Pembrolizumab-PD1 blocking | ligand blocking FACS | Cell-based functional assay | Tm (melting temperature), ° C. | |
| mAb ID# | ELISA | ELISA | ($IC_{50}$, nM) | ($EC_{50}$, nM) | T1 | T2 |
| Mouse E1A9C8A7 | 0.37 | 0.48 | 0.42 | 6.62 | * | * |
| Chimeric E1A9C8A7 | 0.38 | 0.61 | 0.57 | 7.45 | * | * |
| huE1A9C8A7-V5 | 0.35 | 0.54 | 0.54 | 9.30 | 66 | 76.5 |
| huE1A9C8A7-V8 | 0.33 | 0.51 | 0.55 | 5.13 | 66 | 76.5 |
| pembrolizumab | 0.22 | 3.24 | 0.49 | 2.61 | * | * |
| nivolumab | 0.28 | 7.10 | 0.52 | 8.03 | * | * |

TABLE 6-2-continued

Functional activities of Humanized mAbs huE1A9C8A7-V5 and huE1A9C8A7-V8

| mAb ID# | Competitive ELISA ($IC_{50}$, nM) PD1-PDL1 blocking ELISA | Pembrolizumab-PD1 blocking ELISA | Cell-based ligand blocking FACS ($IC_{50}$, nM) | Cell-based functional assay ($EC_{50}$, nM) | Tm (melting temperature), ° C. T1 | T2 |
|---|---|---|---|---|---|---|

*Not tested.

According to the data, the humanized antibodies huE1A9C8A7-V5 and huE1A9C8A7-V8 showed higher binding affinities/activities to human (e.g., FIG. 12, Table 6-1) and cynomolgus PD-1 (e.g., FIG. 13, Table 6-1) than nivolumab and pembrolizumab. The humanized antibodies huE1A9C8A7-V5 and huE1A9C8A7-V8 also specifically bound to mouse PD1, while nivolumab and pembrolizumab did not (Table 6-1).

Figure 17:
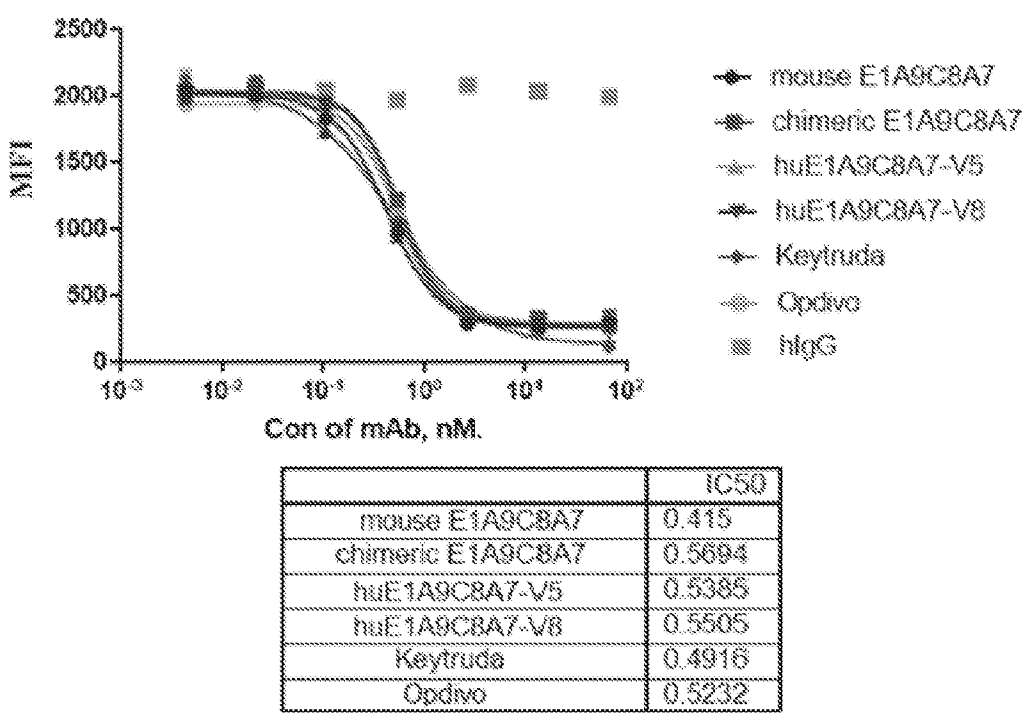
FIG. 17 shows the abilities of humanized antibodies huE1A9C8A7-V5 and huE1A9C8A7-V8 to block PD-1 binding to cell surface PD-L1 in a cell-based blocking FACS assay.
Figure 18:
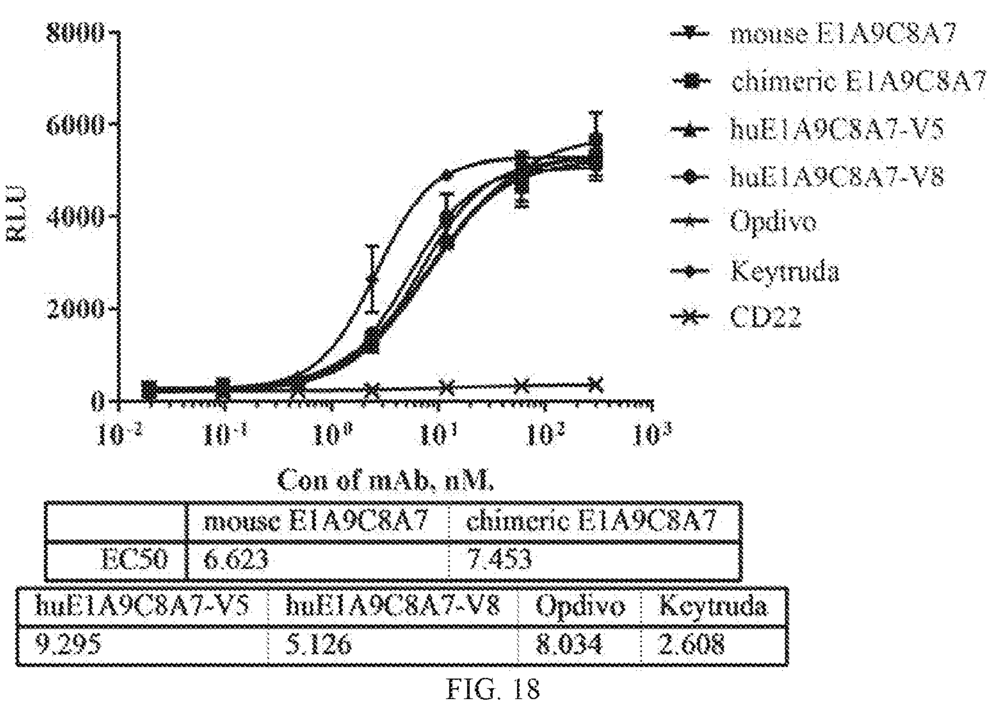
FIG. 18 shows the capabilities of humanized antibodies huE1A9C8A7-V5 and huE1A9C8A7-V8 to reverse PD-1-PD-L1 interaction induced luciferase expression decrease in a cell-based functional assay.
Figure 19A:
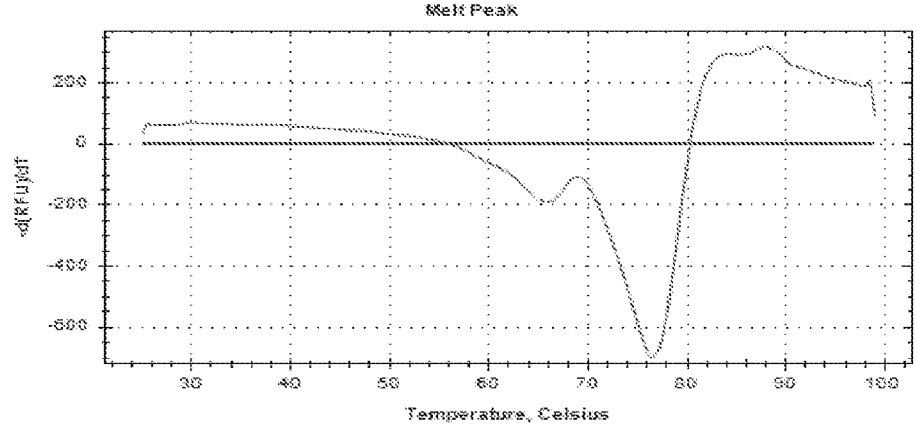
FIGS. 19A-19B show the protein thermal shift assay results of humanized antibodies huE1A9C8A7-V5 (A) and huE1A9C8A7-V8 (B).
Figure 19B:
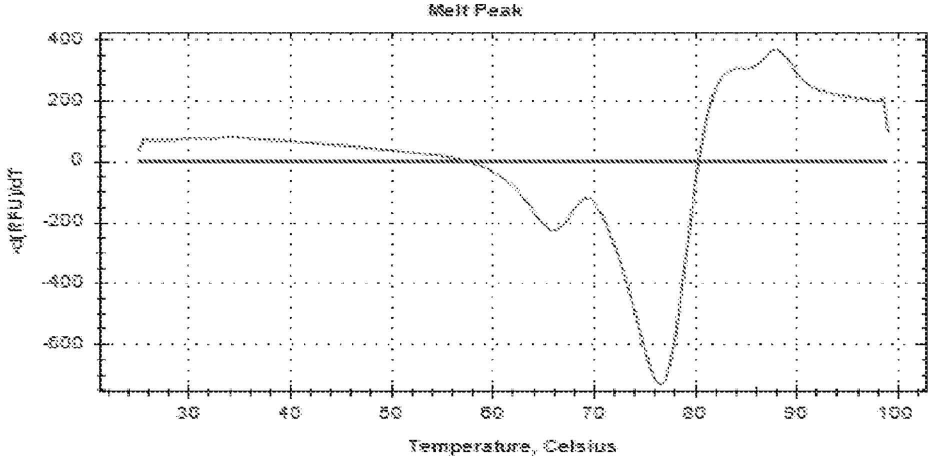

Further, the antibodies huE1A9C8A7-V5 and huE1A9C8A7-V8 showed comparable blocking capacities on PD-1-PD-L1 binding or interaction when compared to nivolumab and pembrolizumab in the competitive ELISA (FIG. 15) and cell-based blocking FACS test (FIG. 17). The antibodies huE1A9C8A7-V8 and huE1A9C8A7-V5 were able to reverse PD-1-PD-L1 interaction induced luciferase expression decrease in the cell based functional assay at comparable activities to nivolumab (FIG. 18).

Example 9. Generation and Characterization of huE1A9C8A7-V8-3 Antibody

Deamidation occurs at asparagine residues, especially those in CDRs, resulting in antibody degradation. Aspartic acid residues, especially those followed by a glycine residue, are prone to isomerization, which is another common cause for antibody degradation. To avoid amino acid deamidation and/or isomerization during production, storage, and in vivo metabolism of the antibodies of the disclosure, the CDR sequences may be optimized for better chemical stabilities.

The humanized antibody huE1A9C8A7-V8 was modified in the heavy chain variable region CDR3 and light chain variable region CDR1. The antibody with CDR modifications were designated as huE1A9C8A7-V8-3, purified as described above, and tested in Biacore™, cell-based binding FACS and cell-based functional assay, following the protocols in the foregoing Examples.

Figure 20:
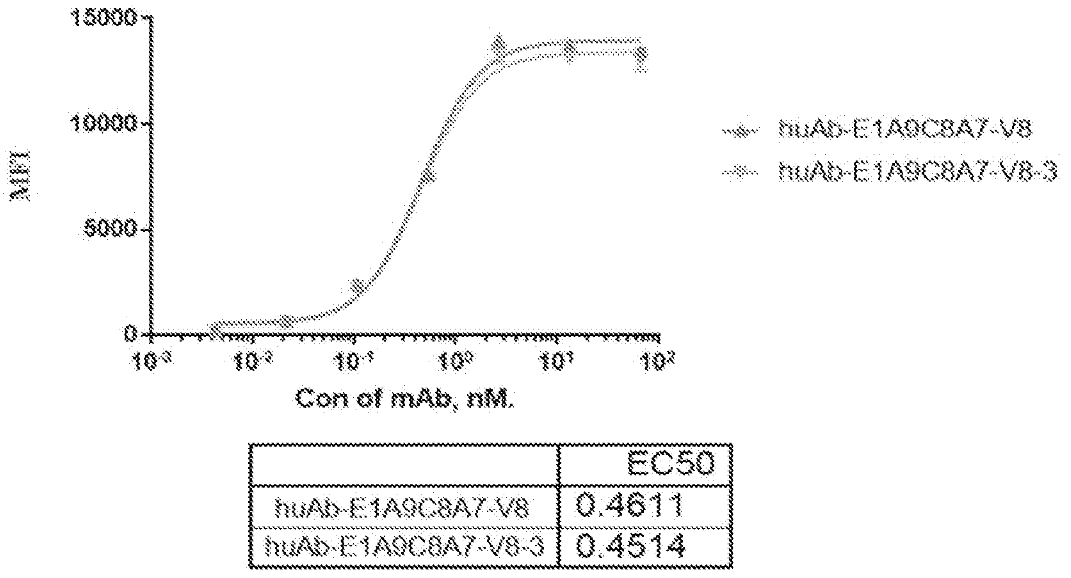
FIG. 20 shows the binding capabilities of humanized antibodies huE1A9C8A7-V8 and huE1A9C8A7-V8-3 to GS-J2/PD-1 cells expressing human PD1 in a cell-based binding FACS assay.
Figure 21:
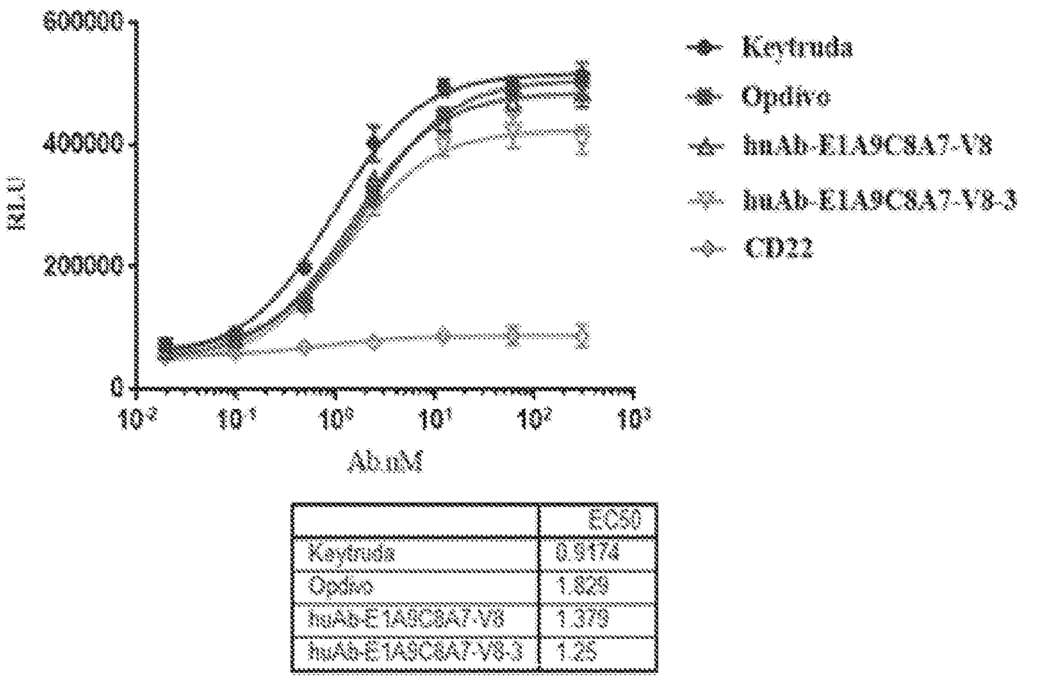
FIG. 21 shows the capabilities of humanized antibodies huE1A9C8A7-V8 and huE1A9C8A7-V8-3 to reverse PD-1-PD-L1 interaction induced luciferase expression decrease in a cell-based functional assay.

The results were shown in Tables 7-1 and 7-2, FIGS. 20 and 21.

TABLE 7-1

Binding affinity of huE1A9C8A7-V8-3 to Human and Cyno PD-1

| mAb | Kinetics on Biacore ™ Human PD-1-his $K_a$ ($M^{-1}s^{-1}$) | $K_d$ ($s^{-1}$) | $K_D$ (M) | Cynomolgus PD-1-his $K_a$ ($M^{-1}s^{-1}$) | $K_d$ ($s^{-1}$) | $K_D$ (M) |
|---|---|---|---|---|---|---|
| huE1A9C8A7-V8 | 9.34E+05 | 5.93E−04 | 6.34E−10 | 3.61E+05 | 4.84E−04 | 1.34E−09 |
| huE1A9C8A7-V8-3 | 1.07E+06 | 4.10E−04 | 3.82E−10 | 4.61E+05 | 3.32E−04 | 7.22E−10 |

TABLE 7-2

Binding affinity of huE1A9C8A7-V8-3 antibody to Mouse PD1

| mAb | Kinetics on Biacore ™ Mouse PD1-his $K_a$ ($M^{-1}s^{-1}$) | $K_d$ ($s^{-1}$) | $K_D$ (M) |
|---|---|---|---|
| huE1A9C8A7-V8 | 4.79E+04 | 1.82E−02 | 3.80E−07 |
| huE1A9C8A7-V8-3 | 6.48E+04 | 1.67E−02 | 2.44E−07 |

According to Table 7-1 and 7-2, huE1A9C8A7-V8-3 showed a bit higher binding affinities to mouse, human and cynomolgus PD-1 than huE1A9C8A7-V8. And these two antibodies showed comparable binding activities to human PD-1, as shown in FIG. 20.

Further, it can be seen from FIG. 21 that huE1A9C8A7-V8 and huE1A9C8A7-V8-3 were both able to reverse PD-1-PD-L1 interaction induced luciferase expression decrease in GS-J2/PD-1 cells more efficiently than nivolumab, but at comparable activities to pembrolizumab.

Example 10. In Vivo Anti-Tumor Efficacy of Mouse E2G4E10B7 Antibody

The in vivo anti-tumor activity of mouse E2G4E10B7 antibody was tested in C57BL/6 mice. Briefly, C57BL/6 mice were subcutaneously injected with $2\times10^6$ mouse colon cancer MC38 cells (Cat #:HYC3401, Obio Technology (Shanghai) Corp., Ltd.) at the right axilla. Tumor volumes were measured twice a week for three weeks using an electronic caliper and calculated as (length×width$^2$)/2. When tumors reached an average volume of about 30-150 mm$^3$, 24 tumor-bearing mice were selected and randomized into three groups, and the day doing the animal grouping was designated as Day 1. The animals were intravenously injected at the tail vein with vehicle (Dulbecco's phosphate-buffered saline, also referred to as DPBS), mouse E2G4E10B7 antibody, and InVivoMAb anti-mouse PD-1 (Cat #:BE0146, Bio X Cell, also referred to as CD279), respectively, at a dose of 10 mg/kg, on Day 1, 4, 8, 11, 15 and 18.

The mice in the vehicle group and the mice in the other two groups were euthanized on Day 15 and Day 22, respectively, and tumors were collected and weighed. Tumor growth rate (T/C %=($V_t$ (the tumor volume measured at Day t)/$V_0$ (the tumor volume measured at Day 1) in each treatment group)/($V_t$/$V_0$ in control group)×100%) and tumor growth inhibition rate ($IR_{TV}$%=100%−T/C %) were determined.

Figure 22:
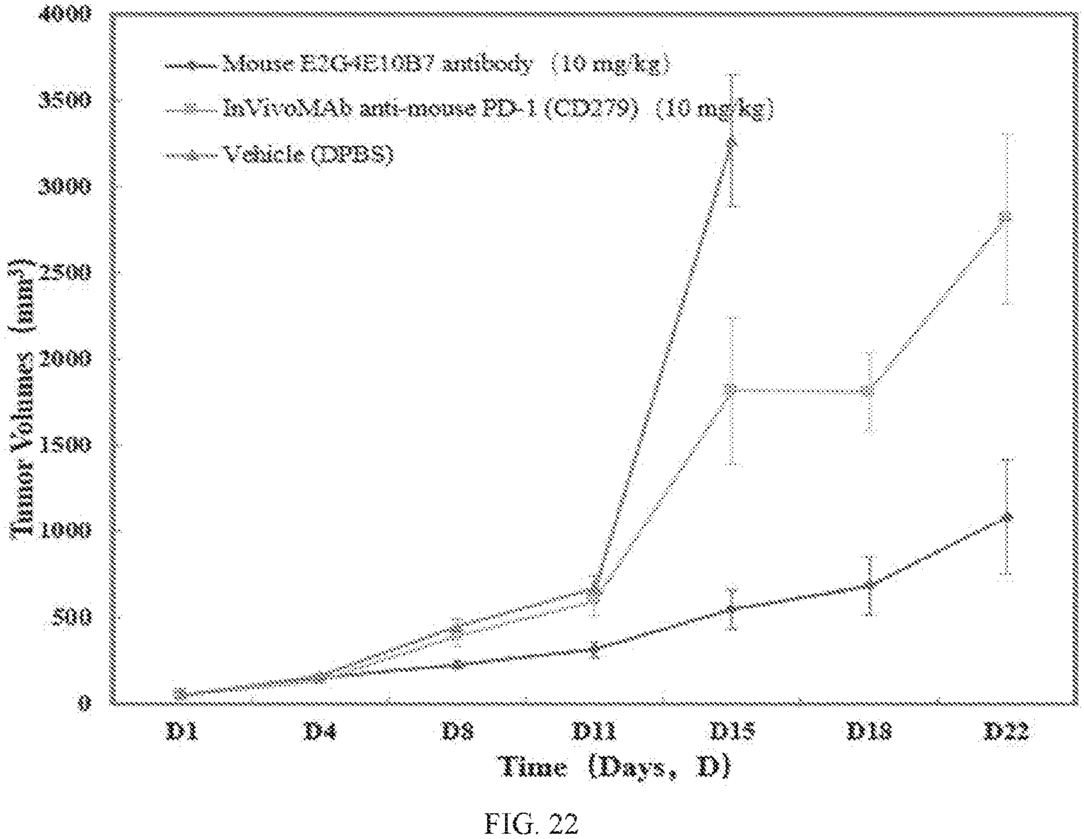
FIG. 22 depicts the tumor volume changes of mice treated with mouse antibody E2G4E10B7 or controls.

All treatments were well tolerated by the tumor-bearing animals. As can be seen from Table 8 and FIG. 22, mouse E2G4E10B7 antibody at 10 mg/kg showed significantly better efficacy than InVivoMAb anti-mouse PD-1 at 10 mg/kg.

TABLE 8

Anti-tumor Efficacy of mouse E2G4E10B7 antibody

| Group No. | Drug | Dose | Tumor Volume [a] ($mm^3$) | T/C % [b] | $IR_{TV}$ % [b] |
|---|---|---|---|---|---|
| 1 | Vehicle (DPBS) | n/a | 3268.74 ± 1077.62 | n/a | n/a |
| 2 | Mouse E2G4E10B7 | 10 mg/kg | 549.68 ± 312.68* | 18.45%* | 81.55%* |
| 3 | InVivoMAb anti-mouse PD-1 | 10 mg/kg | 1815.5 ± 1194.59* | 60.96% | 39.04% |

[a] Tumor volume at Day 15, compared with vehicle control group by student's t test,
*P ≤ 0.05 and
**P < 0.01.
[b] T/C % and $IR_{TV}$ % on Day 15, compared with In VivoMAb anti-mouse PD-1 group by student's t test,
*P ≤ 0.05 and
**P < 0.01.

While the disclosure has been described above in connection with one or more embodiments, it should be understood that the disclosure is not limited to those embodiments, and the description is intended to cover all alternatives, modifications, and equivalents, as may be included within the spirit and scope of the appended claims. All referenced cited herein are further incorporated by reference in their entirety.

Sequences in the present application are summarized below.

| Description/ Sequence/SEQ ID NO. |
|---|
| VH CDR1 of mouse, chimeric and humanized E1A9C8A7 antibodies<br>DYVMH (SEQ ID NO: 1) |
| VH CDR2 of mouse, chimeric and humanized E1A9C8A7 antibodies<br>VISTYHIPAVYNQKFKG (SEQ ID NO: 3) |
| VH CDR3 of mouse, chimeric and humanized E1A9C8A7 antibodies, except huE1A9C8A7-V8-3<br>EVYGX1SX2YFDV (SEQ ID NO: 6) X1 = D, X2 = Y<br>EVYGDSYYFDV |
| VH CDR3 of huE1A9C8A7-V8-3<br>EVYGX1SX2YFDV (SEQ ID NO: 6) X1 = E, X2 = Y<br>EVYGESYYFDV |
| VL CDR1 of mouse, chimeric and humanized E1A9C8A7 antibodies, except huE1A9C8A7-V8-3<br>RSSQSX1VHSX2GNTYLE (SEQ ID NO: 8) X1 = I, X2 = N<br>RSSQSIVHSNGNTYLE |
| VL CDR1 of huELA9C8A7-V8-3<br>RSSQSX1VHSX2GNTYLE (SEQ ID NO: 8) X1 = I, X2 = A<br>RSSQSIVHSAGNTYLE |
| VL CDR2 of mouse, chimeric and humanized E1A9C8A7 antibodies<br>KVSNRFS (SEQ ID NO: 10) |
| VL CDR3 of mouse, chimeric and humanized E1A9C8A7 antibodies<br>FQGSHVPYT (SEQ ID NO: 12) |
| VH of mouse and chimeric E1A9C8A7 antibodies<br>QVQLQQSGAEVVRPGVSVRISCKGSGYTFSDYVMHWMKQSHGESLEWIGVISTYHIPAVY<br>NQKFKGKATMTVDKSSSTVYLELARLTSEDSAIYYCAREVYGDSYYFDVWGAGTTVTVS<br>S (SEQ ID NO: 14) |

-continued

| Description/ Sequence/SEQ ID NO. |
|---|
| VH of mouse E1A9C8A7 CAGGTCCAGCTGCAGCAGTCTGGGGCTGAGGTGGTGAGGCCTGGGGTCTCAGTGAGGA TTTCCTGCAAGGGTTCTGGCTACACATTCTCTGATTATGTTATGCACTGGATGAAGCAG AGTCATGGAGAGAGCCTAGAGTGGATTGGGGTTATCAGTACTTACCATATTCCTGCTG TCTACAACCAGAAGTTCAAGGGCAAGGCCACAATGACTGTAGACAAATCCTCCAGTAC AGTCTATCTGGAACTTGCCAGACTGACATCTGAGGATTCTGCCATCTATTACTGTGCAA GAGAGGTCTATGGTGACTCTTACTACTTCGATGTCTGGGGCGCGGGGACCACGGTCAC CGTCTCCTCA (SEQ ID NO: 30) |
| VH of chimeric E1A9C8A7 CAAGTGCAGCTGCAGCAGAGCGGCGCCGAAGTGGTGAGACCCGGCGTGAGCGTGAGG ATCAGCTGCAAGGGCAGCGGCTATACCTTCAGCGACTACGTGATGCACTGGATGAAGC AGAGCCACGGCGAGTCTCTGGAGTGGATCGGAGTGATCAGCACCTACCACATCCCCGC CGTGTACAACCAGAAGTTCAAGGGCAAGGCCACCATGACCGTGGACAAGAGCAGCAG CACCGTGTATCTGGAGCTGGCTAGACTGACCTCCGAGGATAGCGCCATCTACTACTGC GCCAGAGAGGTGTACGGCGATAGCTACTACTTCGACGTGTGGGGCGCCGGAACCACA GTGACCGTGAGCAGCG (SEQ ID NO: 31) |
| VH of huE1A9C8A7-V1 QVQLVQSGAEVVKPGASVKISCKASGYTFX1DYVMHWX2RQAPGQSLEWIGVISTYHIPA VYNQKFKGKATMTVDX3STSTVYLELSSLRSEDTAVYYCAREVYGDSYYFDVWGQGTTV TVSS (SEQ ID NO: 15) X1 = S, X2 = M, X3 = K QVQLVQSGAEVVKPGASVKISCKASGYTFSDYVMHWVRQAPGQSLEWIGVISTYHIPAVY NQKFKGKATMTVDKSTSTVYLELSSLRSEDTAVYYCAREVYGDSYYFDVWGQGTTVTVS S |
| VH of huE1A9C8A7-V2 QVQLVQSGAEVVKPGASVKISCKASGYTFX1DYVMHWX2RQAPGQSLEWIGVISTYHIPA VYNQKFKGKATMTVDX3STSTVYLELSSLRSEDTAVYYCAREVYGDSYYFDVWGQGTTV TVSS (SEQ ID NO: 15) X1 = T, X2 = M, X3 = K QVQLVQSGAEVVKPGASVKISCKASGYTFTDYVMHWMRQAPGQSLEWIGVISTYHIPAV YNQKFKGKATMTVDKSTSTVYLELSSLRSEDTAVYYCAREVYGDSYYFDVWGQGTTVTV SS |
| VH of huE1A9C8A7-V3 QVQLVQSGAEVVKPGASVKISCKASGYTFX1DYVMHWX2RQAPGQSLEWIGISTYHIPA VYNQKFKGKATMTVDX3STSTVYLELSSLRSEDTAVYYCAREVYGDSYYFDVWGQGTTV TVSS (SEQ ID NO: 15) X1 = S, X2 = V, X3 = K QVQLVQSGAEVVKPGASVKISCKASGYTFSDYVMHWVRQAPGQSLEWIGVISTYHIPAVY NQKFKGKATMTVDKSTSTVYLELSSLRSEDTAVYYCAREVYGDSYYFDVWGQGTTVTVS S |
| VH of huE1A9C8A7-V4 QVQLVQSGAEVVKPGASVKISCKASGYTFX1DYVMHWX2RQAPGQSLEWIGVISTYHIPA VYNQKFKGKATMTVDX3STSTVYLELSSLRSEDTAVYYCAREVYGDSYYFDVWGQGTTV TVSS (SEQ ID NO: 15) X1 = S, X2 = M, X3 = T QVQLVQSGAEVVKPGASVKISCKASGYTFSDYVMHWMRQAPGQSLEWIGVISTYHIPAVY NQKFKGKATMTVDTSTSTVYLELSSLRSEDTAVYYCAREVYGDSYYFDVWGQGTTVTVS S |
| VH of huE1A9C8A7-V5 QVQLVQSGAEVVKPGASVKISCKASGYTFX1DYVMHWX2RQAPGQSLEWIGVISTYHIPA VYNQKFKGKATMTVDX3STSTVYLELSSLRSEDTAVYYCAREVYGDSYYFDVWGQGTTV TVSS (SEQ ID NO: 15) X1 = T, X2 = V, X3 = T QVQLVQSGAEVVKPGASVKISCKASGYTFTDYVMHWVRQAPGQSLEWIGVISTYHIPAVY NQKFKGKATMTVDTSTSTVYLELSSLRSEDTAVYYCAREVYGDSYYFDVWGQGTTVTVS S |
| VH of huE1A9C8A7-V6 QVQLVQSGAEVVKPGASVKX1SCKASGYTFTDYVMHWVRQAPGQX2LEWX3GVISTYHI PAVYNQKFKGKATMTVDTSTSTVYLELSSLRSEDTAVYYCAREVYGDSYYFDVWGQGTT VTVSS (SEQ ID NO: 16) X1 = V, X2 = S, X3 = 1 QVQLVQSGAEVVKPGASVKVSCKASGYTFTDYVMHWVRQAPGQSLEWIGVISTYHIPAV YNQKFKGKATMTVDTSTSTVYLELSSLRSEDTAVYYCAREVYGDSYYFDVWGQGTTVTV SS |
| VH of huE1A9C8A7-V7 QVQLVQSGAEVVKPGASVKX1SCKASGYTFTDYVMHWVRQAPGQX2LEWX3GVISTYHI PAVYNQKFKGKATMTVDISTSTVYLELSSLRSEDTAVYYCAREVYGDSYYFDVWGQGTT VTVSS (SEQ ID NO: 16) X1 = 1, X2 = G, X3 = I QVQLVQSGAEVVKPGASVKISCKASGYTFTDYVMHWVRQAPGQGLEWIGVISTYHIPAVY NQKFKGKATMTVDTSTSTVYLELSSLRSEDTAVYYCAREVYGDSYYFDVWGQGTTVTVS S |
| VH of huE1A9C8A7-V8 QVQLVQSGAEVVKPGASVKX1SCKASGYTFTDYVMHWVRQAPGQX2LEWX3GVISTYHI PAVYNQKFKGKATMTVDISTSTVYLELSSLRSEDTAVYYCAREVYGDSYYFDVWGQGTT |

-continued

| Description/ Sequence/SEQ ID NO. |
|---|
| VTVSS (SEQ ID NO: 16) X1 = 1, X2-S, X3 = M<br>QVQLVQSGAEVVKPGASVKISCKASGYTFTDYVMHWVRQAPGQSLEWMGVISTYHIPAV<br>YNQKFKGKATMTVDISTSTVYLELSSLRSEDTAVYYCAREVYGDSYYFDVWGQGTTVTV<br>SS<br>CAAGTGCAGCTGGTGCAGAGCGGAGCCGAAGTGGTGAAACCCGGCGCCAGCGTGAAG<br>ATCAGCTGCAAGGCCAGCGGCTACACCTTCACCGACTACGTGATGCACTGGGTGAGAC<br>AAGCCCCCGGCCAGTCTCTGGAGTGGATGGGCGTGATCAGCACCTACCACATCCCCGC<br>CGTGTACAACCAGAAGTTCAAGGGCAAGGCCACCATGACCGTGGACACCAGCACCAG<br>CACCGTGTATCTGGAGCTGTCCTCTCTGAGGAGCGAGGACACCGCCGTGTACTACTGC<br>GCCAGAGAGGTGTACGGCGACAGCTACTACTTCGACGTGTGGGGCCAAGGCACCACA<br>GTGACCGTGAGCAGC (SEQ ID NO: 32) |
| VH of huE1A9C8A7-V9<br>QVQLVQSGAEVVKPGASVKISCKASGYTFTDYVMHWVRQAPGQSLEWIGVISTYHIPAVY<br>NQKFKGX1X2TMTX3DISTSTVYLELSSLRSEDTAVYYCAREVYGDSYYFDVWGQGTTVT<br>VSS (SEQ ID NO: 17) X1 = R, X2 = A, X3 = V<br>QVQLVQSGAEVVKPGASVKISCKASGYTFTDYVMHWVRQAPGQSLEWIGVISTYHIPAVY<br>NQKFKGRATMTVDISTSTVYLELSSLRSEDTAVYYCAREVYGDSYYFDVWGQGTTVTVS<br>S |
| VH of huE1A9C8A7-V10<br>QVQLVQSGAEVVKPGASVKISCKASGYTFTDYVMHWVRQAPGQSLEWIGVISTYHIPAVY<br>NQKFKGX1X2TMTX3DTSTSTVYLELSSLRSEDTAVYYCAREVYGDSYYFDVWGQGTTVT<br>VSS (SEQ ID NO: 17) X1 = K, X2 = V, X3 = V<br>QVQLVQSGAEVVKPGASVKISCKASGYTFTDYVMHWVRQAPGQSLEWIGVISTYHIPAVY<br>NQKFKGKVTMTVDTSTSTVYLELSSLRSEDTAVYYCAREVYGDSYYFDVWGQGTTVTVS<br>S |
| VH of huE1A9C8A7-V11<br>QVQLVQSGAEVVKPGASVKISCKASGYTFTDYVMHWVRQAPGQSLEWIGVISTYHIPAVY<br>NQKFKGX1X2TMTX3DTSTSTVYLELSSLRSEDTAVYYCAREVYGDSYYFDVWGQGTTVT<br>VSS (SEQ ID NO: 17) X1 = K, X2 = A, X3 = R<br>QVQLVQSGAEVVKPGASVKISCKASGYTFTDYVMHWVRQAPGQSLEWIGVISTYHIPAVY<br>NQKFKGKATMTRDISTSTVYLELSSLRSEDTAVYYCAREVYGDSYYFDVWGQGTTVTVS<br>S |
| VH of huE1A9C8A7-V8-3<br>QVQLVQSGAEVVKPGASVKISCKASGYTFTDYVMHWVRQAPGQSLEWMGVISTYHIPAV<br>YNQKFKGKATMTVDISTSTVYLELSSLRSEDTAVYYCAREVYGESYYFDVWGQGTTVTV<br>SS (SEQ ID NO: 42) |
| VL for mouse and chimeric E1A9C8A7<br>DVLMTQIPLSLPVSLGDQVSISCRSSQSIVHSNGNTYLEWYLQKPGQSPKLLIYKVSNRFSG<br>VPDRFSGSGSGTDFTLKISRVEAEDLGVYYCFQGSHVPYTFGGGTKLEIK (SEQ ID NO: 20)<br>VL of mouse E1A9C8A7<br>GATGTTTTGATGACCCAAATTCCACTCTCCCTGCCTGTTAGTCTTGGAGATCAAGTCTC<br>CATCTCTTGCAGATCTAGTCAGAGCATTGTACATAGTAATGGAAACACCTATTTAGAAT<br>GGTACCTGCAGAAACCAGGCCAGTCTCCAAAGCTCCTGATCTACAAAGTTTCCAACCG<br>ATTTTCTGGGGTCCCAGACAGGTTCAGTGGCAGTGGATCAGGGACAGATTTCACACTC<br>AAGATCAGCAGAGTGGAGGCTGAGGATCTGGGAGTTTATTACTGCTTTCAAGGTTCAC<br>ATGTTCCGTACACGTTCGGAGGGGGGACCAAGCTGGAAATAAAA (SEQ ID NO: 33)<br>VL of chimeric E1A9C8A7<br>GACGTGCTGATGACCCAGATCCCTCTGTCTCTGCCCGTGTCTCTGGGAGATCAAGTGAG<br>CATCAGCTGCAGATCCAGCCAGAGCATCGTGCACAGCAACGGCAACACCTATCTGGAG<br>TGGTATCTGCAGAAGCCCGGCCAGAGCCCCAAGCTGCTGATCTACAAGGTCTCCAATA<br>GATTCTCCGGCGTGCCCGATAGATTCAGCGGAAGCGGCAGCGGCACCGACTTCACACT<br>GAAGATCTCCAGAGTGGAGGCCGAGGATCTGGGCGTGTACTACTGCTTTCAAGGCAGC<br>CACGTGCCCTACACCTTTGGCGGCGGCACCAAACTGGAGATCAAG (SEQ ID NO: 34) |
| VL of huE1A9C8A7-V1-huE1A9C8A7-V11<br>DIVMTQTPLSLPVTPGEPASISCRSSQSIVHSX1GNTYLEWYLQKPGQSPQLLIYKVSNRFSG<br>VPDRFSGSGSGTDFTLKISRVEAEDVGVYYCFQGSHVPYTFGGGTKVEIK (SEQ ID NO: 21)<br>X1 = N<br>DIVMTQTPLSLPVTPGEPASISCRSSQSIVHSNGNTYLEWYLQKPGQSPQLLIYKVSNRFSG<br>VPDRFSGSGSGTDFTLKISRVEAEDVGVYYCFQGSHVPYTFGGGTKVEIK<br>GACATCGTGATGACCCAGACACCTCTGTCTCTGCCCGTGACACCCGGCGAGCCCGCCA<br>GCATCAGCTGCAGAAGCAGCCAGAGCATCGTGCACAGCAACGGCAACACCTATCTGG<br>AGTGGTATCTGCAGAAGCCCGGCCAGAGCCCTCAGCTGCTGATCTACAAGGTGTCCAA<br>TAGATTCAGCGGCGTGCCCGACAGATTCAGCGGCAGCGGAAGCGGCACAGACTTCAC<br>ACTGAAGATCTCCAGAGTGGAGGCCGAGGACGTGGGCGTGTACTACTGCTTCCAAGGC<br>AGCCACGTGCCTTACACCTTCGGCGGCGGCACCAAGGTGGAGATCAAG (SEQ ID NO:<br>35) |
| VL of huE1A9C8A7-V8-3<br>DIVMTQTPLSLPVTPGEPASISCRSSQSIVHSX1GNTYLEWYLQKPGQSPQLLIYKVSNRFSG<br>VPDRFSGSGSGTDFTLKISRVEAEDVGVYYCFQGSHVPYTFGGGTKVEIK (SEQ ID NO: 21) |

-continued

| Description/ Sequence/SEQ ID NO. |
|---|
| X1 = A<br>DIVMTQTPLSLPVTPGEPASISCRSSQSIVHSAGNTYLEWYLQKPGQSPQLLIYKVSNRFSG<br>VPDRFSGSGSGTDFTLKISRVEAEDVGVYYCFQGSHVPYTFGGGTKVEIK<br>RSSQSIVHSAGNTYLE |
| VH CDR1 of mouse E2G4E10B7<br>DYVMH (SEQ ID NO: 1) |
| VH CDR2 of mouse E2G4E10B7<br>VISTHFGDGVYNQKFKG (SEQ ID NO: 4) |
| VH CDR3 of mouse E2G4E10B7<br>EVYGX1SX2YFDV (SEQ ID NO: 6) X1 = D, X2 = W<br>EVYGDSWYFDV |
| VL CDR1 of mouse E2G4E10B7<br>RSSQSX1VHSX2GNTYLE (SEQ ID NO: 8) X1 = L, X2 = D<br>RSSQSLVHSDGNTYLE |
| VL CDR2 of mouse E2G4E10B7<br>KVSNRFS (SEQ ID NO: 10) |
| VL CDR3 of mouse E2G4E10B7<br>FQGSHVPYT (SEQ ID NO: 12) |
| VH of mouse E2G4E10B7<br>QVQLQQSGAELVRPGVSVKISCKGSGYTFTDYVMHWVRQSHAKSLEWIGVISTHFGDGV<br>YNQKFKGKATMTVDKSSSTAYMELARLISEDSAIYYCAREVYGDSWYFDVWGAGTTVT<br>VSS (SEQ ID NO: 18)<br>CAGGTCCAGCTGCAGCAGTCTGGGGCTGAGCTGGTGAGGCCTGGGGTCTCAGTGAAGA<br>TTTCCTGCAAGGGTTCTGGCTACACATTCACTGATTATGTTATGCACTGGGTGAGGCAG<br>AGCCATGCAAAGAGTCTAGAGTGGATTGGAGTTATCAGTACTCACTTTGGTGATGGTG<br>TTTACAACCAGAAGTTCAAGGGCAAGGCCACAATGACTGTAGACAAATCCTCCAGCAC<br>AGCCTATATGGAACTTGCCAGACTGACATCTGAGGATTCTGCCATCTATTACTGTGCAA<br>GAGAGGTCTATGGTGACTCTTGGTACTTCGATGTCTGGGGCGCAGGGACCACGGTCAC<br>CGTCTCCTCA (SEQ ID NO: 36) |
| VL of mouse E2G4E10B7<br>DVLMTQTPLSLPVSLGDQASISCRSSQSLVHSDGNTYLEWYLQKPGQSPKLLIYKVSNRFS<br>GVPDRFSGSGSGTDFTLKISRLEAEDLGVYYCFQGSHVPYTFGGGTKLEIK (SEQ ID NO:<br>22)<br>GATGTTTTGATGACCCAAACTCCACTCTCCCTGCCTGTCAGTCTTGGAGATCAAGCCTC<br>CATCTCTTGCAGATCTAGTCAGAGCCTTGTACATAGTGATGGAAACACCTATTTAGAAT<br>GGTACCTGCAGAAACCAGGCCAGTCTCCAAAGCTCCTGATCTACAAAGTTTCCAACCG<br>ATTTTCTGGGGTCCCAGACAGGTTCAGTGGCAGTGGATCAGGGACAGATTTCACACTC<br>AAGATCAGCAGACTGGAGGCTGAGGATCTGGGAGTTTATTACTGCTTTCAAGGTTCAC<br>ATGTTCCGTACACGTTCGGAGGGGGGACCAAGCTGGAAATAAAA (SEQ ID NO: 37) |
| VH CDR1 of mouse E1G5D1H1<br>DFYMY (SEQ ID NO: 2) |
| VH CDR2 of mouse E1G5D1H1<br>TISNSGTQTYYLDSVKG (SEQ ID NO: 5) |
| VH CDR3 of mouse E1G5D1H1<br>DYYRYDSWYFDV (SEQ ID NO: 7) |
| VL CDR1 of mouse E1G5D1H1<br>RASESVDFYGTSLMQ (SEQ ID NO: 9) |
| VL CDR2 of mouse E1G5D1H1<br>AASNVES (SEQ ID NO: 11) |
| VL CDR3 of mouse E1G5D1H1<br>QQSRKVPWT (SEQ ID NO: 13) |
| VH of mouse E1G5D1H1<br>EVQLVESGGGLVKPGGLKLSCAASGFTFSDFYMYWVRQTPEKRLEWVATISNSGTQTYY<br>LDSVKGRFTISRDNAKNNLYLQMSSLKSEDTAMYYCARDYYRYDSWYFDVWGAGTTVT<br>VSS (SEQ ID NO: 19)<br>GAAGTGCAGTTGGTGGAGTCTGGGGGAGGCTTAGTGAAGCCTGGAGGGTCTCTGAAGC<br>TCTCCTGTGCAGCCTCTGGATTCACTTTCAGTGACTTTTACATGTATTGGGTTCGCCAG<br>ACTCCGGAAAAGAGGCTGGAGTGGGTCGCAACCATTAGTAATAGTGGTACTCAAACCT<br>ACTATCTAGACAGTGTGAAGGGGCGATTCACCATCTCCAGAGACAATGCCAAGAATAA |

-continued

| Description/ Sequence/SEQ ID NO. |
|---|
| CCTGTACCTGCAAATGAGCAGTCTGAAGTCTGAGGACACAGCCATGTACTATTGTGCT AGAGACTACTATAGGTACGACAGCTGGTACTTCGATGTCTGGGGCGCAGGGACCACGG TCACCGTCTCCTCA (SEQ ID NO: 38) |
| VL of mouse E1G5D1H1 DIVLTQSPASLAVSQGQRATISCRASESVDFYGTSLMQWFQLKPGQPPKLLIYAASNVESG VPARFSGSGSGTNFSLNIHPVEEDDIAMYFCQQSRKVPWTFGGGTNLEIK (SEQ ID NO: 23) GACATTGTATTAACCCAATCTCCAGCTTCTTTGGCTGTGTCTCAAGGGCAGAGAGCCAC CATCTCCTGCAGAGCCAGTGAAAGTGTTGATTTTTATGGCACAAGTTTAATGCAGTGGT TCCAACTGAAACCAGGACAGCCACCCAAACTCCTCATCTATGCTGCATCCAACGTCGA ATCTGGAGTCCCTGCCAGGTTTAGTGGCAGTGGGTCTGGGACAAACTTCAGCCTCAAC ATCCATCCTGTGGAGGAGGATGATATTGCCATGTATTTCTGTCAGCAAAGTAGGAAGG TTCCGTGGACATTCGGTGGAGGCACCAACCTTGAAATCAAA (SEQ ID NO: 39) |
| Heavy chain constant region for chimeric and humanized antibodies ASTKGPSVFPLAPCSRSTSESTAALGCLVKDYFPEPVTVSWNSGALTSGVHTFPAVLQSSGL YSLSSVVTVPSSSLGTKTYTCNVDHKPSNTKVDKRVESKYGPPCPpCPAPEFLGGPSVFLFP PKPKDTLMISRTPEVTCVVVDVSQEDPEVQFNWYVDGVEVHNAKTKPREEQFNSTYRVVS VLTVLHQDWLNGKEYKCKVSNKGLPSSIEKTISKAKGQPREPQVYTLPPSQEEMTKNQVS LTCLVKGFYPSDIAVEWESNGQPENNYKTTPPVLDSDGSFFLYSRLTVDKSRWQEGNVFSC SVMHEALHNHYTQKSLSLSLGK (SEQ ID NO: 24) GCCAGCACAAAGGGCCCTTCCGTGTTTCCCCTGGCCCCCTGCAGCAGGAGCACCTCTG AGTCCACCGCCGCCCTGGGCTGTCTGGTGAAGGACTACTTTCCCGAGCCCGTGACCGT GAGCTGGAATTCCGGCGCCCTGACATCCGGCGTGCACACCTTCCCCGCCGTGCTGCAG TCCTCCGGCCTGTACAGCCTGAGCTCCGTGGTGACAGTGCCTTCCTCCTCCCTGGGCAC CAAGACCTACACATGTAATGTGGATCACAAGCCCAGCAACACAAAGGTGGATAAGAG AGTGGAGTCCAAGTACGGCCCTCCTTGCCCTCCCTGTCCTGCCCCAGAGTTCCTGGGCG GCCCCTCTGTGTTCCTGTTCCCCCCTAAGCCCAAGGACACACTGATGATCTCCAGGACC CCTGAGGTGACCTGCGTGGTGGTGGACGTGAGCCAGGAGGACCCTGAGGTGCAGTTCA ATTGGTACGTGGATGGCGTGGAGGTGCACAATGCCAAGACAAAGCCCAGAGAGGAGC AGTTTAATTCCACATACAGGGTGGTGTCCGTGCTGACCGTGCTGCACCAGGATTGGCT GAACGGCAAGGAGTACAAGTGTAAGGTGAGCAACAAGGGCCTGCCTTCCTCCATCGA GAAGACAATCAGCAAGGCCAAGGGCCAGCCTAGGGAGCCCCAGGTGTACACACTGCC TCCCAGCCAGGAGGAGATGACCAAGAACCAGGTGAGCCTGACCTGCCTGGTGAAGGG CTTCTACCCTAGCGACATCGCCGTGGAGTGGGAGTCCAACGGCCAGCCCGAGAATAAC TACAAGACAACACCCCCCGTGCTGGATTCCGATGGCAGCTTCTTTCTGTACTCCAGGCT GACCGTGGATAAGAGCAGGTGGCAGGAGGGCAATGTGTTCAGCTGCTCCGTGATGCAC GAGGCCCTGCACAATCACTACACCCAGAAGAGCCTGTCCCTGAGCCTGGGCAAGTGA (SEQ ID NO: 40) |
| Light chain constant region for chimeric and humanized antibodies RTVAAPSVFIFPPSDEQLKSGTASVVCLLNNFYPREAKVQWKVDNALQSGNSQESVTEQD SKDSTYSLSSTLTLSKADYEKHKVYACEVTHQGLSSPVTKSFNRGEC (SEQ ID NO: 25) CGTACGGTGGCTGCACCATCTGTCTTCATCTTCCCGCCATCTGATGAGCAGTTGAAATC TGGAACTGCCTCTGTTGTGTGCCTGCTGAATAACTTCTATCCCAGAGAGGCCAAAGTAC AGTGGAAGGTGGATAACGCCCTCCAATCGGGTAACTCCCAGGAGAGTGTCACAGAGC AGGACAGCAAGGACAGCACCTACAGCCTCAGCAGCACCCTGACGCTGAGCAAAGCAG ACTACGAGAAACACAAAGTCTACGCCTGCGAAGTCACCCATCAGGGCCTGAGCTCGCC CGTCACAAAGAGCTTCAACAGGGGAGAGIGTTAG (SEQ ID NO: 41) |
| Human PD1-Fc protein LDSPDRPWNPPTFSPALLVVTEGDNATFTCSFSNTSESFVLNWYRMSPSNQTDKLAAFPED RSQPGQDCRFRVTQLPNGRDFHMSVVRARRNDSGTYLCGAISLAPKAQIKESLRAELRVTE RRAEVPTAHPSPSPRPAGQFQENLYFQGEPKSCDKTHTCPPCPAPELLGGPSVFLFPPKPKD TLMISRTPEVTCVVVDVSHEDPEVKFNWYVDGVEVHNAKTKPREEQYNSTYRVVSVLIV LHQDWLNGKEYKCKVSNKALPAPIEKTISKAKGQPREPQVYTLPPSREEMTKNQVSLTCL VKGFYPSDIAVEWESNGQPENNYKTTPPVLDSDGSFFLYSKLTVDKSRWQQGNVFSCSVM HEALHNHYTQKSLSLSPGK (SEQ ID NO: 26) |
| Mouse PD-1-his MWVRQVPWSFTWAVLQLSWQSGWLLEVPNGPWRSLTFYPAWLTVSEGANATFTCSLSN WSEDLMLNWNRLSPSNQTEKQAAFCNGLSQPVQDARFQIIQLPNRHDFHMNILDTRRNDS GIYLCGAISLHPKAKIEESPGAELVVTERILETSTRYPSPSPKPEGRFQGMVIGIMSALVGIPV LLLLAWALAVFCSTSMSEARGAGSKDDTLKEEPSAAPVPSVAYEELDFQGREKTPELPTAC VHTEYATIVFTEGLGASAMGRRGSADGLQGPRPPRHEDGHCSWPLHHHHHH (SEQ ID NO: 27) |
| Human PDL1-Fc protein FTVTVPKDLYVVEYGSNMTIECKFPVEKQLDLAALIVYWEMEDKNIIQFVHGEEDLKVQH SSYRQRARLLKDQLSLGNAALQITDVKLQDAGVYRCMISYGGADYKRITVKVNAPYNKIN QRILVVDPVTSEHELTCQAEGYPKAEVIWTSSDHQVLSGKTTTTNSKREEKLFNVTSTLRIN TTTNEIFYCTFRRLDPEENHTAELVIPELPLAHPPNERTEPKSCDKTHTCPPCPAPELLGGPS VFLFPPKPKDTLMISRTPEVTCVVVDVSHEDPEVKFNWYVDGVEVHNAKTKPREEQYNST YRVVSVLTVLHQDWLNGKEYKCKVSNKALPAPIEKTISKAKGQPREPQVYTLPPSREEMT KNQVSLTCLVKGFYPSDIAVEWESNGQPENNYKTTPPVLDSDGSFFLYSKLTVDKSRWQQ GNVFSCSVMHEALHNHYTQKSLSLSPGK (SEQ ID NO: 28) |

-continued

| Description/ Sequence/SEQ ID NO. |
|---|
| Human PD1-his LDSPDRPWNPPTFSPALLVVTEGDNATFTCSFSNTSESFVLNWYRMSPSNQTDKLAAFPED RSQPGQDCRFRVTQLPNGRDFHMSVVRARRNDSGTYLCGAISLAPKAQIKESLRAELRVTE RRAEVPTAHPSPSPRPAGQFQHHHHHHHH (SEQ ID NO: 29) |

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

The invention claimed is:

1. An isolated monoclonal antibody, or an antigen-binding portion thereof, capable of binding to PD-1, comprising (i) a heavy chain variable region comprising a VH CDR1 region, a VH CDR2 region and a VH CDR3 region; and (ii) a light chain variable region comprising a VL CDR1 region, a VL CDR2 region and a VL CDR3 region, wherein the VH CDR1 region, the VH CDR2 region, the VH CDR3 region, the VL CDR1 region, the VL CDR2 region and the VL CDR3 region comprise the amino acid sequences of (1) SEQ ID NOs: 1, 3, 6, 8, 10 and 12, respectively, wherein the $5^{th}$ and $7^{th}$ amino acid residues in SEQ ID NO: 6 are D and Y respectively, wherein the $6^{th}$ and $10^{th}$ amino acid residues in SEQ ID NO: 8 are I and N respectively;

(2) SEQ ID NOs: 1, 3, 6, 8, 10 and 12, respectively, wherein the $5^{th}$ and $7^{th}$ amino acid residues in SEQ ID NO: 6 are E and Y respectively, wherein the $6^{th}$ and $10^{th}$ amino acid residues in SEQ ID NO: 8 are I and A respectively;

(3) SEQ ID NOs: 1, 4, 6, 8, 10 and 12, respectively, wherein the $5^{th}$ and $7^{th}$ amino acid residues in SEQ ID NO: 6 are D and W respectively, wherein the $6^{th}$ and $10^{th}$ amino acid residues in SEQ ID NO: 8 are L and D respectively; or (4) SEQ ID NOs: 2, 5, 7, 9, 11 and 13, respectively.

2. The isolated monoclonal antibody, or the antigen-binding portion thereof, of claim 1, wherein the heavy chain variable region comprises an amino acid sequence having at least 85%, 86%, 87%, 88%, 89%, 90%, 91%, 92%, 93%, 94%, 95%, 96%, 97%, 98%, 99% or 100% identity to SEQ ID NOs: 14, 15, 16, 17, 18, 19 or 42, wherein the $30^{th}$, $37^{th}$ and $74^{th}$ amino acid residues in SEQ ID NO: 15 are S, M and K respectively; T, M and K respectively; S, V and K respectively; S, M and T respectively; or T, V and T respectively;

wherein the $20^{th}$, $44^{th}$ and $48^{th}$ amino acid residues in SEQ ID NO: 16 are V, S and I respectively; I, G and I respectively; or I, S and M respectively;

wherein the $67^{th}$, $68^{th}$ and $72^{nd}$ amino acid residues in SEQ ID NO: 17 are R, A and V respectively; K, V and V respectively; or K, A and R respectively.

3. The isolated monoclonal antibody, or the antigen-binding portion thereof, of claim 1, wherein the light chain variable region comprises an amino acid sequence having at least 85%, 86%, 87%, 88%, 89%, 90%, 91%, 92%, 93%, 94%, 95%, 96%, 97%, 98%, 99% or 100% identity to SEQ ID NOs: 20, 21, 22 or 23, wherein the $33^{rd}$ amino acid residue in SEQ ID NO: 21 is N or A.

4. The isolated monoclonal antibody, or the antigen-binding portion thereof, of claim 2, wherein the heavy chain variable region and the light chain variable region comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 14 and 20, respectively;
(2) SEQ ID NOs: 15 and 21, respectively, wherein the $30^{th}$, $37^{th}$ and $74^{th}$ amino acid residues in SEQ ID NO: 15 are S, M and K respectively, wherein the $33^{rd}$ amino acid residue in SEQ ID NO: 21 is N;
(3) SEQ ID NOs: 15 and 21, respectively, wherein the $30^{th}$, $37^{th}$ and $74^{th}$ amino acid residues in SEQ ID NO: 15 are T, M and K respectively, wherein the $33^{rd}$ amino acid residue in SEQ ID NO: 21 is N;
(4) SEQ ID NOs: 15 and 21, respectively, wherein the $30^{th}$, $37^{th}$ and $74^{th}$ amino acid residues in SEQ ID NO: 15 are S, V and K respectively, wherein the $33^{rd}$ amino acid residue in SEQ ID NO: 21 is N;
(5) SEQ ID NOs: 15 and 21, respectively, wherein the $30^{th}$, $37^{th}$ and $74^{th}$ amino acid residues in SEQ ID NO: 15 are S, M and T respectively, wherein the $33^{rd}$ amino acid residue in SEQ ID NO: 21 is N;
(6) SEQ ID NOs: 15 and 21, respectively, wherein the $30^{th}$, $37^{th}$ and $74^{th}$ amino acid residues in SEQ ID NO: 15 are T, V and T respectively, wherein the $33^{rd}$ amino acid residue in SEQ ID NO: 21 is N;
(7) SEQ ID NOs: 16 and 21, respectively, wherein the $20^{th}$, $44^{th}$ and $48^{th}$ amino acid residues in SEQ ID NO: 16 are V, S and I respectively, wherein the $33^{rd}$ amino acid residue in SEQ ID NO: 21 is N;
(8) SEQ ID NOs: 16 and 21, respectively, wherein the $20^{th}$, $44^{th}$ and $48^{th}$ amino acid residues in SEQ ID NO: 16 are I, G and I respectively, wherein the $33^{rd}$ amino acid residue in SEQ ID NO: 21 is N;
(9) SEQ ID NOs: 16 and 21, respectively, wherein the $20^{th}$, $44^{th}$ and $48^{th}$ amino acid residues in SEQ ID NO: 16 are I, S and M respectively, wherein the $33^{rd}$ amino acid residue in SEQ ID NO: 21 is N;
(10) SEQ ID NOs: 17 and 21, respectively, wherein the $67^{th}$, $68^{th}$ and $72^{nd}$ amino acid residues in SEQ ID NO: 17 are R, A and V respectively, wherein the $33^{rd}$ amino acid residue in SEQ ID NO: 21 is N;
(11) SEQ ID NOs: 17 and 21, respectively, wherein the $67^{th}$, $68^{th}$ and $72^{nd}$ amino acid residues in SEQ ID NO: 17 are K, V and V respectively, wherein the $33^{rd}$ amino acid residue in SEQ ID NO: 21 is N;
(12) SEQ ID NOs: 17 and 21, respectively, wherein the $67^{th}$, $68^{th}$ and $72^{nd}$ amino acid residues in SEQ ID NO: 17 are K, A and R respectively, wherein the $33^{rd}$ amino acid residue in SEQ ID NO: 21 is N;
(13) SEQ ID NOs: 42 and 21, respectively, wherein the $33^{rd}$ amino acid residue in SEQ ID NO: 21 is A;
(14) SEQ ID NOs: 18 and 22, respectively; or
(15) SEQ ID NOs: 19 and 23, respectively.

5. The isolated monoclonal antibody, or the antigen-binding portion thereof, of claim 1, which is an IgG1, IgG2 or IgG4 isotype.

6. The isolated monoclonal antibody, or the antigen-binding portion thereof, of claim 1, comprising a heavy chain constant region comprising the amino acid sequence of SEQ ID NO: 24, linked to the heavy chain variable region, and a light chain constant region comprising the amino acid sequence of SEQ ID NO: 25, linked to the light chain variable region.

7. The isolated monoclonal antibody, or the antigen-binding portion thereof, of claim 1, which is configured to (a) bind human PD-1; (b) bind monkey PD-1; (c) bind mouse PD-1; (d) block PD-1-PD-L1 interaction; and/or (e) provide in vivo anti-tumor activity.

8. The isolated monoclonal antibody, or the antigen-binding portion thereof, of claim 1, which is a mouse, chimeric or humanized antibody or antigen-binding portion thereof.

9. A nucleotide encoding the isolated monoclonal antibody or the antigen-binding portion thereof of claim 1.

10. An expression vector comprising the nucleotide of claim 9.

11. A host cell comprising the expression vector of claim 10.

12. A pharmaceutical composition comprising the isolated monoclonal antibody, or the antigen-binding portion thereof, of claim 1, and a pharmaceutically acceptable carrier.

13. A method for treating a disease associated with PD-1 signaling, comprising administering to a subject a therapeutically effective amount of the pharmaceutical composition of claim 12, wherein the disease is cancer, an infectious disease or an inflammatory disease.

14. The method of claim 13, wherein the cancer is a solid cancer.

15. The method of claim 14, wherein the cancer is non-small-cell lung cancer (NSCLC), renal cell carcinoma (RCC), bladder cancer (BC), colorectal cancer (CRC), hepatocellular carcinoma (HCC), classic Hodgkin lymphoma (cHL), melanoma, head and neck squamous cell carcinoma (HNSCC), colon cancer, cervical cancer, stomach cancer, or gastroesophageal cancer.

16. The method of claim 13, wherein the infectious disease is sepsis, HIV infection, simian immunodeficiency virus infection, HBV infection, or HCV infection.

17. The method of claim 13, wherein the inflammatory disease is rheumatoid arthritis, colitis, lupus-like nephritis, systemic lupus erythematosus, or psoriasis.

18. An isolated monoclonal antibody, or an antigen-binding portion thereof, capable of binding to PD-1, comprising a heavy chain variable region and a light chain variable region, wherein the heavy chain variable region and the light chain variable region comprise amino acid sequences of (1) SEQ ID NOs: 14 and 20, respectively;
(2) SEQ ID NOs: 15 and 21, respectively, wherein the $30^{th}$, $37^{th}$ and $74^{th}$ amino acid residues in SEQ ID NO: 15 are S, M and K respectively, wherein the $33^{rd}$ amino acid residue in SEQ ID NO: 21 is N;
(3) SEQ ID NOs: 15 and 21, respectively, wherein the $30^{th}$, $37^{th}$ and $74^{th}$ amino acid residues in SEQ ID NO: 15 are T, M and K respectively, wherein the $33^{rd}$ amino acid residue in SEQ ID NO: 21 is N;
(4) SEQ ID NOs: 15 and 21, respectively, wherein the $30^{th}$, $37^{th}$ and $74^{th}$ amino acid residues in SEQ ID NO: 15 are S, V and K respectively, wherein the $33^{rd}$ amino acid residue in SEQ ID NO: 21 is N;
(5) SEQ ID NOs: 15 and 21, respectively, wherein the $30^{th}$, $37^{th}$ and $74^{th}$ amino acid residues in SEQ ID NO: 15 are S, M and T respectively, wherein the $33^{rd}$ amino acid residue in SEQ ID NO: 21 is N;
(6) SEQ ID NOs: 15 and 21, respectively, wherein the $30^{th}$, $37^{th}$ and $74^{th}$ amino acid residues in SEQ ID NO: 15 are T, V and T respectively, wherein the $33^{rd}$ amino acid residue in SEQ ID NO: 21 is N;
(7) SEQ ID NOs: 16 and 21, respectively, wherein the $20^{th}$, $44^{th}$ and $48^{th}$ amino acid residues in SEQ ID NO: 16 are V, S and I respectively, wherein the $33^{rd}$ amino acid residue in SEQ ID NO: 21 is N;
(8) SEQ ID NOs: 16 and 21, respectively, wherein the $20^{th}$, $44^{th}$ and $48^{th}$ amino acid residues in SEQ ID NO:

16 are I, G and I respectively, wherein the $33^{rd}$ amino acid residue in SEQ ID NO: 21 is N;

(9) SEQ ID NOs: 16 and 21, respectively, wherein the $20^{th}$, $44^{th}$ and $48^{th}$ amino acid residues in SEQ ID NO: 16 are I, S and M respectively, wherein the $33^{rd}$ amino acid residue in SEQ ID NO: 21 is N;

(10) SEQ ID NOs: 17 and 21, respectively, wherein the $67^{th}$, $68^{th}$ and $72^{nd}$ amino acid residues in SEQ ID NO: 17 are R, A and V respectively, wherein the $33^{rd}$ amino acid residue in SEQ ID NO: 21 is N;

(11) SEQ ID NOs: 17 and 21, respectively, wherein the $67^{th}$, $68^{th}$ and $72^{nd}$ amino acid residues in SEQ ID NO: 17 are K, V and V respectively, wherein the $33^{rd}$ amino acid residue in SEQ ID NO: 21 is N;

(12) SEQ ID NOs: 17 and 21, respectively, wherein the $67^{th}$, $68^{th}$ and $72^{nd}$ amino acid residues in SEQ ID NO: 17 are K, A and R respectively, wherein the $33^{rd}$ amino acid residue in SEQ ID NO: 21 is N;

(13) SEQ ID NOs: 42 and 21, respectively, wherein the $33^{rd}$ amino acid residue in SEQ ID NO: 21 is A;

(14) SEQ ID NOs: 18 and 22, respectively; or

(15) SEQ ID NOs: 19 and 23, respectively.

* * * * *